(12) United States Patent
Yang et al.

(10) Patent No.: US 9,909,101 B2
(45) Date of Patent: *Mar. 6, 2018

(54) METHODS OF PERFUSION CULTURING USING A SHAKE FLASK AND MICROCARRIERS

(71) Applicant: Genzyme Corporation, Cambridge, MA (US)

(72) Inventors: Jianguo Yang, Sudbury, MA (US); Yang Yang, Hopkinton, MA (US); Jennifer Tengtrakool, Framingham, MA (US); Weichang Zhou, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/769,772

(22) PCT Filed: Feb. 21, 2014

(86) PCT No.: PCT/US2014/017803
§ 371 (c)(1),
(2) Date: Aug. 21, 2015

(87) PCT Pub. No.: WO2014/130872
PCT Pub. Date: Aug. 28, 2014

(65) Prior Publication Data
US 2016/0002594 A1 Jan. 7, 2016

Related U.S. Application Data

(60) Provisional application No. 61/768,085, filed on Feb. 22, 2013.

(51) Int. Cl.
*C12N 5/07* (2010.01)
*C12N 5/00* (2006.01)

(52) U.S. Cl.
CPC ........ *C12N 5/0075* (2013.01); *C12N 2510/02* (2013.01); *C12N 2527/00* (2013.01); *C12N 2531/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppestein et al. | |
| 7,354,576 B2 * | 4/2008 | Kakkis | A61K 38/47 424/94.61 |
| 2003/0113915 A1 * | 6/2003 | Heidemann | C12M 33/00 435/383 |
| 2005/0186669 A1 | 8/2005 | Ho et al. | |
| 2008/0199958 A1 | 8/2008 | Hui | |
| 2008/0206819 A1 * | 8/2008 | Tsao | C12N 5/0018 435/70.3 |
| 2009/0042253 A1 | 2/2009 | Hiller et al. | |
| 2009/0233334 A1 | 9/2009 | Hildinger et al. | |
| 2011/0020929 A1 | 1/2011 | Schober et al. | |
| 2012/0164066 A1 | 6/2012 | Greene et al. | |
| 2014/0154726 A1 * | 6/2014 | Yang | C12M 23/08 435/29 |
| 2014/0255994 A1 | 9/2014 | Konstantinov et al. | |
| 2014/0273206 A1 | 9/2014 | Jin et al. | |
| 2015/0158907 A1 | 6/2015 | Zhou et al. | |
| 2015/0183821 A1 | 7/2015 | Konstantinov et al. | |
| 2015/0202595 A1 | 7/2015 | Godawat et al. | |
| 2015/0203529 A1 | 7/2015 | Godawat et al. | |
| 2015/0203531 A1 | 7/2015 | Godawat et al. | |
| 2015/0203532 A1 | 7/2015 | Godawat et al. | |
| 2015/0232505 A1 | 8/2015 | Konstantinov et al. | |
| 2015/0353896 A1 | 12/2015 | Bruninghaus et al. | |
| 2016/0017280 A1 | 1/2016 | Villiger-Oberbek et al. | |
| 2016/0017291 A1 * | 1/2016 | Yang | C12N 5/0075 435/5 |
| 2016/0177361 A1 | 6/2016 | Bae et al. | |

FOREIGN PATENT DOCUMENTS

| | | |
|---|---|---|
| CN | 1564863 | 1/2005 |
| CN | 104450597 A * | 3/2015 |
| WO | WO 02/050251 | 6/2002 |
| WO | WO 2003/029442 | 4/2003 |
| WO | WO 03/039459 | 5/2003 |
| WO | WO 06/033935 | 3/2006 |
| WO | WO 2006/039588 | 4/2006 |
| WO | WO 06/138143 | 12/2006 |
| WO | WO 2008/073620 | 6/2008 |
| WO | WO 08/106515 | 9/2008 |
| WO | WO 2008/127087 | 10/2008 |
| WO | WO 09/034186 | 3/2009 |
| WO | WO 12/078677 | 8/2012 |
| WO | WO 12/152945 | 11/2012 |

(Continued)

OTHER PUBLICATIONS

Shi B. et al. Expansion of Mouse Sertoli Cells on Microcarriers. Cell Proliferation 43(3)275-286, Jun. 2010.*
De Jesus M. et al. TubeSpin Satellites: A Fast Track Approach for Process Development with Animal Cells Using Shaking Technology Biochemical Engineering J 17:217-223, 2004.*
Fernandes-Platzgummer A. et al. Scale-Up of Mouse Embryonic Stem Cell Expansion in Stirred Bioreactors American Institute Chemical Engineers 27(5)1421-1432, Sep./Oct. 2011.*
Costa A. et al. The Impact of Microcarrier Culture Optimization on the Glycosylation Profile of a Monoclonal Antibody. SpringerPlus 2:25, 2013.*
Scott Rosario Growth of Mesenchymal Stromal Cells in Automated Microwell Cultures: Influence of the Engineering Environment on Cell Growth Kinetics and Non-Directed Differentiation. Thesis at The Advanced Centre for Biochemical Engineering, University College London, Sep. 2008.*
U.S. Appl. No. 14/976,486, filed Dec. 21, 2015, Bae et al.
Barrett et al., "Microwell engineering characterization for mammalian cell culture process development," *Biotechnol Bioeng.*, 105(2):260-275, Feb. 1, 2010.

(Continued)

*Primary Examiner* — Ralph J Gitomer
(74) *Attorney, Agent, or Firm* — Fish & Richardson P.C.

(57) ABSTRACT

Provided herein are methods of perfusion culturing an adherent mammalian cell using a shake flask and a plurality of microcarriers, and various methods that utilize these culturing methods.

17 Claims, 17 Drawing Sheets

(56) References Cited

FOREIGN PATENT DOCUMENTS

| WO | WO 13/116449 | 8/2013 |
|---|---|---|
| WO | WO 13/151616 | 10/2013 |
| WO | WO 14/066519 | 5/2014 |
| WO | WO 14/130864 | 8/2014 |
| WO | WO 14/130872 | 8/2014 |
| WO | WO 14/137903 | 9/2014 |
| WO | WO 14/143691 | 9/2014 |
| WO | WO 15/039115 | 3/2015 |
| WO | WO 15/109146 | 7/2015 |
| WO | WO 15/109151 | 7/2015 |
| WO | WO 15/188009 | 12/2015 |
| WO | WO 15/188106 | 12/2015 |
| WO | WO 15/191462 | 12/2015 |
| WO | WO 16/106192 | 6/2016 |

OTHER PUBLICATIONS

Chaturvedi et al., "Comparison of the behavior of CHO cells during cultivation in 24-square deep well microplates and conventional shake flask systems." *Biotechnology Reports.*, 1 (2014): 22-26.
Domansky et al., "Perfused multiwell plate for 3D liver tissue engineering," Lab on a Chip, 10(1):51-58 (Jan. 1, 2010).
Danielson et al., "Maximizing cell densities in miniprep-scale cultures with H15 medium and improved oxygen transfer," Biochemical Engineering J, 17:175-180, 2004.
Nam et al., "The effects of microcarrier culture on recombinant CHO cells under biphasic hypothermic culture conditions," *Cytotechnology*, 59(2):81-91, Epub May 2, 2009.
Rodrigues et al., "Technological progresses in monoclonal antibody production systems," *Biotechnol. Prog.*, 26(2):332-351, Mar.-Apr. 2010.
Scott, "Growth of mesenchymal stromal cells in automated microwell cultures: influence of the engineering environment on cell growth kinetics and non-directed differentiation," (Doctoral dissertation, UCL (University College London), 202 pages, Sep. 2008.
Silk et al., "Fed-batch operation of an industrial cell culture process in shaken microwells," *Biotechnol Lett.*, 32(1):73-78, print Jan. 2010, Epub Sep. 17, 2009..
Strnad et al., "Optimization of cultivation conditions in spin tubes for Chinese hamster ovary cells producing erythropoietin and the comparison of glycosylation patterns in different cultivation vessels," Biotechnology Progress, 26(3):653-663 (2010).
Zhang et al., "A robust high-throughput sandwich cell-based drug screening platform," Biomaterials, 32(4):1229-124 (Feb. 1, 2011).
International Preliminary Report on Patentability for PCT/US2014/017785, dated Sep. 3, 2015, 8 pages.
International Preliminary Report on Patentability for PCT/US2014/017803, dated Sep. 3, 2015, 8 pages.
International Preliminary Report on Patentability in International Application No. PCT/US2013/066410, dated May 7, 2015, 8 pages.
International Search Report and Written Opinion for PCT/US2014/017785, dated May 20, 2014, 11 pages.
International Search Report and Written Opinion for PCT/US2014/017803, dated May 20, 2014, 11 pages.
International Search Report and Written Opinion in International Application No. PCT/US2015/034494, dated Nov. 30, 2015, 24 pages.
Invitation to Pay for PCT/US2015/034494, mailed Aug. 12, 2015, 6 pages.
Notification of Transmittal of the International Search Report and the Written Opinion issued in PCT/US2013/066410 dated Jan. 31, 2014 (12 pages).
U.S. Appl. No. 14/061,657, filed Oct. 23, 2013, Yang et al.
U.S. Appl. No. 14/769,783, filed Aug. 21, 2015, Jianguo et al.
U.S. Appl. No. 14/732,325, filed Jun. 5, 2015, Villiger-Oberbek et al.
U.S. Appl. No. 62/009,058, filed Jun. 6, 2014, Villiger-Oberbek et al
U.S. Appl. No. 62/095,734, filed Dec. 22, 2014, Bae et al.
Clincke et al., "Very high density of CHO cells in perfusion by ATF or TFF in WAVE bioreactor. Part I. Effect of the cell density on the process," *Biotechnol. Prog.* 29(3):754-767, May 2013.
Communication in European Patent Application No. 13786587.9, dated Mar. 15, 2016.
Communication in European Patent Application No. 13786587.9, dated Sep. 27, 2016, 11 pages.
Communication in European Patent Application No. 14709829.7 dated Jun. 27, 2016.
Costa et al., "The impact of microcarrier culture optimization on the glycosylation profile of a monoclonal antibody," *Springer Plus* 2(25):1-10, Jan. 28, 2013.
De Jesus et al., "Tubespin Satellites: A fast track approach for process development with animal cells using shaking technology," Biotechnol. Bioeng. J. 17:217-223, 2004.
Final Office Action in U.S. Appl. No. 14/061,657 dated Aug. 19, 2016.
First Office Action in Chinese Patent Application No. 201380067513.8, dated Apr. 13, 2016, 23 pages.
Gargi et al. "Development of a new bioprocess scheme using frozen seed train intermediates to initiate CHO cell culture manufacturing campaigns," *Biotech. Bioeng.* 110(5):1376-1385, May 4, 2013.
Gebauer and Skerra, "Engineered protein scaffolds as next-generation antibody therapeutics," *Curr. Opin. Chem. Biol.* 13(3):245-255, Jun. 2009.
International Preliminary Report on Patentability for PCT/US2013/066410, dated Apr. 28, 2015.
International Search Report and Written Opinion in International Application No. PCT/US2015/034709, dated Oct. 30, 2015, 13 pages.
International Search Report and Written Opinion in International Application No. PCT/US2015/067040, dated Sep. 5, 2016, 19 pages.
Katakam et al., "Effect of Surfactants on the physical stability of recombinant human growth hormone," J. Pharm. Sciences 84(6):713-716, Jun. 1, 1995.
Kim et al., "Batch, Fed-Batch and Microcarrier Cultures with CHO cell lines in a pressure-cycle driven miniturized bioreactor," *Biotechnol. Bioeng.* vol. 109(1):137-145, 2011.
Non-final Office Action in U.S. Appl. No. 14/769,783, dated Nov. 3, 2016, 36 pages.
Pohlscheidt et al., "Optimizing capacity utilization by large scale 3000 L perfusion in seed train bioreactors," *Biotech. Prog.* 27(5):222-229, Jan. 1, 2012.
Senger et al., "Effect of shear stress on intrinsic CHO culture state and glycosylation of recombinant tissue-type plasminogen activator protein," *Biotechnology Progress* 19(4):1199-209, Jul.-Aug. 2003; Abstract only.
Smelko et al., "Performance of high intensity fed-batch mammalian cell cultures in disposable bioreactor systems," *Biotechnology Progress* 27(5):1358-1364, Sep. 2011.
Soyer et al. Introducing shear stress in the study of bacterial adhesion J. Vis. Exp. (55), e3241, 2011.
Tao et al., "Development and implementation of a perfusion-based high cell density cell banking process," *Biotechnol. Prog.* 27(3):824-829, 2011.
Tordahl et al., "Study of a perfusion process of Chinese hamster ovary cells by ATF filtration in bioreactor ovary cells by ATF filtration in bioreactor," Sep. 11, 2009.
Villiger-Oberbek, "Development and application of a high-throughput platform for perfusion-based cell culture processes," *J. Biotechnol.* 212:21-29, 2015.
Wright et al., "A novel seed-train process: using high-density cell banking, a disposable bioreactor, and perfusion technologies," *BioProcess Int.* Mar. 10, 2015 Supplement.
Written Opinion in Singapore Patent Application No. 11201506339R, dated Jul. 21, 2016.
Written Opinion in Singapore Patent Application No. 11201506343Q, dated Jun. 27, 2016, 5 pages.
Yang et al., "Perfusion seed cultures improve biopharmaceutical fed-batch production capacity and product quality," *Biotech. Prog.* 30(3):616-625, May 1, 2014.

(56) References Cited

OTHER PUBLICATIONS

Non-final Office Action issued in U.S. Appl. No. 14/061,657 dated Nov. 5, 2015, 12 pages.
Chinese Office Action in Application No. 201480022715.5, dated May 15, 2017, 78 pages.
Chinese Office Action in Application No. 201380067513.8, dated Jun. 6, 2017, 15 pages.
Chinese Office Action in Application No. 201480022766.8, dated May 4, 2017, 14 pages.
Singapore Written Opinion in Application No. 11201506339R, dated Jul. 13, 2017, 4 pages.
Final Office Action in U.S. Appl. No. 14/733,630, dated May 11, 2017, 14 pages.
Chinese Office Action in Application No. 2013-80067513.8, dated Dec. 29, 2016, 22 pages.
Communication in European Office Action in European Application No. 13786587.9, dated Feb. 20, 2017, 6 pages.
Final Office Action in U.S. Appl. No. 14/769,783, dated Mar. 28, 2017, 38 pages.
International Preliminary Report on Patentability in International Application No. PCT/US2015/034494, dated Dec. 6, 2016, 14 pages.
Non-final Office Action issued in U.S. Appl. No. 14/733,630 dated Nov. 15, 2016, 13 pages.
Non-final Office Action in U.S. Appl. No. 14/769,772, dated Dec. 6, 2016, 19 pages.
Written Opinion in Singapore Application No. 11201503085V, dated Dec. 7, 2016, 9 pages.

* cited by examiner

US 9,909,101 B2

METHODS OF PERFUSION CULTURING USING A SHAKE FLASK AND MICROCARRIERS

CROSS-REFERENCE TO RELATED APPLICATIONS

This application is a 371 U.S. National of PCT Application No. PCT/US2014/017803, filed Feb. 21, 2014, which claims priority to U.S. Provisional Patent Application Ser. No. 61/768,085, filed Feb. 22, 2013, the entire contents of which are herein incorporated by reference.

TECHNICAL FIELD

This invention relates to methods of molecular biology, cell culture process development, and the manufacture of recombinant proteins.

BACKGROUND

Mammalian cells containing a nucleic acid that encodes a recombinant protein are often used to produce therapeutically or commercially important proteins. Although several high throughput (HT) cell culture systems have been used within the biotechnology industry for fed-batch processes for years, no HT model for a perfusion-based cell culture using shake flasks and microcarriers is known to exist.

Shake flasks containing microcarriers have been used in short-term batch (non-perfusion) culture processes to produce viral vaccines. The cell densities in these methods of producing viral vaccines were low due to the shear stress caused by the microcarriers. In addition, the recovery of the viral products from the culture was difficult.

SUMMARY

The present invention is based, at least in part, on the discovery that culturing a mammalian cell in the specific manner described herein results in a substantially improved viable cell density and recombinant protein production, and is able to effectively model (e.g., an accurate scale-down model) the recombinant protein production of a larger-scale continuous-perfusion bioreactor. Thus, the present specification includes methods of culturing a mammalian cell that include: providing a shake flask containing a mammalian cell disposed in a first liquid culture medium, where the first liquid culture medium occupies, e.g., about 20% to about 30% of the volume of the shake flask, and contains a plurality of microcarriers at a concentration of about 1.0 g/L to about 15.0 g/L; incubating the shake flask for a period of time at about 32° C. to about 39° C., e.g., about 32° C. to about 37° C., and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal. Also provided are various methods that utilize these culturing methods.

Provided herein are methods of culturing a mammalian cell. These methods include: providing a shake flask containing a mammalian cell disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal. In some embodiments of any of these methods, the first volume of the first liquid culture medium is substantially free of the microcarriers. In some embodiments of any of these methods, the first liquid culture medium occupies about 25% to about 30% of the volume of the shake flask. In some embodiments of any of these methods, at the beginning of the period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the CHO cell contains a nucleic acid encoding a recombinant protein. In some embodiments of any of these methods, the recombinant protein is an immunoglobulin, an enzyme, a growth factor, a protein fragment, or an engineered protein. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium is the same as the second liquid culture medium. In some embodiments of any of these methods, the first liquid culture medium is different from the second liquid culture medium. In some embodiments of any of these methods, the shake flask is gas-permeable and has a volume of between about 20 mL to about 1 L. In some embodiments of any of these methods, the mammalian cell is suspended in about 40 mL to about 80 mL of the first liquid culture medium. In some embodiments of any of these methods, the first liquid culture medium and/or second liquid culture medium is selected from the group of: a chemically-defined liquid culture medium, a serum-free liquid culture medium, a serum-containing liquid culture medium, an animal-derived component free liquid culture medium, and a protein-free medium. In some embodiments of any of these methods, after about the first 48 to 96 hours of the period of time, in each 24-hour period, the first volume of the first liquid culture medium removed and the second volume of the second liquid culture medium added is about 30% to about 95% of the volume of the first liquid culture medium. In some embodiments of any of these methods, the agitation is ceased for a period of time of at least 30 seconds prior to removing the first volume of the first liquid culture medium. In some embodiments of any of these methods, the plurality of microcarriers has a mean diameter of between about 150 µm to about 800 µm. In some embodiments of any of these methods, the plurality of microcarriers contains one or more pores. In some embodiments of any of these methods, the one or more pores has a mean diameter of about 25 µm to about 35 µm. In some embodiments of any of these methods, the shake flask is incubated at a reactor angle of about 25 degrees to about 90 degrees from horizontal, or at an angle that is about 45 degrees relative to the benchtop or the horizon.

Also provided are methods of culturing a mammalian cell that include: (a) providing a shake flask containing a mammalian cell disposed in a first liquid culture medium that occupies about 20% to about 30% of the volume of the shake flask and contains a plurality of microcarriers in a concentration of about 1.0 g/L to about 15.0 g/L; (b) incubating the shake flask for a first time period at about 35° C. to about 39° C. with a rotary agitation of about 85 revolutions per minute (RPM) to about 125 RPM, and after about the first 48 to 96 hours of the first period of time, in each subsequent 24-hour period, (i) continuously or periodically removing a first volume of the first liquid culture medium that is substantially free of microcarriers from the shake flask, where the first volume is about 10% to about 95% of the volume of the first liquid culture medium; and (ii) adding to the shake flask a second volume of a second liquid culture medium, where the first and second volumes are about equal; (c) incubating the shake flask after the cell concentration reaches about target cell density for a second time period of about 2 days to about 7 days, at about 32° C. to about 39° C. with the rotary agitation, and in each 24-hour period, performing steps (b)(i) and (b)(ii), where the first and second liquid culture media used in step (b) are of a substantially different type from those used in step (c); and (d) incubating the shake flask for a third time period greater than 2 days, at about 35° C. to about 39° C. with the rotary agitation, and in each 24-hour period, performing steps (b)(i) and (b)(ii), where the first and second liquid culture media used in step (c) are of the same type as those used in step (d). In some embodiments of any of these methods, the first liquid culture medium occupies about 25% to about 30% of the volume of the shake flask. In some embodiments of any of these methods, at the beginning of the first period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the CHO cell contains a nucleic acid encoding a recombinant protein. In some embodiments of any of these methods, the recombinant protein is a secreted immunoglobulin, a secreted enzyme, a secreted growth factor, a secreted protein fragment, or a secreted engineered protein. In some embodiments of any of these methods, the removing of the first volume of the first liquid culture medium, and the adding of the second volume of the second liquid culture medium in one or more of the first time period, the second time period, and the third time period is performed simultaneously. In some embodiments of any of these methods, the removing of the first volume of the first liquid culture medium, and the adding of the second volume of the second liquid culture medium in one or more of the first time period, the second time period, and the third time period is performed continuously. In some embodiments of any of these methods, the removing of the first volume of the first liquid culture medium, and the adding of the second volume of the second liquid culture medium in one of more of the first time period, the second time period, and the third time period is performed periodically. In some embodiments of any of these methods, the shake flask is gas-permeable and has a volume of between about 20 mL to about 1 L. In some embodiments of any of these methods, the volume of the first liquid culture medium is about 40 mL to about 80 mL. In some embodiments of any of these methods, the first liquid culture medium and second liquid culture medium used in the first time period is serum-containing liquid culture medium or an animal-derived component-containing liquid culture medium, and the first liquid culture medium and the second liquid culture medium used in the second time period and the third time period is a serum-free liquid culture medium, an animal-derived component-free liquid culture medium, or a protein-free medium. In some embodiments of any of these methods, the agitation is ceased for at least 30 seconds prior to removing the first volume of the first liquid culture medium from the shake flask during one or more of the first time period, the second time period, and the third time period. In some embodiments of any of these methods, the plurality of microcarriers has a mean diameter of between about 200 µm to about 800 µm. In some embodiments of any of these methods, the plurality of microcarriers contains one or more pores. In some embodiments of any of these methods, the one or more pores has a mean diameter of about 25 µm to about 35 µm. In some embodiments of any of these methods, the first volume of the first liquid culture medium removed during the third period of time contains a substantial number of microcarriers. In some embodiments of any of these methods, the first volume of the first liquid culture medium removed during the third period of time is substantially free of microcarriers. In some embodiments of any of these methods, the first volume of the first liquid culture medium removed and the second volume of the second liquid culture medium added in one or more of the first time period, the second time period, and the third time period is about 70% of the volume of the first liquid culture medium. In some embodiments of any of these methods, the shake flask is incubated in one or more of (b), (c), and (c) at a reactor angle of about 25 degrees to about 90 degrees from horizontal, or at an angle that is about 45 degrees relative to the benchtop or the horizon.

Also provided are methods of producing a recombinant protein. These methods include: providing a shake flask containing a mammalian cell containing a nucleic acid encoding a recombinant protein disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal; and recovering the recombinant protein from the mammalian cell or from the first and/or second liquid culture medium. In some embodiments of any of these methods, the recombinant protein is recovered from the mammalian cell. In some embodiments of any of these methods, the recombinant protein is recovered from the mammalian cell. In some embodiments of any of these methods, the recombinant protein is recovered from the first and/or second liquid culture medium. In some embodiments of any of these methods, the first volume of the first liquid culture medium removed is substantially free of microcarriers. In some embodiments of any of these methods, the first liquid culture medium occupies about 25% to about 30% of the volume of the shake flask. In some embodiments of any of these methods, at the beginning of the period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the recombinant protein is an immunoglobulin, an enzyme, a growth factor, a protein fragment, or an engineered protein. In some embodiments of any of these methods, the recombinant protein is secreted into the first and/or second liquid culture medium. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium is the same as the second liquid culture medium. In some embodiments of any of these method, the first liquid culture medium is different from the second liquid culture medium. In some embodiments of any of these methods, the shake flask is gas-permeable and has a volume of between about 20 mL to about 1 L. In some embodiments of any of these methods, the mammalian cell is suspended in about 40 mL to about 80 mL of the first liquid culture medium. In some embodiments of any of these methods, the first liquid culture medium and/or second liquid culture medium is selected from the group of: a chemically-defined liquid culture medium, a serum-free liquid culture medium, a serum-containing liquid culture medium, an animal-derived component-free liquid culture medium, and a protein-free medium. In some embodiments of any of these methods, after about the first 48 to 96 hours of the period of time, in each 24-hour period, the first volume of the first liquid culture medium removed and the second volume of the second liquid culture medium added is about 30% to about 95% of the volume of the first liquid culture medium. In some embodiments of any of these methods, the agitation is ceased for a period of time of at least 30 seconds prior to removing the first volume of the first liquid culture medium. In some embodiments of any of these methods, the plurality of microcarriers has a mean diameter of between about 200 µm to about 800 µm. In some embodiments of any of these methods, the plurality of microcarriers contains one or more pores. In some embodiments of any of these methods, the one or more pores has a mean diameter of about 25 µm to about 35 µm. In some embodiments of any of these methods, the shake flask is incubated at a reactor angle of about 25 degrees to about 90 degrees from horizontal, or at an angle that is about 45 degrees relative to the benchtop or the horizon.

Also provided are methods of producing a recombinant protein that include: (a) providing a shake flask containing a mammalian cell containing a nucleic acid encoding a recombinant protein disposed in a first liquid culture medium, where the first liquid culture medium occupies about 20% to about 30% of the volume of the shake flask and contains a plurality of microcarriers in a concentration of about 1.0 g/L to about 15.0 g/L; (b) incubating the shake flask for a first time period at about 35° C. to about 39° C. with a rotary agitation of about 85 revolutions per minute (RPM) to about 125 RPM, and after about the first 48 hours to 96 hours of the first period of time, in each subsequent 24-hour period, (i) continuously or periodically removing a first volume of the first liquid culture medium that is substantially free of microcarriers from the shake flask, where the first volume is about 10% to about 95% of the volume of the first liquid culture medium; and (ii) adding to the shake flask a second volume of a second liquid culture medium, where the first and second volumes are about equal; (c) incubating the shake flask after the cell concentration reaches about target cell density for a second time period of about 2 days to about 7 days, at about 32° C. to about 39° C. with the rotary agitation, and in each 24-hour period, performing steps (b)(i) and (b)(ii), where the first and second liquid culture media used in step (b) are of a substantially different type from those used in step (c); (d) incubating the shake flask for a third time period greater than 2 days, at about 35° C. to about 39° C. with the rotary agitation, and in each 24-hour period, performing steps (b)(i) and (b)(ii), where the first and second liquid culture media used in step (c) are of the same type as those used in step (d); and (e) recovering the recombinant protein from the mammalian cell or the first and/or second liquid culture medium used during the first, second, and/or third period of time. In some embodiments of any of these methods, the recombinant protein is recovered from the mammalian cell. In some embodiments of any of these methods, the recombinant protein is recovered from the first and/or second liquid culture medium used during one or more of the first, second, and third period of time. In some embodiments of any of these methods, the first liquid culture medium occupies about 25% to about 30% of the volume of the shake flask. In some embodiments of any of these methods, at the beginning of the first period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the recombinant protein is an immunoglobulin, an enzyme, a growth factor, a protein fragment, or an engineered protein. In some embodiments of any of these methods, the recombinant protein is secreted into the first and/or second liquid culture medium used during one or more of the first period of time, the second period of time, and the third period of time. In some embodiments of any of these methods, the removing of the first volume of the first liquid culture medium and the adding of the second volume of the second liquid culture medium in one or more of the first time period, the second time period, and the third time period is performed simultaneously. In some embodiments of any of these methods, the removing of the first volume of the first liquid culture medium and the adding of the second volume of the second liquid culture medium in one or more of the first time period, the second time period, and the third time period is performed continuously. In some embodiments of any of these methods, the removing of the first volume of the first liquid culture medium and the adding of the second volume of the second liquid culture medium in one of more of the first time period, the second time period, and the third time period is performed periodically. In some embodiments of any of these methods, the shake flask is gas-permeable and has a volume of between about 20 mL to about 1 L. In some embodiments of any of these methods, the volume of the first liquid culture medium is about 40 mL to about 80 mL. In some embodiments of any of these methods, the first liquid culture medium and second liquid culture medium used in the first time period is serum-containing liquid culture medium or an animal-derived component-containing liquid culture medium, and the first liquid culture medium and second liquid culture medium used in the second time period and the third time period is a serum-free liquid culture medium, an animal-derived component free liquid culture medium, or a protein-free medium. In some embodiments of any of these methods, the agitation is ceased for at least 30 seconds prior to removing the first volume of the first liquid culture medium, from the shake flask during one or more of the first time period, the second time period, and the third time period. In some embodiments of any of these methods, the plurality of microcarriers has a mean diameter of between about 200 μm to about 800 μm. In some embodiments of any of these methods, the plurality of microcarrier contains one or more pores. In some embodiments of any of these methods, the one or more pores has a mean diameter of about 25 μm to about 35 μm. In some embodiments of any of these methods, the first volume of the liquid culture medium removed during the third period of time contains a substantial number of microcarriers. In some embodiments of any of these methods, the first volume of the liquid culture medium removed during the third period of time is substantially free of microcarriers. In some embodiments of any of these methods, the first volume of the first liquid culture medium removed and the second volume of the second liquid culture medium added in one or more of the first time period, the second time period, and the third time period is about 70% of the volume of the first liquid culture medium. In some embodiments of any of these methods, the shake flask is incubated in one or more of (b), (c), and (d) at a reactor angle of about 25 degrees to about 90 degrees from horizontal, or at an angle that is about 45 degrees relative to the benchtop or the horizon.

Also provided are methods for testing a manufacturing process for making a recombinant protein. These methods include: providing a shake flask containing a mammalian cell containing a nucleic acid encoding a recombinant protein disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; and comparing the amount of recombinant protein present in the cell or in the first and/or second culture medium to a reference level of recombinant protein. In some embodiments of any of these methods, the first volume of the first liquid culture medium is substantially free of mammalian cells. In some embodiments of any of these methods, the reference level of recombinant protein is a level of recombinant protein produced using a different culturing method. In some embodiments of any of these methods, the different culturing method utilizes a different first or second liquid culture medium, a different mammalian cell, a different temperature, a different level of agitation, a different shake flask, or a different microcarrier. In some embodiments of any of these methods, the different culturing method utilizes different raw materials, anti-clumping agents, or chemically-defined liquid culture media. In some embodiments of any of these methods, the method is used to perform high throughput cell culture experiments to perform a design-of-experiment (DOE) or a quality-by-design (QBD) study. In some embodiments of any of these methods, the first liquid culture medium occupies about 25% to about 30% of the volume of the shake flask. In some embodiments of any of these methods, the shake flask is gas-permeable and has a volume of between about 20 mL to about 1 L. In some embodiments of any of these methods, the mammalian cell is suspended in about 40 mL to about 80 mL of the first liquid culture medium. In some embodiments of any of the methods described herein, the mammalian cell is a Chinese hamster ovary (CHO) cell. In some embodiments of any of these methods, the recombinant protein is a secreted immunoglobulin, a secreted enzyme, a secreted growth factor, a secreted protein fragment, or a secreted engineered protein, and where the recombinant protein is recovered from the first or second culture medium. In some embodiments of any of these methods, the recombinant protein is recovered from the mammalian cell. In some embodiments of any of these methods, the recombinant protein is an immunoglobulin, an enzyme, a growth factor, a protein fragment, or an engineered protein. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium and/or second liquid culture medium is selected from the group of: a chemically-defined liquid culture medium, a serum-free liquid culture medium, a serum-containing liquid culture medium, an animal-derived component free liquid culture medium, and a protein-free medium. In some embodiments of any of these methods, the shake flask is incubated at a reactor angle of about 25 degrees to about 90 degrees from horizontal, or at an angle that is about 45 degrees relative to the benchtop or the horizon.

Also provided are methods of testing the efficacy of a first or second liquid culture medium, a raw ingredient or supplement present in a first or second liquid culture medium, or a source of a mammalian cell for use in a method of producing a recombinant protein. These methods include: providing a shake flask containing a mammalian cell disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method that uses one or more of a different first or second liquid culture medium, a different raw ingredient or supplement present in the first or second liquid culture medium, or a different source of a mammalian cell; and identifying the first or second liquid culture medium, the raw ingredient or supplement present in the first or second liquid culture medium, or the source of the mammalian cell that is associated with an increased amount of recombinant protein as compared to the reference level as being efficacious for use in a method of producing a recombinant protein. In some embodiments of any of these methods, the shake flask is incubated at a reactor angle of about 25 degrees to about 90 degrees from horizontal, or at an angle that is about 45 degrees relative to the benchtop or the horizon.

Also provided are methods of optimizing a manufacturing process of producing a recombinant protein. These methods include: providing a shake flask containing a mammalian cell disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method; and identifying and removing or altering in a manufacturing process any culture components or parameters that are associated with a decrease in the amount of recombinant protein produced as compared to the reference level, or identifying and adding to a manufacturing process any culture components or parameters that are associated with an increase in the amount of recombinant protein produced as compared to the reference level. In some embodiments of any of these methods, the shake flask is incubated at a reactor angle of about 25 degrees to about 90 degrees from horizontal, or at an angle that is about 45 degrees relative to the benchtop or the horizon.

Also provided are methods of testing for the presence of a contaminant in a first or second liquid culture medium, a raw material used to generate a first or second liquid culture medium, or a source of a mammalian cell. These methods include: providing a shake flask containing a mammalian cell disposed in a first liquid culture medium, where the first liquid culture medium occupies about 20% to about 30% of the volume of the shake flask and contains a plurality of microcarriers at a concentration of about 1.0 g/L to about 15.0 g/L; incubating the shake flask for a period of time at about 32° C. to about 39° C. and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method that uses one or more of a different first or second liquid culture medium, a different raw material to generate the first or second liquid culture medium, or a different source of the mammalian cell; and identifying the first or second liquid culture medium, the raw material used to generate the first or second liquid culture medium, or the source of a mammalian cell as containing a contaminant when the level of recombinant protein produced is less than the reference level. In some embodiments of any of these methods, the contaminant is a biological contaminant. In some embodiments of any of these methods, the biological contaminant is selected from the group of: mycobacterium, a fungus, a bacterium, a virus, and an undesired mammalian cell. In some embodiments of any of these methods, the shake flask is incubated at a reactor angle of about 25 degrees to about 90 degrees from horizontal, or at an angle that is about 45 degrees relative to the benchtop or the horizon.

As used herein, the word "a" or "plurality" before a noun represents one or more of the particular noun. For example, the phrase "a mammalian cell" represents "one or more mammalian cells," and the phrase "plurality of microcarriers" means "one or more microcarriers."

The term "mammalian cell" means any cell from or derived from any mammal (e.g., a human, a hamster, a mouse, a green monkey, a rat, a pig, a cow, or a rabbit. In some embodiments, the mammalian cell can be, e.g., an immortalized cell, a differentiated cell, or an undifferentiated cell.

The term "target cell density" means a specific concentration of cells per volume of culture medium for producing a recombinant protein in culture. Target cell density can vary depending upon the specific mammalian cell cultured. For example, the target cell density can be about $1.0 \times 10^6$ cells/mL to about $50 \times 10^6$ cells/mL (e.g., between about $2.0 \times 10^6$ cells/mL to about $3.0 \times 10^6$ cells/mL).

The term "substantially free" means a composition (e.g., a liquid culture medium) that is at least or about 90% free (e.g., at least or about 95%, 96%, 97%, 98%, or at least or about 99% free, or about 100% free) of a specific substance (e.g., a mammalian cell or microcarriers).

The term "culturing" or "cell culturing" means the maintenance or growth of a mammalian cell in a liquid culture medium under a controlled set of physical conditions.

The term "shake flask" is meant a vessel (e.g., a sterile vessel) that can hold a volume of liquid culture medium that has at least one gas permeable surface (e.g., an end that has at a gas-permeable element, e.g., a membrane, which may also act as a sterile barrier) and/or at least one vent cap, and at least a portion of its shape is approximately frustoconical. For example, a shake flask can be a cell culture flask, such as a T-flask, an Erlenmeyer flask, or any art-recognized modified version thereof.

The term "liquid culture medium" means a fluid that contains sufficient nutrients to allow a mammalian cell to grow in the medium in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, selenium, and other necessary trace metals, and sodium bicarbonate. A liquid culture medium may contain serum from a mammal.

In some instances, a liquid culture medium does not contain serum or another extract from a mammal (a defined liquid culture medium). A liquid culture medium may contain trace metals, a mammalian growth hormone, and/or a mammalian growth factor. Non-limiting examples of liquid culture medium are described herein and additional examples are known in the art and are commercially available.

The phrase "substantially different type of liquid culture medium" means a liquid culture medium that contains a substantially different nutrient profile from another liquid culture medium. For example, a liquid culture medium that contains one or more of a mammalian serum, mammalian protein, or a mammalian protein fraction or extract (e.g., a serum-containing liquid culture medium) is a substantially different type of liquid culture medium than one that does not contain any of a mammalian serum, mammalian protein, or a mammalian protein fraction or extract (e.g., an animal-derived component free liquid culture medium, a serum-free liquid culture medium, a chemically-defined liquid culture medium, and a protein-free liquid culture medium).

The phrase "substantially the same type of liquid culture medium" means a liquid culture medium that contains about the same nutrient profile as compared to another liquid culture medium. For example, if liquid culture medium A and liquid culture medium B both contain one or more of a mammalian serum, mammalian protein, and a mammalian protein fraction or extract (e.g., a serum-containing liquid culture medium), there are substantially the same. In another example, if liquid culture medium A and liquid culture medium B both do not contain any of a mammalian serum, mammalian protein, and a mammalian protein fraction or extract (e.g., an animal-derived component free liquid culture medium, a serum-free liquid culture medium, a chemically-defined liquid culture medium, and a protein-free liquid culture medium), they are substantially the same.

The term "microcarrier" means a particle (e.g., an organic polymer) that has a size of between 20 μm to about 1000 μm that contains a surface that is permissive or promotes attachment of a mammalian cell (e.g., any of the mammalian cells described herein or known in the art). A microcarrier can contain one or more pores (e.g., pores with an average diameter of about 10 μm to about 100 μm). Non-limiting examples of microcarriers are described herein. Additional examples of microcarriers are known in the art. A microcarrier can contain, e.g., a polymer (e.g., cellulose, polyethylene glycol, or poly-(lactic-co-glycolic acid)).

The term "animal-derived component free liquid culture medium" means a liquid culture medium that does not contain any components (e.g., proteins or serum) derived from an animal.

The term "serum-free liquid culture medium" means a liquid culture medium that does not contain animal serum.

The term "serum-containing liquid culture medium" means a liquid culture medium that contains animal serum.

The term "chemically-defined liquid culture medium" means a liquid culture medium in which substantially all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

"Rotary agitation" is a term well-known in the art and refers to the movement of a shake flask in a generally circular fashion, e.g., clock-wise or counter-clockwise, in order to, e.g., increase the dissolved $O_2$ concentration in a liquid culture medium contained therein. Agitation can be performed using any art-known method, e.g., an instrument that moves the shake flask in a circular or ellipsoidal motion, such as a rotary shaker. Exemplary devices that can be used to perform rotary agitation are described herein. Additional examples of such devices are also known in the art and are commercially available.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')$_2$ fragment, or an a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the methods described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "recover" or "recovering" in certain contexts means at least partially purifying or isolating (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a recombinant protein from one or more other components present in the cell culture medium (e.g., mammalian cells or culture medium proteins) or one or more other components (e.g., DNA, RNA, or other proteins) present in a mammalian cell lysate. Non-limiting methods for recovering a protein from a liquid culture medium or from a mammalian cell lysate are described herein and others are known in the art.

The term "secreted protein" or "secreted recombinant protein" means a protein or a recombinant protein that originally contained at least one secretion signal sequence when it is translated within a mammalian cell, and through, at least in part, enzymatic cleavage of the secretion signal sequence in the mammalian cell, is released into the extracellular space (e.g., a liquid culture medium).

The phrase "gradient perfusion" is art-known and refers to the incremental change (e.g., increase or decrease) in the volume of culture medium removed and added to an initial culture over incremental periods (e.g., an about 24-hour period, a period of between about 1 minute and about 24-hours, or a period of greater than 24 hours) during the culturing period (e.g., the culture medium re-feed rate on a daily basis). The fraction of media removed and replaced each day can vary depending on the particular cells being cultured, the initial seeding density, and the cell density at a particular time.

The term "feed-batch culture" means the incremental or continuous addition of a second liquid culture medium to an initial cell culture without substantial or significant removal of the first liquid culture medium from the cell culture. In some instances, the second liquid culture medium is the same as the first liquid culture medium. In other instances, the second liquid culture medium is a concentrated form of the first liquid culture medium and/or is added as a dry powder.

The term "reactor angle" refers to the angle of deviation from the horizontal position that the shake flask containing a mammalian cell is placed during the culturing methods described herein. For example, when the shake flask containing a mammalian cell is standing vertical relative to the lab bench or ground, the reactor angle is 90°, and when the shake flask containing a mammalian cell is placed horizontal relative to the lab bench or ground, the reactor angle is 0°. In another example, when a shake flask containing a mammalian cell is placed equidistant between the vertical and horizontal positions (relative to the lab bench or ground), the reactor angle is 45°.

"Specific productivity rate" or "SPR" as used herein refers to the mass or enzymatic activity of a recombinant protein produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" as used herein refers to the mass or enzymatic activity of recombinant protein produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
FIG. 1 is a diagram showing an exemplary rack that can be used to position the shake flask at an angle of about 45 degrees relative to the benchtop or the horizon, that can be used in any of the methods described herein.

Provided herein are improved methods of culturing a mammalian cell in a shake flask using a plurality of microcarriers and batch re-feed perfusion. The culturing methods described herein can achieve high mammalian cell concentration levels, thereby improving the overall efficiency of a culturing process and providing high yields of desirable cellular products, such as recombinant proteins. For example, the methods can provide a viable mammalian cell concentration (e.g., in the first and/or second liquid culture medium, or the first and/or second liquid culture medium in one or more of the first, second, and third time periods) of greater than $2\times10^6$ cells per mL, greater than $3\times10^6$ cells/mL, greater than $4\times10^6$ cells/mL, greater than $5\times10^6$ cells/mL, greater than $6\times10^6$ cells/mL, greater than $7\times10^6$ cells/mL, greater than $8\times10^6$ cells/mL, greater than $9\times10^6$ cells/mL, greater than $10\times10^6$ cells/mL, greater than $12\times10^6$ cells/mL, greater than $14\times10^6$ cells/mL, greater than $16\times10^6$ cells/mL, greater than $18\times10^6$ cells/mL, greater than $20\times10^6$ cells/mL, greater than $25\times10^6$ cells/mL, greater than $30\times10^6$ cells/mL, greater than $35\times10^6$ cells/mL, greater than $40\times10^6$ cells/mL, greater than $45\times10^6$ cells/mL, or greater than $50\times10^6$ cells/mL. For example, the culturing method can result in a viable mammalian cell concentration of between $1\times10^6$ cells/mL and $3\times10^6$ cells/mL, between $3\times10^6$ cells/mL and $5\times10^6$ cells/mL, between $5\times10^6$ cells/mL and $7\times10^6$ cells/mL, between $7\times10^6$ cells/mL and $9\times10^6$ cells/mL, between $9\times10\times10^6$ cells/mL and $11\times10^6$ cells/mL, between $10\times10^6$ cells/mL and $12\times10^6$ cells/mL, between $11\times10^6$ cells/mL and $13\times10^6$ cells/mL, between $12\times10^6$ cells/mL and $14\times10^6$ cells/mL, between $14\times10^6$ cells/mL and $16\times10^6$ cells/mL, between $16\times10^6$ cells/mL and $18\times10^6$ cells/mL, between $18\times10^6$ cells/mL and $20\times10^6$ cells/mL, between $20\times10^6$ cells/mL and $25\times10^6$ cells/mL, between $25\times10^6$ cells/mL and $30\times10^6$ cells/mL, between $30\times10^6$ cells/mL and $35\times10^6$ cells/mL, between $35\times10^6$ cells/mL and $40\times10^6$ cells/mL, between $40\times10^6$ cells/mL and $45\times10^6$ cells/mL, between $45 \times 10^6$ cells/mL and $50 \times 10^6$ cells/mL, or greater than $50 \times 10^6$ cells/mL. In some instances, the methods described herein result in an increase in the biological activity of a recombinant protein (e.g., as compared to the biological activity of a recombinant protein produced by a different method).

A variety of different methods to determine the cell density or viable cell density can be used, and are well-known in the art. For example, a sample of the cell culture containing microcarriers can be treated to release the cells from the surface of the microcarriers, and the released cells can optionally be diluted in physiological buffer, and the cell suspension (e.g., diluted cell suspension) placed in a hemocytometer and counted using light microscopy. In another method, the viable cell density can be determined using a similar method, but including in the physiological buffer a dye that is selectively taken up by non-viable cells (e.g., trypan blue, such as Vi-CELL method from Beckman Coulter (see Beckman Coulter website)). In yet another example, the cell density or viable cell density can be determined using fluorescence-assisted flow cytometry (e.g., GUAVA from Merck Millipore (see Millipore website), and other cell counting methods.

In some instances, the culturing method results in a significantly improved specific productivity rate. For example, the specific productivity rate achieved by the methods provided herein can be at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold greater than the specific productivity rate achieved using an art-known culturing method (e.g., a different shake flask culture method). The volume productivity achieved by the present methods can be at least 300 units/L/day, at least 400 units/L/day, at least 500 units/L/day, at least 600 units/L/day, at least about 800 units/L/day, at least about 1,000 units/L/day, at least about 1,200 units/L/day, at least about 1,400 units/L/day, at least about 1,600 units/L/day, at least about 1,800 units/L/day, at least about 2,000 units/L/day, at least about 2,200 units/L/day, at least about 3,000 units/L/day, at least 4,000 units/L/day, at least 5,000 units/L/day, at least 6,000 units/L/day, at least 7,000 units/L/day, at least 8,000 units/L/day, at least 9,000 units/L/day, at least 10,000 units/L/day, or higher than 10,000 units/L/day (e.g., in the first and/or second liquid culture medium, or the first and/or second liquid culture medium used in one or more of the first, second, and third time period). In some embodiments, the productivity achieved by the present methods can be at least 0.2 g/L, at least 0.5 g/L, at least 0.75 g/L, at least 1.0 g/L, at least 1.25 g/L, at least 1.5 g/L, at least 1.75 g/L, at least 2.0 g/L, at least 2.5 g/L, at least 3.0 g/L, at least 3.5 g/L, at least 4.0 g/L, at least 4.5 g/L, or at least 5.0 g/L (e.g., in the first and/or second liquid culture medium, or the first and/or second liquid culture medium used in the first, second, and third time period).

The biological activity of a recombinant protein can be assessed using a variety of methods known in the art, and will depend on the activity of the specific recombinant protein. For example, the biological activity of a recombinant protein that is an immunoglobulin (e.g., an antibody or an antibody fragment) can be determined by measuring the affinity of the antibody to bind to its specific epitope (e.g., using Biocore or competitive enzyme-linked immunosorbent assays). The recombinant protein may be an enzyme (e.g., a recombinant galactosidase, e.g., a recombinant alpha-galactosidase) and the biological activity may be determined by measuring the enzyme's activity (e.g., determining the catalytic rate constant of the enzyme by measuring a decrease in the concentration of a detectable substrate or an increase in the concentration of a detectable product (e.g., using spectrophotometry or light emission). For example, the biological activity of a recombinant galactosidase can be detected by measuring a decrease in the level of globotriasylceramide (GL-3) or galabiosylceramide, or an increase in the level of ceramide dihexoside or galactose.

Methods of Culturing a Mammalian Cell

In a method that is exemplary of those described herein, a shake flask is provided. A first liquid culture medium is added to the shake flask such that the medium occupies, about 10% to about 40%, e.g., about 20% to about 30% (e.g., about 20% to about 22%, about 22% to about 24%, about 24% to about 26%, about 26% to about 28%, about 28% to about 30%, about 20% to about 25%, or about 25% to about 30%) of the volume of the shake flask. At least one mammalian cell and a plurality of microcarriers (a final concentration in the shake flask of about 1.0 g/L to about 15.0 g/L, e.g., a final concentration in the shake flask of between about 1.0 g/L to about 2.5 g/L, about 1.0 g/L to about 2.0 g/L, about 1.0 g/L to about 1.75 g/L, about 1.0 g/L to about 1.5 g/L, about 1.0 g/L to about 1.25 g/L, about 2.5 g/L to 5.0 g/L, about 5.0 g/L to about 7.5 g/L, about 7.5 g/L to about 10.0 g/L, about 10.0 g/L to about 12.5 g/L, about 12.5 g/L to about 15.0 g/L, about 1.0 g/L to about 5.0 g/L, about 5.0 g/L to about 10.0 g/L, about 10.0 g/L to about 15.0 g/L, about 2.5 g/L to about 3.5 g/L, about 3.0 g/L to about 4.0 g/L, about 4.0 g/L to about 5.0 g/L, about 5.0 g/L to about 6.0 g/L, about 6.0 g/L to about 7.0 g/L, about 7.0 g/L to about 8.0 g/L, about 8.0 g/L to about 9.0 g/L, about 9.0 g/L to about 10.0 g/L, about 10.0 g/L to about 11.0 g/L, about 11.0 g/L to about 12.0 g/L, about 12.0 g/L to about 13.0 g/L, about 13.0 g/L to about 14.0 g/L, or about 14.0 g/L to about 15.0 g/L) is added to the first liquid culture medium, i.e., either before the medium is added to the shake flask or afterward. As one skilled in the art can appreciate, the steps of the addition of the liquid culture medium, a mammalian cell, and the liquid culture medium to the shake flask can occur in any order. The shake flask is incubated for a period of time at about 32° C. to about 39° C. (e.g., 32° C. to 34° C., 32° C. to 37° C., 34° C. to 37° C., 37° C. to 39° C.) and agitated, e.g., on a rotary shaking device, at about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, or about 100 RPM to about 125 RPM). The cells can be incubated, for example, in an incubator, such as a shake incubator with throw (orbit) diameter of 25 mm or from about 3 mm to about 50 mm, while changing the RPM accordingly. After the first 48 to 96 hours of the period of time of incubation, continuously or periodically over the period of time, a first volume of the first liquid culture medium (e.g., containing any mammalian cell concentration, e.g., a first volume of first liquid culture medium which is or is made substantially free of mammalian cells and/or microcarriers) is removed, and a second volume of a second liquid culture medium is added to the first liquid culture medium. Typically, the first and the second volumes are roughly equal, but can vary by a small amount, e.g., by up to about 10% when the first and second volumes are compared. In some embodiments, the second volume of the second liquid culture medium added is less (e.g., at most about 1%, 2%, 3%, 4%, 5%, 6%, 7%, 8%, 9%, or 10% less) or more (e.g., at most about 1%, 2%, 3%, 4%, 5%, 6%, 7%, 8%, 9%, or 10% more) than the first volume of the first liquid culture medium removed. As is known in the art, the term incubating can include short periods of time (e.g., between 10 seconds and about 10 minutes, between 10 seconds and about 20 minutes, between 10 seconds and about 30 minutes, between 10 seconds and about 40 minutes, between about 10 seconds and about 50 minutes, or between 10 seconds and about 1 hour) in which a shake flask containing the mammalian cell and liquid culture medium is removed from an incubator in order to remove the first volume of the first liquid culture medium and add the second volume of the second liquid culture medium.

In another exemplary method, a shake flask is first provided. A first liquid culture medium is added to the shake flask such that the medium occupies about 10% to about 40%, e.g., about 20% to about 30% (e.g., about 20% to about 22%, about 22% to about 24%, about 24% to about 26%, about 26% to about 28%, about 28% to about 30%, about 20% to about 25%, or about 25% to about 30%) of the volume of the shake flask. At least one mammalian cell and a plurality of microcarriers (a final concentration in the shake flask of about 1.0 g/L to about 15.0 g/L, e.g., a final concentration in the shake flask of between about 1.0 g/L to about 2.5 g/L, about 1.0 g/L to about 2.0 g/L, about 1.0 g/L to about 1.75 g/L, about 1.0 g/L to about 1.5 g/L, about 1.0 g/L to about 1.25 g/L, about 2.5 g/L to 5.0 g/L, about 5.0 g/L to about 7.5 g/L, about 7.5 g/L to about 10.0 g/L, about 10.0 g/L to about 12.5 g/L, about 12.5 g/L to about 15.0 g/L, about 1.0 g/L to about 5.0 g/L, about 5.0 g/L to about 10.0 g/L, about 10.0 g/L to about 15.0 g/L, about 2.5 g/L to about 3.5 g/L, about 3.0 g/L to about 4.0 g/L, about 4.0 g/L to about 5.0 g/L, about 5.0 g/L to about 6.0 g/L, about 6.0 g/L to about 7.0 g/L, about 7.0 g/L to about 8.0 g/L, about 8.0 g/L to about 9.0 g/L, about 9.0 g/L to about 10.0 g/L, about 10.0 g/L to about 11.0 g/L, about 11.0 g/L to about 12.0 g/L, about 12.0 g/L to about 13.0 g/L, about 13.0 g/L to about 14.0 g/L, or about 14.0 g/L to about 15.0 g/L) is added to the first liquid culture medium, i.e., either before the medium is added to the shake flask or afterward. As noted above, the addition of the liquid culture medium, a mammalian cell, and the liquid culture medium to the shake flask can occur in any order. Then, in a first time period, the shake flask is incubated at about 35° C. to about 39° C. (e.g., 35° C. to 37° C., 36° C. to 39° C., or 37° C. to 39° C.) with a rotary agitation of about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, or about 100 RPM to about 125 RPM). The cells can be incubated, for example, in an incubator, such as a shake incubator with throw (orbit) diameter from about 3 mm to about 50 mm. After about the first 48 to 96 hours of the first time period, in each subsequent 24-hour period, (i) continuously or periodically removing a first volume of the first liquid culture medium that is substantially free of micro carriers from the shake flask, wherein the first volume is about 10% to about 95% (e.g., about 10% to 20%, about 20% to about 30%, about 30% to about 40%, about 40% to about 50%, about 50% to about 60%, about 60% to about 70%, about 70% to about 80%, about 80% to about 95%, about 50% to about 95%, about 50% to about 90%, or about 60% to about 90%) of the volume of the first liquid culture medium; and (ii) adding to the shake flask a second volume of a second liquid culture medium, wherein the first and second volume are about equal. As noted above, the first and the second volumes are roughly equal, but can vary by a small amount, e.g., by up to about 10% when the first and second volumes are compared. Once the cell concentration reaches about target cell density (e.g., about $1.0 \times 10^6$ cells/mL, about $1.5 \times 10^6$ cells/mL, about $2.0 \times 10^6$ cells/mL, about $2.2 \times 10^6$ cells/mL, about $2.4 \times 10^6$ cells/mL, about $2.6 \times 10^6$ cells/mL, about $2.8 \times 10^6$ cells/mL, about $3.0 \times 10^6$ cells/mL, about $3.2 \times 10^6$ cells/mL, about $3.4 \times 10^6$ cells/mL, about $3.6 \times 10^6$ cells/mL, about $3.8 \times 10^6$ cells/mL, about $4.0 \times 10^6$ cells/mL, about $1.0 \times 10^6$ cells/mL to $4.0 \times 10^6$ cells/mL, about $2.0 \times 10^6$ cells/mL to about $4.0 \times 10^6$ cells/mL, about $2.0 \times 10^6$ cells/mL to about $4.0 \times 10^6$ cells/mL, about $4.0 \times 10^6$ cells/mL to about $6.0 \times 10^6$ cells/mL, about $6.0 \times 10^6$ cells/mL to about $8.0 \times 10^6$ cells/mL, about $8.0 \times 10^6$ cells/mL to about $10.0 \times 10^6$ cells/mL, about $10.0 \times 10^6$ cells/mL to about $15.0 \times 10^6$ cells/mL, about $15.0 \times 10^6$ to about $20.0 \times 10^6$ cells/mL, about $20.0 \times 10^6$ cells/mL to about $25.0 \times 10^6$ cells/mL, about $25.0 \times 10^6$ cells/mL to about $30.0 \times 10^6$ cells/mL, about $30.0 \times 10^6$ cells/mL to about $35.0 \times 10^6$ cells/mL, about $35.0 \times 10^6$ cells/mL to about $40.0 \times 10^6$ cells/mL, about $40.0 \times 10^6$ cells/mL to about $45.0 \times 10^6$ cells/mL, or about $45.0 \times 10^6$ cells/mL to about $50.0 \times 10^6$ cells/mL) the shake flask is incubated for a second time period of about 2 days to about 7 days (e.g., about 2 days to about 4 days, about 3 days to about 5 days, about 4 days to about 6 days, and about 5 days to about 7 days), at about 32° C. to about 39° C. (e.g., about 32° C. to about 35° C., about 32° C. to about 37° C., about 32° C. to about 38° C., about 34° C. to about 39° C., about 34° C. to about 37° C., about 35° C. to about 38° C., about 35° C. to about 39° C., about 36° C. to about 39° C., or about 37° C. to about 39° C.) with the rotary agitation, and in each 24-hour period, performing steps (i) and (ii) described above, where the first and second liquid culture media used in the first time period are of a substantially different type from those used in the second time period. Then, in a third period of time of greater than 2 days (e.g., 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days, greater than 100 days, 110 days, 120 days, 130 days, 140 days, 150 days, 160 days, 170 days, 180 days, 190 days, or 200 days, or at most 100 days, 125 days, 150 days, 175 days, 200 days, 225 days, 250 days, 275 days, or 300 days) incubating the shake flask at about 35° C. to about 39° C. (e.g., about 35° C. to about 37°, 36° C. to about 38° C., about 37° C. to about 39° C., or about 36° C. to about 39° C.) with the rotary agitation, and in each 24-hour period, performing steps (i) and (ii) listed above, where the first and second liquid culture media used in the second time period are of the same type as those used in the third time period.

Various non-limiting examples of each aspect of these culturing methods are described below. The exemplary aspects of the methods provided herein can be used in any combination without limitation.

Mammalian Cells

The methods provided herein can be used to culture a variety of different mammalian cells. In some examples of all the methods described herein, the mammalian is an adherent cell. Non-limiting examples of mammalian cells that can be cultured using any of the methods described herein include: Chinese hamster ovary (CHO) cells (e.g., CHO DG44 cells, CHO-K1s cells, Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. Additional mammalian cells that can be cultured using the methods described herein are known in the art. In non-limiting examples of any of the methods described herein, the concentration of mammalian cells present in the shake flask at the start of any of the culturing methods described herein is about $0.1 \times 10^6$ cells/mL to about $0.5 \times 10^6$ cells/mL (e.g., about $0.25 \times 10^6$ cells/mL to about $0.5 \times 10^6$ cells/mL).

The mammalian cell can contain a recombinant nucleic acid (e.g., a nucleic acid stably integrated in the mammalian cell's genome) that encodes a recombinant protein (e.g., a recombinant protein that is secreted by the mammalian cell). Non-limiting examples of recombinant nucleic acids that encode exemplary recombinant proteins are described below, as are recombinant proteins that are producible using the methods described herein. In some instances, the mammalian cell disposed in the shake flask for culturing is derived from a larger culture. For example, the mammalian cell in the shake flask can be derived from a large-scale bioreactor culture, i.e., a satellite culture can be prepared using any of the methods described herein.

Culture Media

Liquid culture media are known in the art. The first and/or second tissue culture medium (e.g., the first and second liquid culture medium used in the first time period or the second and third time periods) can be supplemented with a mammalian serum (e.g., fetal calf serum and bovine serum), and/or a growth hormone or growth factor (e.g., insulin, transferrin, and epidermal growth factor). Alternatively or in addition, the first and/or second liquid culture medium (e.g., the first and/or second liquid culture medium, e.g., the first and/or second liquid culture medium in the first time period or the second and third time periods) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The first and/or second liquid culture medium (e.g., the first and/or second liquid culture medium used in the first time period or the second and third time periods) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these or other additives.

Non-limiting examples of liquid culture media that are particularly useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different type of media. For example, in examples of the methods that include a first time period, a second time period, and a third time period, the first and second liquid culture medium used in the first time period are substantially different from the first and second liquid culture medium used in the second and third time period, and the first and second liquid culture medium used in the second and third time period are substantially the same. For example, the first and second liquid culture medium used in the first time period can be selected from the group of a serum-containing liquid culture medium or a liquid culture medium that contains a mammalian protein or a mammalian protein fraction or extract, and the first and second liquid culture medium used in the second and third time periods can be selected from the group of: an animal-derived component free liquid culture medium, a serum-free liquid culture medium, a chemically-defined liquid culture medium, and a protein-free liquid culture medium.

Microcarrier

In the methods described herein, a plurality of microcarriers is added to the liquid culture medium (e.g., the first and/or second liquid culture medium). For example, the plurality of microcarriers can have an average diameter of between about 20 μm to about 1 mm (e.g., between about 20 μm and about 250 μm, between about 100 μm to about 250 μm, between about 150 μm to about 250 μm, between about 250 μm and 500 μm, between about 200 μm to about 300 μm, between about 750 μm and 1 mm, between about 200 μm to about 800 μm, between about 200 μm and about 500 μm, between about 500 μm and about 800 μm), where the microcarriers have a surface that is permissive or promotes attachment of a mammalian cell (e.g., any of the mammalian cells described herein or known in the art). In some examples, a microcarrier can contain one or more pores (e.g., one or more pores with an average diameter of about 10 μm to about 100 μm (e.g., between about 10 μm and 20 μm, about 20 μm to about 30 μm, about 30 μm to about 40 μm, about 50 μm to about 60 μm, about 60 μm to about 70 μm, about 70 μm to about 80 μm, about 80 μm to about 90 μm, about 90 μm to about 100 μm, about 10 μm to about 45 μm, about 45 μm to about 80 μm, about 25 μM to about 35 μm, or about 30 μm)). In some embodiments, the surface of the plurality of microcarriers and/or the surface of the one or more pores in the plurality of microcarriers are coated with an agent that promotes the attachment of a mammalian cell to the microcarrier (e.g., attachment to the outer surface of the microcarriers and/or the surface of the pores in the microcarrier). Examples of such agents that can be used to promote the attachment of a mammalian cell include, but are not limited to, gelatin, collagen, poly-L-ornithine, polystyrene, and laminin.

In some examples, the microcarriers have an average effective cell binding surface area of between about 0.5 $m^2$/g dry and 2.0 $m^2$/g dry (e.g., between about 0.75 $m^2$/g dry and 1.25 $m^2$/dry, between about 1.0 $m^2$/g dry and about 1.5 $m^2$/dry, between about 1.25 $m^2$/dry and about 1.5 $m^2$/dry, about 1.5 $m^2$/dry and about 2.0 $m^2$/dry, and about 1.1 $m^2$/dry). In some examples, the microcarriers have an average volume of about 10 mL/g dry to about 70 mL/g dry (e.g., about 10 mL/g dry to about 20 mL/g dry, about 20 mL/g dry to about 30 mL/g dry, about 30 mL/g dry to about 40 mL/g dry, about 40 mL/g dry to about 50 mL/g dry, about 50 mL/g dry to about 60 mL/g dry, about 60 mL/g dry to about 70 mL/g dry, about 10 mL/g dry to about 40 mL/g dry, about 30 mL/g dry to about 40 mL/g dry, about 40 mL/g dry to about 70 mL/g dry, or about 40 mL/g dry). In some embodiments, the average relative density of the microcarriers is between 0.8 g/mL to about 1.2 g/mL (e.g., about 0.8 g/mL to about 0.9 g/mL, about 0.9 g/mL to about 1.0 g/mL, about 1.0 g/mL to about 1.1 g/mL, about 1.0 g/mL, about 1.1 g/mL to about 1.2 g/mL, about 0.95 g/mL to about 1.05 g/mL, or about 1.03 g/mL).

In some embodiments, the microcarriers are approximately spherical or ellipsoidal in shape. In other examples, the microcarriers have an abraded or rough surface with small protuberances that increase the total outer surface area of the microcarrier. In some embodiments, the microcarriers have a network structure. In some examples, the microcarriers are hygroscopic. In some examples, the microcarriers contain cellulose.

In some embodiments, the microcarriers have an outer surface and/or the microcarrier pores have a surface that is positively charged (e.g., positively charged due to the presence of N,N,-diethylaminoethyl groups). In some examples, the microcarriers have a network or net-like or web-like structure. The microcarriers can have an average charge density of about 0.5 me/g to about 2.5 me/g (e.g., about 0.5 me/g to about 1.5 meq/g, about 0.75 meq/g to about 1.25 meq/g, about 1.1 meq/g, about 1.5 meq/g to about 2.5 meq/g, about 1.5 meq/g to about 2.0 meq/g, about 1.8 meq/g, about 0.5 meq/g to about 1.0 meq/g, or about 1.0 meq/g to about 1.5 meq/g).

In some instances, the microcarrier can contain a natural polymer and/or a synthetic polymer. Non-limiting examples of synthetic polymers include polyethylene glycol (PEG), polyethylene oxide, polyethyleneimine, diethyleneglycol, triethyleneglycol, polyalkalene glycol, polyalkaline oxide, polyvinyl alcohol, sodium polyphosphate, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyglycerine, polyaspartamide, polyoxyethlene-polyoxypropylene copolymer (poloxamer), carboxylic acids (e.g., acrylic acid, methacrylic acid, itaconic acid, and maleic acid), polyoxyethylenes, polyethyleneoxide, unsaturated ethylenic monodicarboxylic acids, polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth)acrylamides), styrenes, polyalkalene glycol, polyalkaline oxide, and lactic acids. Non-limiting examples of natural polymers include cellulose, lecithin, and hyaluronic acid. A microcarrier can contain a mixture of different polymers (e.g., any combination of one or more polymers described herein or known in the art) in the same or different ratios. Any of the microcarriers described herein can contain a core containing one or more polymers (e.g., any of the polymers described herein or known in the art) and an outer layer that contains one or more different polymers (e.g., any of the polymers described herein or known in the art).

Non-limiting exemplary microcarriers that can be used in any of the methods described herein include CytoPore™ 1 and CytoPore™ 2 (available from GE Healthcare, Life Sciences, Piscataway, N.J.). Additional examples of microcarriers that can be used in any of the methods described herein are publicly available and known in the art.

Shake Flasks

The shake flask can be sterile and have a volume between about 125 mL to about 3 L (e.g., a 3-L, a 2.5-L, a 2-L, a 1.5-L, a 1-L, a 750-mL, a 500-mL, 400-mL, 300-mL, 250-mL, 200-mL, 150-mL, or 125-mL shake flask). The shake flask can have a volume, for example, of about 250 mL to about 300 mL, about 300 mL to about 400 mL, about 400 mL to about 500 mL, about 500 mL to about 600 mL, about 600 mL to about 700 mL, about 700 mL to about 800 mL, about 800 mL to about 900 mL, about 900 mL to about 1 L, about 100 mL to about 500 mL, about 500 mL to about 1 L, about 600 mL to about 1 L, about 1 L to about 3 L, about 1 L to about 2 L, about 2 L to about 3 L, about 1.5 L to about 2.5 L. The shake flask can include at least one gas permeable surface (e.g., at least one surface having a gas permeable membrane which may also act as a sterile barrier) and/or at least one vented cap. A shake flask may have on its outer surface a structure that allows the shake flask to be stably placed in a tissue culture incubator (e.g., a rotary incubator).

The interior surface of the shake flask may have at least one coating (e.g., at least one coating of gelatin, collagen, poly-L-ornithine, polystyrene, and laminin). Exemplary shake flasks that can be used in any of the methods described herein can be purchased from Corning Inc. (Tewsbury, Mass.), Presens (Brondby, Denmark), Nalge-Nunc International (Rochester, N.Y.). Exemplary shake flasks include T-flasks, Erlenmeyer flasks, or any art-recognized modified versions thereof. Additional examples of shake flasks (e.g., different shapes and dimensions of shake flasks) and interior surface coatings of shake flasks are known in the art and can be used in the present methods.

Agitation

The methods described herein involve the agitation of the culture containing the mammalian cell, a plurality of microcarriers, and the first and/or second liquid culture medium. The agitation can occur at a frequency of at about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, about 100 RPM to about 125 RPM, about 95 RPM to about 105 RPM, about 95 RPM to about 105 RPM, about 105 RPM to about 115 RPM, or about 115 RPM to about 125 RPM) (e.g., in an incubator, such as a shake incubator with throw (orbit) diameter from about 3 mm to about 50 mm).

As can be appreciated in the art, the level of agitation (e.g., RPM speed) can be varied depending upon the size and shape of the shake flask (e.g., the diameter of the shake flask), the throw (orbit) diameter of the incubator that is used to perform the agitation, and the average size, shape, density, and concentration of the plurality of microcarriers. For example, a smaller throw (orbit) diameter can require a higher level of agitation (e.g., a higher RPM speed), while a larger throw (orbit) diameter can require a lower level of agitation (e.g., a lower RPM speed) to achieve the conditions necessary to achieve optimal viable cell density and recombinant protein production. In another example, a shake flask having a larger diameter can require a lower RPM speed, while a shake flask having a smaller diameter can require a higher RPM speed to achieve the conditions necessary to achieve optimal viable cell density and recombinant protein production. The frequency of agitation can be varied depending on cell culture conditions, e.g., the concentration, density, and/or the size and/or surface shape of the microcarriers. As one skilled in the art can appreciate, if microcarriers present in the first and/or second liquid culture medium (e.g., the first and/or second liquid culture medium used in the first, second, and third time periods) have a high mass, a high density, a large outer surface area, or a relatively high velocity, the sheer forces generated by such microcarriers can have a negative impact on cell viability and recombinant protein production in the culture. In addition, those in the art can appreciate that the rate of agitation should be high enough to avoid substantial and/or undesirable settling of the microcarriers on the bottom of shake flask.

In some embodiments, the incubating is performed using a rotary incubator with a throw (orbit) diameter of between about 25 mm to about 50 mm and an agitation of between about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, about 100 RPM to about 125 RPM, or any of the RPM ranges described herein). In some embodiments, the incubating is performed using a rotary incubator with a throw (orbit) diameter of about 3 mm to about 25 mm and an agitation of about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, about 100 RPM to about 125 RPM, or any of the other RPM ranges described herein).

Agitation can be performed, e.g., using rotary circular shaking at a frequency of about 85 RPM to about 125 RPM (e.g., about 85 RPM to about 120 RPM, about 85 RPM to about 110 RPM, about 85 RPM to about 100 RPM, about 85 RPM to about 95 RPM, about 85 RPM to about 105 RPM, about 90 RPM to about 110 RPM, about 95 RPM to about 115 RPM, about 100 RPM to about 120 RPM, about 105 RPM to about 125 RPM, about 110 RPM to about 125 RPM, about 100 RPM to about 125 RPM, or any of the RPM ranges described herein). Alternatively or in addition, the shake flask can be agitated using a rotary ellipsoidal shaking, or horizontal and/or vertical tilting of the shake flask. The agitation can be performed continuously or periodically.

The agitation can be performed using a humidified atmosphere controlled incubator (e.g., at a humidity of about or greater than 20%, e.g., about or greater than 30%, 40%, 50%, 60%, 70%, 75%, 80%, 85%, 90%, or 95%, or a humidity of 100%) with a mechanical device that provides the agitation of one or more of the shake flasks containing the mammalian cell, the plurality of microcarriers, and a liquid culture medium (e.g., the first and/or second liquid culture medium, and the first and/or second liquid culture medium used in one or more of the first, second, and third time periods).

Reactor Angle

In some embodiments, the shake flask can be incubated at a reactor angle of about 25 degrees to about 90 degrees (e.g., about 25 degrees to about 55 degrees, about 25 degrees to about 90 degrees, about 35 degrees to about 90 degrees, about 45 degrees to about 90 degrees, or about 35 to about 65 degrees) from horizontal. For example, the shake flask can be placed at a reactor angle of about 60 degrees to about 85 degrees from horizontal, about 70 degrees to about 85 degrees from horizontal, about 25 degrees to about 60 degrees, about 25 degrees to about 55 degrees, about 30 degrees to about 55 degrees from horizontal, about 40 degrees to about 55 degrees horizontal, or about 40 degrees to about 50 degrees from horizontal. The shake flask may be placed at a reactor angle of about 45 degrees from horizontal to about 50 degrees from horizontal, or from about 40 degrees from horizontal to about 45 degrees from horizontal. The shake flask may be placed in a device that specifically and securely positions the shake flask at a reactor angle of about 25 degrees to about 90 degrees from horizontal (e.g., specifically positions the container at a reactor angle of about 25 degrees to about 90 degrees, about 35 degrees to about 90 degrees, about 45 degrees to about 90 degrees, about 35 degrees to about 65 degrees, or about 40 degrees to about 55 degrees from horizontal). The positioning of the shake flask can be performed using any means known in the art, e.g., through the use of a brace or a locking element.

Temperature

The culturing methods described herein can be performed at a temperature of 32° C. to about 39° C., e.g., about 32° C. to about 37° C. For example, in some methods the shake flask can be incubated at a temperature of about 37° C. from the beginning to the end of the culture run. Some examples of the methods described herein include a first time period during which the shake flask is incubated at a temperature of about 35° C. to about 39° C., e.g., about 35° C. to about 37° C., a second time period during which the shake flask is incubated at about 32° C. to about 39° C., e.g., about 32° C. to about 37° C., and third time period during which the shake flask is incubated at about 35° C. to about 39° C., e.g., about 35° C. to about 37° C. Skilled practitioners will appreciate that the temperature can be changed at specific time point(s) in the culturing method (e.g., during one or more of the first time period, the second time period, and the third time period), e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the shake flask with the mammalian cell) or at any time point within the first, second, and/or third time periods described herein. For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.).

Culture Medium Removal and Replacement

The methods described herein include removing from the shake flask a first volume of a first liquid culture medium (e.g., containing any concentration of mammalian cells and any recombinant protein, e.g., a first volume of a first liquid culture medium that is substantially free of cells and/or microcarriers), and adding to the shake flask a second volume of a second liquid culture medium, wherein the first volume and the second volume are about equal. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the shake flask or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, five times a day, or more than five times a day), or any combination thereof. Where performed periodically, the volume that is removed or replaced (e.g., within about a 24-hour period, within an incremental time period of about 0.1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the shake flask or the first liquid culture medium volume. The first volume of the first liquid culture medium removed and the second volume of the second liquid culture medium added can in some instances be held approximately the same over each 24-hour period (or, alternatively, an incremental time period of about 0.1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 0.1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the shake flask volume or the first liquid culture medium volume to about 25% to about 150% of the shake flask volume or the first liquid culture medium volume.

In some examples of the methods described herein, after the first 48 to 96 hours of the culture period, in each 24-hour period, the first volume of the first liquid culture medium removed (e.g., in the first, second, and/or third time period) and the second volume of the second liquid culture medium added (e.g., in the first, second, and/or third time period) is about 10% to about 95% (e.g., about 10% to about 20%, about 10% to about 20%, about 20% to about 30%, about 30% to about 40%, about 40% to about 50%, about 50% to about 60%, about 60% to about 70%, about 70% to about 80%, about 80% to about 90%, about 85% to about 95%, about 60% to about 80%, or about 70%) of the volume of the first liquid culture medium.

Skilled practitioners will appreciate that the first liquid culture medium and the second liquid culture medium can be the same type of media. In other instances, the first liquid culture medium and the second liquid culture medium can be substantially different. In some embodiments that include a first time period, second time period, and third time period, the first and second liquid culture media used in the first time period are a substantially different type of media compared to the first and second liquid culture media used in the second time period, and the first and second liquid culture media used in the second time period are the same type of media compared to the first and second liquid culture media used in the third time period. As can be recognized in the art, the first and second liquid culture media used in the first time period do not have to be exactly the same (as long as they are the same type of culture medium); any of the first and second liquid culture media used in the second time period and/or third time period do not have to be exactly the same (again, as long as they are the same type of medium and a substantially different media type from the first and second liquid culture medium used in the first time period).

The first volume of the first liquid culture medium can be removed, e.g., by centrifuging (e.g., slow-speed swinging bucket centrifugation) the shake flask or using any other automated system, and removing the first volume of the first liquid culture (e.g., a first volume of the first liquid culture medium that is substantially free of cells and/or microcarriers) from the supernatant. Alternatively or in addition, the first volume of the first liquid culture medium can be removed by seeping or gravity flow of the first volume of the first liquid culture medium through a sterile membrane with a molecular weight cut-off that excludes the mammalian cell and/or microcarriers. Alternatively or in addition, the first volume of the first liquid culture medium can be removed by stopping or significantly decreasing the rate of agitation for a period of at least 10 seconds (e.g., at least 30 seconds, 40 seconds, 50 seconds, 1 minutes, 2 minutes, 3 minutes, 4 minutes, 5 minutes, 10 minutes, 15 minutes, 20 minutes, 25 minutes, 30 minutes, 40 minutes, 50 minutes, or 1 hour) and removing or aspirating the first volume of the first liquid culture medium from the top of the shake flask (e.g., removal from a part of the liquid culture medium where the microcarriers have not settled due to gravitational force). The shake flask may be placed in an incubator during the period in which the agitation is ceased. One skilled in the art will understand that the shake flask may be removed from the incubator for a short period of time (e.g., less than 30 minutes, 20 minutes, 15 minutes, 10 minutes, 8 minutes, 6 minutes, 4 minutes, 2 minutes, or 1 minute) while the first liquid culture medium is removed from the shake flask.

The second volume of the second liquid culture medium can be added to the first liquid culture medium, e.g., by perfusion pump. The second liquid culture medium can be added to the first liquid culture medium manually (e.g., by pipetting the second volume of the second liquid culture medium directly onto the first liquid culture medium) or in an automated fashion.

In some instances, removing the first volume of the first liquid culture medium (e.g., a first volume of the first liquid culture medium that is substantially free of mammalian cells and/or microcarriers) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the shake flask with a mammalian cell.

$CO_2$

Methods described herein can further include incubating the shake flask in an atmosphere containing at most or about 1% to 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$). Moreover, any of the methods described herein can include incubating the shake flask in a humidified atmosphere (e.g., at least or about 20%, 30%, 40%, 50%, 60%, 70%, 85%, 80%, 85%, 90%, or at least or about 95% humidity, or about 100% humidity).

Exemplary Devices

Non-limiting examples of devices that can be used to perform the culturing methods described herein include: Appropriate Technical Resources (Maryland, USA) distributes INFORS Multiron shake incubator (INFORS; Basel, Switzerland), and Kuhner shake incubator (Kuhner AG; Basel, Switzerland). Non-limiting examples of devices that can be used to perform the culturing methods include a rotary incubator with a throw (orbit) diameter of between about 3 mm to about 50 mm (e.g., between about 1 mm and about 25 mm, or between about 25 mm and about 50 mm). Additional examples of shake incubators are known in the art.

Methods of Producing a Recombinant Protein

Also provided herein are methods of producing a recombinant protein, which include culturing a cell that is capable of producing the recombinant protein using a method described herein. Following performance of the method, the recombinant protein can be recovered from the mammalian cell (e.g., the mammalian cell that is attached to the microcarrier) and/or from the first or second culture medium (e.g., the first and/or second liquid culture medium used in one or more of the first, second, and third time periods). In some embodiments, the recombinant protein is recovered from the first and/or second liquid culture medium at any given time point during the culturing method (e.g., recovered from the first and/or second liquid culture medium on one or more of days 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of culture, or after more than 100 days of culture, or at any time point during one or more of the first time period, the second time period, and the third time period).

Skilled practitioners will appreciate that any of the various culture parameters (e.g., shake flasks, volumes, rates or frequencies of replacing culture volumes, agitation frequencies, type of microcarrier, temperatures, media, and $CO_2$ concentrations) can be used in any combination to perform these methods. Further, any of the mammalian cells described herein or known in the art can be used to produce a recombinant protein.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection), while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant protein is a secreted protein and is released by the mammalian cell into the extracellular medium (e.g., the first and/or second liquid culture medium, e.g., the first and/or second liquid culture medium used in one or more of the first, second, and third time periods). For example, a nucleic acid sequence encoding a soluble recombinant protein can contain a sequence that encodes a secretion signal peptide at the N- or C-terminus of the recombinant protein, which is cleaved by an enzyme present in the mammalian cell, and subsequently released into the extracellular medium (e.g., the first and/or second liquid culture medium, or the first and/or second liquid culture medium used in one or more of the first, second, and third time periods). In other instances, the recombinant protein is a soluble protein that is not secreted, and the recombinant protein is recovered from within the mammalian cell (e.g., from within the mammalian cell that is attached to the microcarrier, e.g., recovered from the mammalian cell attached to the microcarrier after it has been unattached from the microcarrier).

Non-limiting examples of recombinant proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). In some embodiments, the recombinant protein is an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies that can be produced by the methods described herein are known in the art. Additional non-limiting examples of recombinant proteins that can be produced by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, and alteplase.

A secreted, soluble recombinant protein can be recovered from the liquid culture medium (e.g., the first and/or second liquid culture medium, e.g., the first and/or second liquid culture medium used in one or more of the first, second, and third time periods) by removing or otherwise physically separating the liquid culture medium from microcarriers and their associated mammalian cells. A variety of different methods for removing liquid culture medium from mammalian cells are known in the art, including, for example, centrifugation, filtration, pipetting, and/or aspiration. The secreted recombinant protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

To recover an intracellular recombinant protein, the mammalian cell (e.g., the mammalian cell attached to the microcarrier) can be lysed. In some examples, the mammalian cell is released from the surface of the microcarrier before it is lysed. Methods for releasing an adherent cell from the surface of a microcarrier are known in the art (e.g., vortexing or agitation). In other examples, the mammalian cell is lysed while it is still attached to the microcarrier (e.g., using any of the exemplary methods listed below).

A wide variety of methods for lysing mammalian cells are known in the art, including, for example, sonication and/or detergent, enzymatic, and/or chemical lysis. A recombinant protein can be purified from a mammalian cell lysate using a variety of biochemical methods known in the art, typically starting with a step of centrifugation to remove the cellular debris, and then one or more additional steps (e.g., one or more types of chromatography (e.g., affinity chromatography, molecular sieve chromatography, cation exchange chromatography, or anion exchange chromatography) and/or filtration (e.g., molecular weight cut-off filtration)).

In some embodiments, the recovered recombinant protein is at least or about 50% pure by weight, e.g., at least or about 55% pure by weight, at least 60% pure by weight, at least 65% pure by weight, at least 70% pure by weight, at least 75% pure by weight, at least 80% pure by weight, at least 85% pure by weight, at least 90% pure by weight, at least 95% pure by weight, at least 96% pure by weight, at least 97% pure by weight, at least 98% pure by weight, or at least or about 99% pure by weight, or greater than 99% pure by weight.

In some embodiments, the recovered recombinant protein is a recombinant human protein that has one or more different biophysical properties as compared to the same native protein in a human (e.g., differences in the type or amount of glycosylation, differences in phosphorylation, differences in acylation, differences in metallation or metal stoichiometry, and/or differences in cofactor binding).

Also provided herein is a recombinant protein produced by any of the methods described herein.

Methods for Testing a Manufacturing Process

Also provided herein are methods for testing a manufacturing process for making a recombinant protein. These methods include performing a method of producing a recombinant protein described herein and, during the method and/or afterward, detecting or measuring at least one (e.g., two, three, four, five, six, seven, eight, nine, ten, or eleven) culture readout (e.g., the recombinant protein in the cell or in the first and/or second culture medium (e.g., the first and/or second liquid culture medium used in one or more of the first, second, and third time periods), glucose consumption, viable cell concentration, lactate production, volumetric productivity, lactate yield from glucose, glutamine concentration, glutamate concentration, pH of culture medium, partial pressure or concentration of dissolved $CO_2$, concentration or partial pressure of dissolved $O_2$, metabolite mass transfer, and metabolite mass balance); and comparing the at least one culture readout to a reference level of the at least one (e.g., two, three, four, five, six, seven, eight, nine, ten, or eleven) culture readout (e.g., a reference level of the recombinant protein in the cell or in the first and/or second culture medium (e.g., the first and/or second liquid culture medium used in one or more of the first, second, and third time periods), glucose consumption, viable cell concentration, lactate production, volumetric productivity, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance).

Skilled practitioners will appreciate that any of the various culture parameters (e.g., shake flasks, volumes, type of microcarrier, rates or frequencies of replacing culture volumes, agitation frequencies, temperatures, media, and $CO_2$ exposure) described herein can be used in any combination to perform these methods. Further, any of the mammalian cells described herein or known in the art can be used in the methods.

The reference level of the at least one culture readout (e.g., level of recombinant protein in the cell or in the first and/or second culture medium (e.g., the first and/or second liquid culture medium used in one or more of the first, second, and third time periods), glucose consumption, viable cell concentration, lactate production, volumetric productivity, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance) can be a level produced using a different culturing method, e.g., a culturing method that utilizes at least one different culture parameter (e.g., a different first and/or second liquid culture medium (e.g., a different first and/or second liquid culture medium in one or more of the first, second, or third time periods), a different mammalian cell, a different frequency and/or type of agitation, a different type or concentration of microcarrier, a different batch re-feed or perfusion rate (e.g., 10% to 95% of the shake flask volume or the first liquid culture medium volume over each 24-hour time period after the first 48 to 96 hours of culture), and any of the other culture parameters described herein).

The methods described herein can be used to test the effect of any component or feature of a manufacturing process. For example, the method described herein can be used to test the effect of different raw materials, microcarriers, agitation levels, shake flasks, anti-clumping agents, culture media (e.g., chemically-defined culture media), or nutrient elements or compounds on the at least one culture readout (e.g., any of the culture readouts described herein, e.g., the effect on recombinant protein production and/or mammalian cell growth). For example, provided herein are methods of testing the efficacy of a first or second liquid culture medium, a raw ingredient or supplement present in a first or second liquid culture medium, or a source of a mammalian cell for use in a method of producing a recombinant protein that include providing a shake flask containing a mammalian cell disposed in a first liquid culture medium, wherein the first liquid culture medium occupies about 10% to about 40%, e.g., about 20% to about 30% of the volume of the shake flask, and contains a plurality of microcarriers at a concentration of about 1.0 g/L to about 15.0 g/L; incubating the shake flask for a period of time at about 31° C. to about 40° C., e.g., about 32° C. to about 37° C., and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting or determining at least one culture readout (e.g., any of the culture readouts described herein, e.g., the recombinant protein in the cell or in the first and/or second culture medium); comparing the at least one culture readout to a reference level of the at least one culture readout (e.g., any of the culture readouts described herein, e.g., recombinant protein in the cell or in the first and/or second liquid culture medium) produced by a different culturing method that uses one or more of a different first or second liquid culture medium, a different raw ingredient or supplement present in the first or second liquid culture medium, or a different source of a mammalian cell; and identifying the first or second liquid culture medium, the raw ingredient or supplement present in the first or second liquid culture medium, or the source of the mammalian cell that is associated with beneficial change (e.g., increase or decrease) in the at least one culture readout (e.g., an increased amount of recombinant protein) as compared to the reference level as being efficacious for use in a method of producing a recombinant protein. For example, an increase in recombinant protein level, an increase in viable cell concentration, an increase in volumetric productivity, and an increase in glucose consumption compared to the reference level indicates that the first or second liquid culture medium, the raw ingredient or supplement present in a first or second liquid culture medium, or the source of the mammalian cell are efficacious for use in a method of producing a recombinant protein.

The methods described herein can also be used to test the effect of changing any of the various cell culture parameters described herein or known in the art (e.g., the volume or shape of a shake flask, the frequency of agitation, the sheer force generated by the plurality of microcarriers in the first and/or second liquid culture medium, the culture seeding density, the pH of the first and/or second liquid culture medium (e.g., the pH of the first and/or second liquid culture medium used in one or more of the first, second, or third time periods), dissolved $O_2$ concentration or partial pressure, the inner surface coating of the shake flask, one or more of the concentration, size, shape, surface properties, density, and porosity of the microcarriers, the various ingredients within a liquid culture media (e.g., the first and/or second liquid culture media, e.g., the first and/or second liquid culture medium used in one or more of the first, second, and third time periods), the amount and/or type of agitation, the mammalian cell type or line, dissolved $CO_2$ concentration or partial pressure, the temperature, the volume of liquid culture medium (e.g., the volume of the first and/or second liquid culture media), and/or the rate or frequency of removing the first volume of the first liquid culture medium and adding the second volume of the second liquid culture medium to the first culture medium (e.g., the rate or frequency of removing the first volume of the first culture medium and adding the second volume of the second liquid culture medium in one or more of the first, second, and third time periods). The methods can also be used to test the quality of water used to prepare the liquid culture medium (e.g., the first and/or second liquid culture medium, e.g., the first and/or second liquid culture medium used in one or more of the first, second, and third time periods) and/or the effect of different trace metals in the liquid culture medium on at least one culture readout on at least one culture readout (e.g., any of the culture readouts described herein, e.g., the effect on recombinant protein production and/or mammalian cell growth). The methods can also be used to test the effect of a growth factor or growth hormone (e.g., the effect of the presence of a growth factor or growth hormone in the first time period) on at least one culture readout (e.g., any of the culture readouts described herein, e.g., the effect on recombinant protein production and/or mammalian cell growth). The method can also be used to test filtration processes and filters used to prepare the first and/or second liquid culture medium (e.g., the first and/or second liquid culture medium used in one or more of the first, second, and third time periods). The method can also be used to test liquid culture medium stability and the effect of a liquid culture medium on at least one culture readout (e.g., any of the culture readouts described herein, e.g., the effect on recombinant protein production and/or mammalian cell growth). The method can also be used to screen various recombinant cells lines and cell banks for their ability to produce a desired recombinant protein (e.g., a desired secreted therapeutic protein). As noted herein, the method can also be used to screen any cell culture process parameter, including but not limited to, the type and frequency of agitation, sheer force generated by the microcarriers, perfusion rate and volume, culture seeding density, and others.

The method described herein can also be used to test for the presence of a contaminant in a first or second liquid culture medium, a raw material used to generate a first or second liquid culture medium, or a source of a mammalian cell. For example, provided herein are methods of testing for the presence of a contaminant in a first or second liquid culture medium, raw materials used to generate a first or second liquid culture medium, or a source of a mammalian cell that include providing a shake flask containing a mammalian cell disposed in a first liquid culture medium, wherein the first liquid culture medium occupies about 10% to about 40%, e.g., about 20% to about 30% of the volume of the shake flask, and contains a plurality of microcarriers at a concentration of about 1.0 g/L to about 15.0 g/L; incubating the shake flask for a period of time at about 32° C. to about 39° C., e.g., about 32° C. to about 37° C., and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting or determining at least one culture readout (e.g., any of the culture readouts described herein, e.g., the recombinant protein in the cell or in the first and/or second culture medium); comparing the at least one culture readout to a reference level of the at least one culture readout (e.g., any of the culture readouts described herein, e.g., amount of recombinant protein present in the cell or in the first and/or second culture medium) produced by a different culturing method that uses one or more of a different first or second liquid culture medium, different raw materials to generate the first or second liquid culture medium, or a different source of the mammalian cell; and identifying the first or second liquid culture medium, the raw materials used to generate the first or second liquid culture medium, or the source of a mammalian cell as containing a contaminant when the level of the at least one culture parameter is detrimentally changed (e.g., increased or decreased) compared to the reference level. For example, a decrease in recombinant protein production (e.g., a decrease in recombinant protein in the cell or in the first and/or second culture medium), volumetric productivity, or viable cell concentration as compared to the reference level is a detrimental change that indicates the presence of a contaminant in the first or second liquid culture medium, a raw material used to generate the first or second liquid culture medium, or the source of the mammalian cell. Some methods further include one or more assays to determine the identity of the contaminant present in the first or second liquid culture medium, the raw material used to generate the first or second liquid culture medium, or the source of the mammalian cell. The contaminant can be a biological contaminant (e.g., a mycobacterium, a fungus, a bacterium, a virus, or an undesired mammalian cell). The contaminant can be an inorganic contaminant. The contaminant can also be a physically uncharacterized substance.

The methods can used to conduct high throughput cell culture experiments to perform a design-of-experiment (DOE) or a quality-by-design (QBD) optimization of cell culturing methods. For example, provided herein are methods of optimizing a manufacturing process of producing a recombinant protein that include providing a shake flask containing a mammalian cell disposed in a first liquid culture medium, wherein the first liquid culture medium occupies about 10% to about 40%, e.g., about 20% to about 30%, of the volume of the shake flask, and contains a plurality of microcarriers at a concentration of about 1.0 g/L to about 15.0 g/L; incubating the shake flask for a period of time at about 32° C. to about 39° C., e.g., about 32° C. to about 37° C., and with a rotary agitation of about 85 revolutions per minute (RPM) to about 125 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting at least one culture readout (e.g., any of the culture readouts described herein, e.g., amount of recombinant protein in the cell or in the first and/or second culture medium); comparing the at least one culture readout to a reference level of the at least one culture readout (e.g., any of the culture readouts described herein, e.g., amount of recombinant protein present in the cell or in the first and/or second culture medium) produced by a different culturing method; and identifying and removing or altering in a manufacturing process any culture components or parameters that are associated with a detrimental change (e.g., increase or decrease) in the at least one culture readout (e.g., any of the culture readouts described herein, e.g., amount of recombinant protein produced) as compared to the reference level of the at least one culture readout (e.g, any of the culture readouts described herein, e.g., recombinant protein produced), or identifying and adding to a manufacturing process any culture components or parameters that are associated with a beneficial change (e.g., increase or decrease) in the at least one culture readout (e.g., any of the culture readouts described herein, e.g., amount of recombinant protein produced) as compared to the reference level of the at least one culture readout (e.g., any of the culture readouts described herein, e.g., recombinant protein produced). For example, an increase in the amount of recombinant protein produced, volumetric productivity, or viable cell concentration is a beneficial change in a culture readout, and a decrease in the amount of recombinant protein produced, volumetric productivity, or viable cell concentration is a detrimental change in a culture readout. In some instances, the method is used to identify in a high throughput fashion, optimized cell culture conditions that can be used for up-scaled (e.g., bioreactor) production of a recombinant protein.

In any of the methods described in this section, the reference level of the at least one culture readout can be from a larger-scale culture (e.g., a perfusion bioreactor, e.g., a 2000-L perfusion bioreactor, 40-L perfusion bioreactor, or a 12-L perfusion bioreactor). In some embodiments of any of the methods described in this section, the mammalian cell is cultured in a shake flask using any of the methods described herein over the same time period that a larger-scale culture is performed (cultured in parallel). For example, the inoculum used to inoculate the shake flask in any of the methods described herein is also used to inoculate a larger-scale perfusion bioreactor at approximately the same time.

In one embodiment, the inoculum that is used to seed the shake flask is obtained from a larger-scale culture (e.g., a larger-scale perfusion bioreactor). For example, an aliquot from a larger-scale culture (e.g., an aliquot from a larger-scale perfusion bioreactor) is removed from the larger-scale culture at any time point (e.g., removed during the growth phase, the transition phase, or the harvest phase described herein) and used to inoculate the shake flask (e.g., used to start a satellite shake flask culture). An aliquot can be removed from the larger-scale culture during the growth phrase and used to inoculate or seed a shake flask containing a liquid culture medium and a plurality of microcarriers (e.g., as described herein), and the shake flask is then incubated under conditions that replicate or are similar to the growth phase conditions employed in the larger-scale culture. An aliquot can alternatively, or additionally, be removed from the larger-scale culture during the transition phase and used to inoculate or seed a shake flask containing a liquid culture medium and a plurality of microcarriers (e.g., as described herein), and the shake flask is then incubated under conditions that replicate or are similar to the transition phase conditions employed in the larger-scale culture. An aliquot can alternatively, or additionally, be removed from the larger-scale culture during the harvest phase and used to inoculate or seed a shake flask containing a liquid culture medium and a plurality of microcarriers (e.g., as described herein), and the shake flask is then incubated under conditions that replicate or are similar to the harvest phase conditions employed in the larger-scale culture. In any of these methods, one or more culture parameters can be altered in the methods used to culture the mammalian cell in the shake flask (as compared to the culture parameters or components used to culture the mammalian cell in the larger-scale culture), at least one culture readout is measured, and the at least one culture readout is compared to the at least one culture readout determined for the larger-scale culture. As can be appreciated by those in the art, these methods can be used to test the effect of a specific culture parameter or component on at least one culture readout during one or more specific phases in the culturing process (e.g., the effect of one or more culture parameters and/or culture component(s) on at least one culture readout during the growth, transition, and/or harvest phase).

In certain embodiment, these methods can also be performed to determine whether a contaminant is present in the larger-scale bioreactor, by determining or detecting at least one culture readout in the shake flask culture, comparing the at least one culture readout to a reference level of the at least one culture readout (e.g., a level of the at least one culture readout from a culture that is substantially free of contamination), and identifying the larger-scale bioreactor as containing a contaminant when the at least one culture readout in the shake flask culture as compared to the reference level of the at least one culture readout indicates that a contaminant is present in the shake flask. The contaminant can be, for example, a biological contaminant, such as a virus, a fungus, an undesired mammalian cell, or a bacterium, such as a mycobacterium. The contaminant can be, for example, a vesivirus.

EXAMPLES

The invention is further described in the following examples, which do not limit the scope of the invention described in the claims.

Example 1. Exemplary Culture Methods Using a Shake Flask and Microcarriers

The human recombinant form of human alpha-galactosidase can be produced using established recombinant engineering techniques in a CHO cell line. The current manufacturing production of recombinant human alpha-galactosidase utilizes a 2000-L continuous perfusion microcarrier cell culture process technology. Typically the production cell culture process includes three phases: a growth, transition, and harvest phase. There is a demand for a high throughput cell culture process system that would accurately model the cell culture process conditions achieved in a 2000-L bioreactor cell culture process run. Described in this Example is a shake flask microcarrier batch re-feed cell culture process that simulates the recombinant human alpha-galactosidase 2000-L bioreactor perfusion cell culture process.

Materials and Methods
Recombinant Human Alpha-Galactosidase Cell Culture

The cells used for the experiments are stably transformed with a nucleic acid that encodes a secreted form of human recombinant alpha-galactosidase. A growth medium (925 medium with 10% DBS, pH 7.3, and 0.1% Pluronic F-68) was used during the cell bank culture expansion process.

Equipment
A Multitron Shaker incubator (Appropriate Technical Resources, Inc., Model number AG CH-4103) was used to culture the cells. A Beckman Coulter Vi-Cell XR Cell Viability Analyzer (Model number XR, Cat #731050) was used to measure the viable cell density and percentage of viable cells in the culture.

Methods

The inoculum used for the exemplary shake flask microcarrier batch re-feed cell culture process runs was generated from a seed culture expansion of a thawed vial of recombinant human alpha-galactosidase-producing CHO cells. After five days of expansion of the thawed cells in 925 medium with 10% DBS, pH 7.3, and 0.1% Pluronic F-68, the seed culture was used to inoculate a shake flask (at a final concentration of $0.25 \times 10^6$ viable cells/mL in the shake flask) containing a sterilized microcarrier slurry (CytoPore2, GE Healthcare, Piscataway, N.J.; final concentration of 1.5 g/L; average size 200-280 μm; average pore size 30 μm) and growth medium (925 medium with 6% DBS, pH 7.0, and 0.1% Pluronic F-68), which initiates the growth phase of the cell culture. The cultures were maintained at 37° C. or 36° C., 95 RPM, 80% relative humidity, and 5% $CO_2$. When the culture reached a target cell density of between $2.5 \times 10^6$ to $3.0 \times 10^6$ viable cells/mL, the transition phase was initiated by changing the liquid culture medium to a different production liquid culture medium (925 medium, pH 6.85-7.05, and 0.1% Pluronic F-68) and shifting the temperature to 32° C. After 5 days of transition phase, the temperature was shifted back to 37° C. or 36° C., and the cultures were maintained with production liquid culture medium. Medium exchange was initiated on the third day of the growth phase and was continued until the end of culture, with a daily batch re-feed exchange of 70% of the initial volume of the liquid culture medium present in the shake flask at the start of the culture. On each day, starting on the third day of the growth phase, medium exchange was performed by briefly stopping the agitation of the shake flask, allowing the microcarriers to settle to the bottom of the shake flask in a biosafety hood. In some instances, the shake flask was placed in a rack which positions the shake flask at a 45 degree angle with respect to the horizon or the benchtop while the microcarriers settled to the bottom of the shake flask in order to improve medium exchange. A non-limiting example of such a rack is shown in FIG. 1. After the microcarriers have settled to the bottom of the shake flask, a volume of liquid culture medium that is 70% of the initial volume of the liquid culture medium present in the shake flask is removed from the shake flask, and then shortly thereafter, a volume of liquid culture medium that is substantially the same volume as the volume of liquid culture medium removed is added to the shake flask. On pre-determined culture days, the following culture parameters were analyzed: viable and suspension cell density and the percentage of viable of cells, $pCO_2$, $pO_2$, pH, glucose and lactate concentration, and glutamine and glutamate concentration. Titer samples were collected and kept at −20° C. until the assay was performed to measure the recombinant human alpha-galactosidase activity. A total of two full cell culture process runs were performed using a triplicate set of flasks for each run. The average and standard deviation of the resulting data were calculated and are shown in each of FIGS. 2-6.

Results and Discussion
Growth Phase Duration and Transition Density

Cell culture performance during the growth phase is critical to the successful production of a recombinant protein. Table 1 provides a summary of the growth phase duration and viable cell density achieved at the end of the growth phase of two shake flask microcarrier batch re-feed cell process runs that were started with the inoculum described above. The growth phase duration was consistent between the two cell culture process runs, with a viable cell density of $2.5 \times 10^6$ cells/mL to $3.0 \times 10^6$ cells/mL (an exemplary target viable cell density range for beginning the transition phase) achieved after 8 days of growth.

TABLE 1

Summary of growth phase duration and viable cell density at the beginning of the transition phase for two recombinant human alpha-galactosidase shake flask microcarrier batch re-feed cell culture process runs.

| Experiment | Growth Duration | Transition Density (E6 viable cells/mL) | Replicate |
|---|---|---|---|
| CCCD-HT-03 | 192 hours (G8) | 2.6 +/− 0.5 | n = 3 |
| CCCD-HT-11 | 195 hours (G8) | 2.9 +/− 0.4 | n = 3 |

Cell Culture Growth

Figure 2:
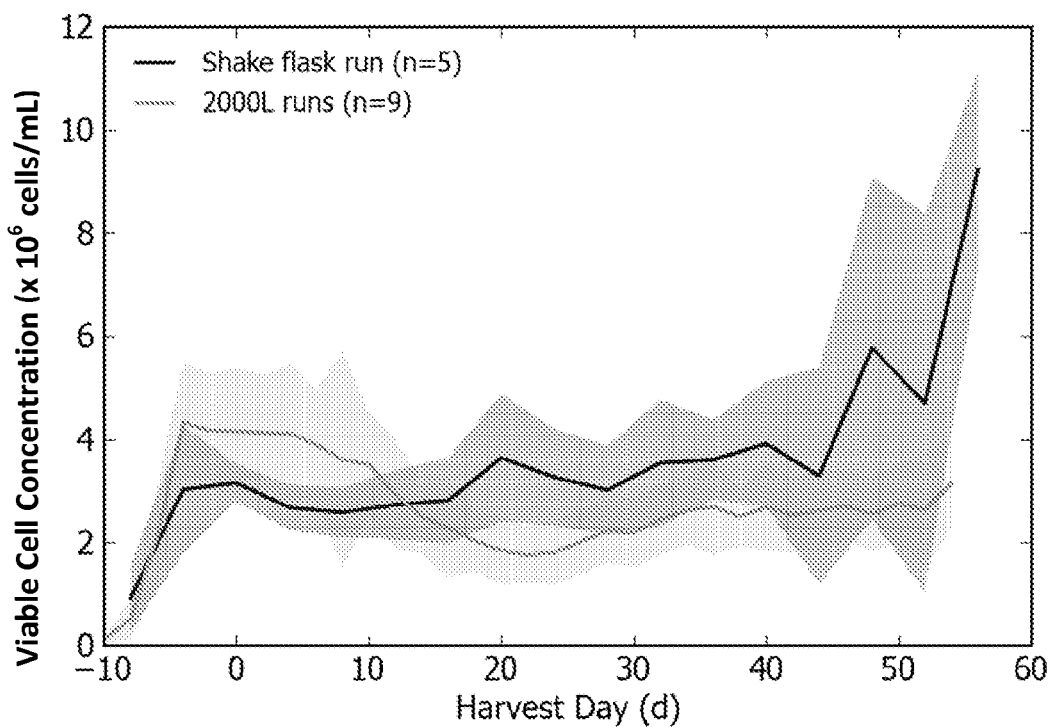
FIG. 2 is a graph showing the average viable cell concentration over time in recombinant human alpha-galactosidase shake flask microcarrier batch re-feed cell culture process runs (n=5) and 2000-L bioreactor cell culture process runs (n=9). The shaded areas represent the standard deviation of the data.
Figure 3:
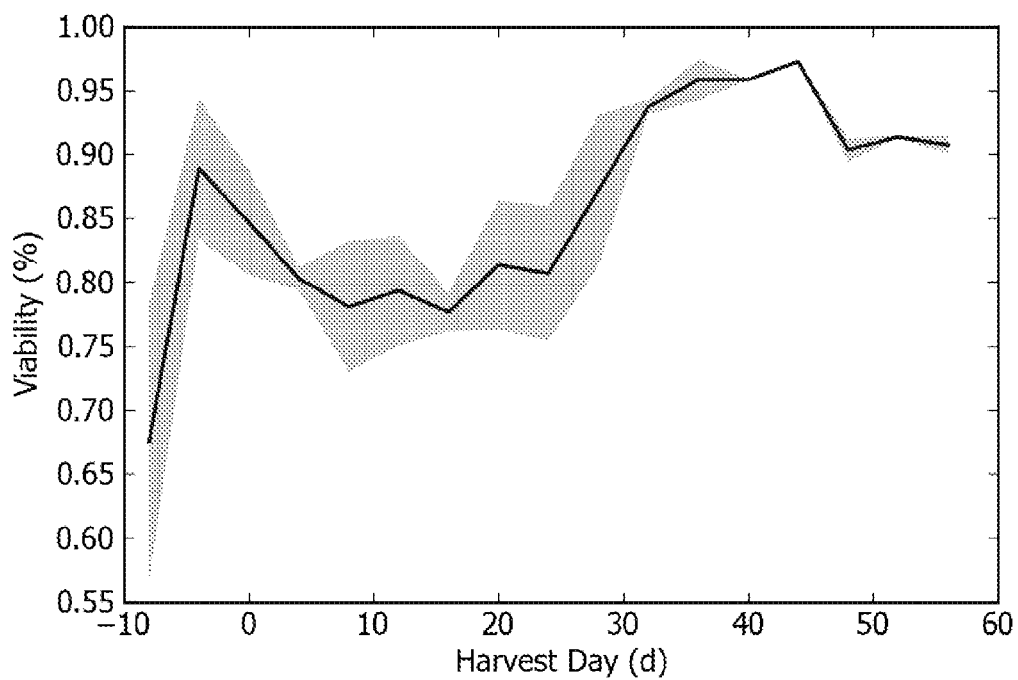
FIG. 3 is a graph showing the average percentage of viable cells over time in recombinant human alpha-galactosidase shake flask microcarrier batch re-feed cell culture process runs (n=5). The shaded area represents the standard deviation of the data.

The growth and health performance of the cell culture were monitored through several difference metrics. Culture growth was tracked by the measurement of the viable cell concentration (FIG. 2). The resulting data show a consistent increase in cell concentration through growth phase and early transition phase, and the achievement of a maximum viable cell concentration of approximately $3.0 \times 10^6$ cells/mL at the end of the growth phase. As the culture is adapting to serum-free medium (starting at the beginning of transition phase through the harvest phase), there is a slight decrease in viable cell concentration during the early harvest phase. The culture thereafter stabilizes and maintains a viable cell concentration of between $2.0 \times 10^6$ and $4.0 \times 10^6$ for most of the harvest phase, with further increase in viable cell density during the late harvest phase. Throughout most of harvest phase, the percentage of viable cells is greater than 80% (FIG. 3).

Figure 4:
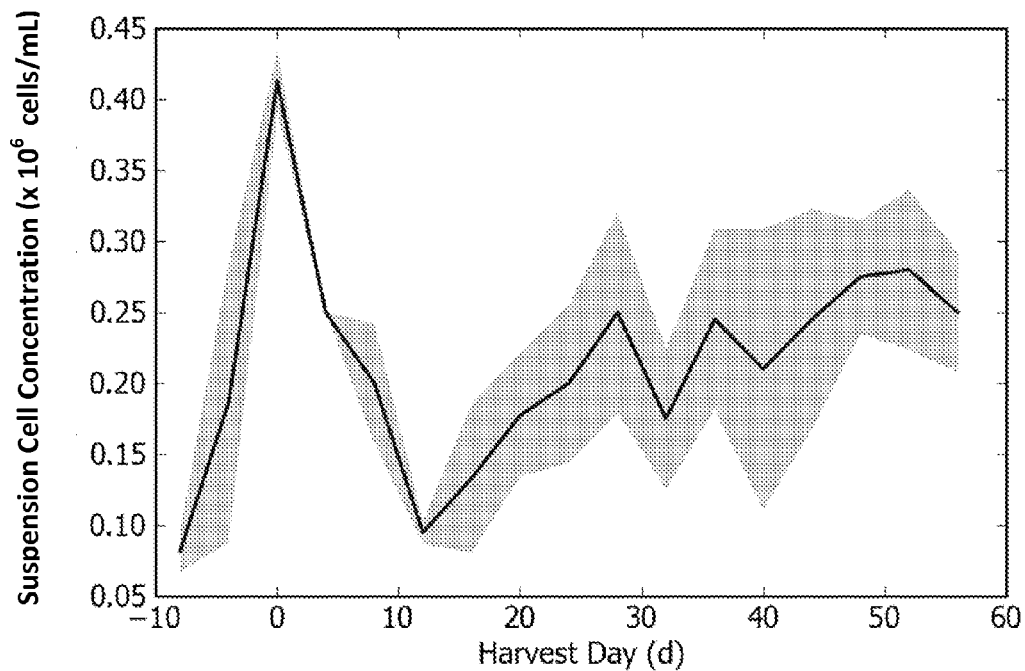
FIG. 4 is a graph showing the average concentration of suspended cells (the concentration of cells not adhering to the microcarriers in the liquid culture medium) over time in recombinant human alpha-galactosidase shake flask microcarrier batch re-feed cell culture process runs (n=5). The shaded area represents the standard deviation of the data.

Cell detachment was also monitored throughout the cell culture process runs by measuring the suspended cell concentration in the culture (FIG. 4). The suspended cell concentration in the culture peaked at the beginning of the harvest phase, most likely due to the effect of serum withdrawal on the cells. The suspended cell concentration remained low (between $0.1 \times 10^6$ to $0.3 \times 10^6$ cells/mL) throughout the cell culture process runs.

Culture Productivity

Figure 5:
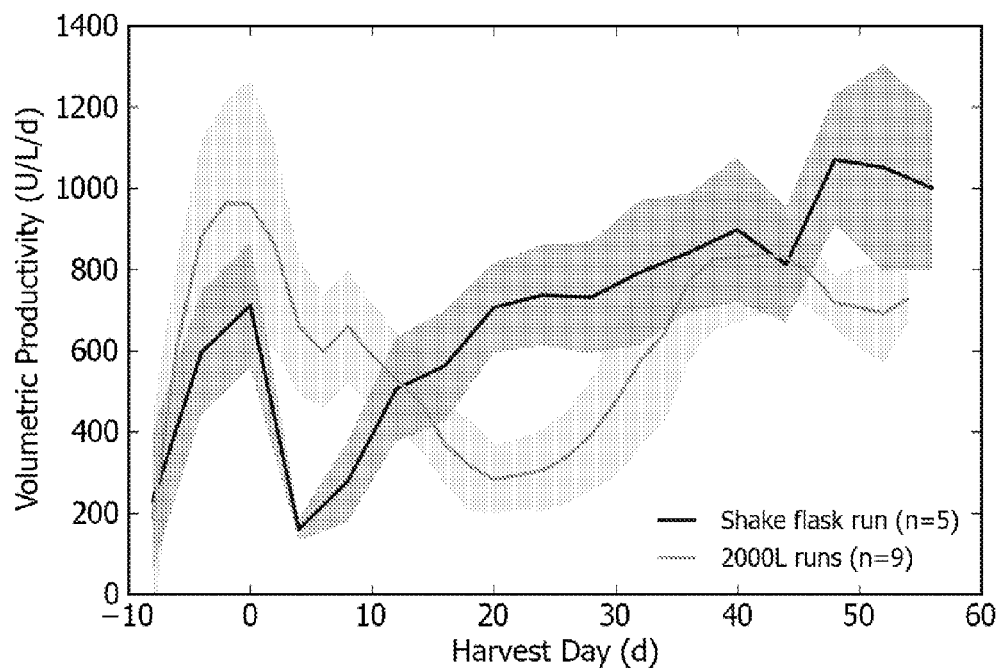
FIG. 5 is a graph of the average volumetric productivity over time in recombinant human alpha-galactosidase shake flask microcarrier batch re-feed cell culture process runs (n=5) and 2000-L bioreactor cell culture process runs (n=9). The shaded areas represent the standard deviation of the data.

Volumetric productivity (units/L/day) was monitored throughout the cell culture process runs to gain an understanding of the productivity performance of the shake flask microcarrier batch re-feed model. As shown in FIG. 5, culture productivity peaked at the late transition phase/early harvest phase. However, as the culture adapts to the lack of serum, a sharp decline in productivity is observed. The cell culture recovers from this trough period in early harvest phase, with the culture productivity improving throughout the harvest phase. About half-way into the harvest phase (around day 20 of the harvest phase), the cell culture productivity maintains a steady level (with volumetric productivity rate (VPR) above 600 units/L/day) until the end of run. It is noted that there was not a trough period in viable cell concentration (FIG. 2) that corresponds to the trough period observed for cell culture productivity.

Figure 6:
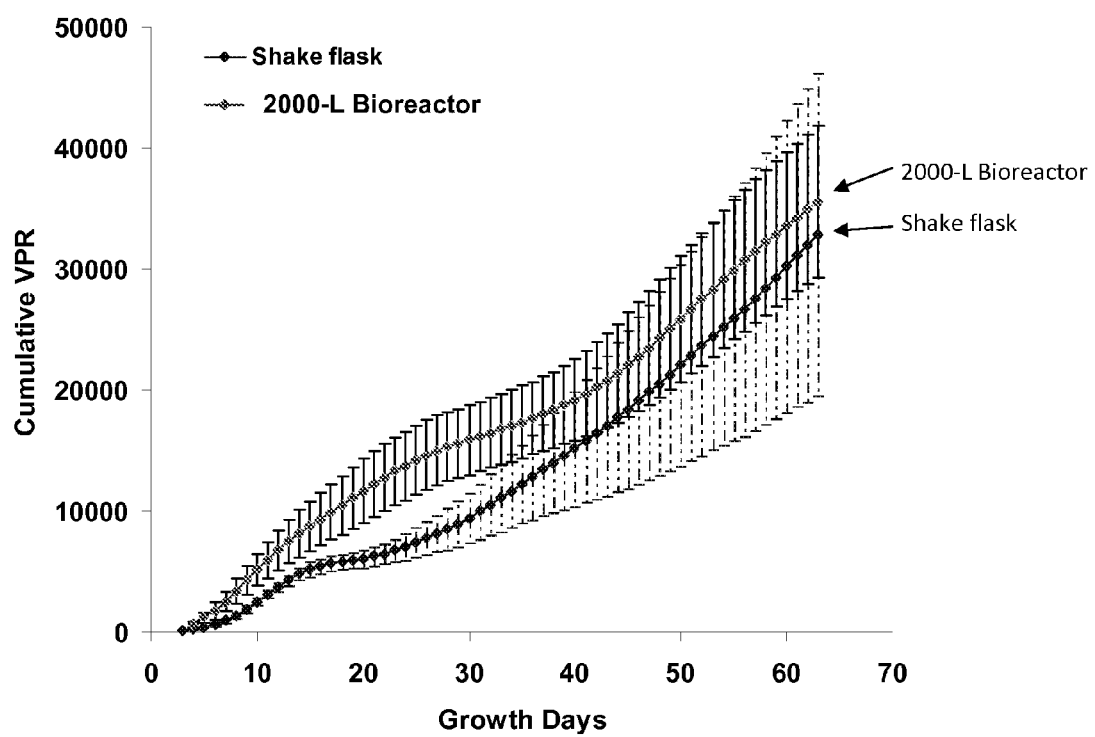
FIG. 6 is a graph of the cumulative volumetric productivity (units/L) over time in recombinant human alpha-galactosidase shake flask microcarrier batch-refeed cell culture process runs (n=3) and in recombinant human alpha-galactosidase 2000-L bioreactor culture process runs (n=3).

When comparing the productivity profile of this exemplary shake flask microcarrier batch re-feed process to the 2000-L process, two distinctive differences are observed. First, the productivity peak during the late transition phase/ early harvest phase is higher in the 2000-L process when compared to the exemplary shake flask microcarrier batch re-feed process. Second, the trough period for the 2000-L process is delayed to the mid-harvest phase rather than during the early harvest phase seen in the exemplary shake flask microcarrier batch re-feed process. The recovery in culture productivity following the trough is also slower in the 2000-L process than in the exemplary shake flask microcarrier batch re-feed process. These performance differences may be attributed to the difference in the medium exchange methods used in the two cell culture processes. Medium exchange in the 2000-L perfusion process is conducted in a continuous manner, where the cells are continuously exposed to conditioned/fresh medium. On the other hand, medium exchange in the exemplary shake flask microcarrier batch re-feed model described in this Example is conducted once a day, where 70% of the volume of the first liquid culture medium is removed and replaced with about the same volume of a second liquid culture medium in a bolus fashion. However, the cumulative volumetric productivity in the exemplary shake flask cell culture process run described in this Example and the 2000-L bioreactor cell culture process run show a similar trend (FIG. 6).

Culture Metabolism

Cellular metabolism was monitored during the cell culture process runs through glucose and lactate concentration measurements. The glucose consumption rate and lactate production rate were calculated from glucose and lactate analysis of the harvest phase samples. Lower lactate levels during the harvest phase indicates efficient glucose usage by the cultured cells. Overall, both glucose consumption and lactate production were consistent with the cell growth profile (FIG. 2). The most dynamic periods of the culture occurred at two different culture stages: i) where cell proliferation occurs with serum-containing medium, and ii) towards the end of the harvest phase, where a re-growth period occurs (noted by an increase in both viable cell density and metabolic activity). Glutamine and glutamate concentration profiles indicate a decline in glutamine consumption and glutamate production during the early harvest phase, which corresponds to the observed trough period.

Culture pH, $pCO_2$, and $pO_2$

Culture pH, $pCO_2$, and $pO_2$ profiles were monitored using the blood gas analyzer during sampling. Both the pH and $pO_2$ profiles were consistent with the viable cell concentration profile. The $pCO_2$ profile shows that $pCO_2$ levels were maintained between 30-35 mmHg, which correspond to the 5% $CO_2$ setting of the incubator.

Summary of Results

The exemplary recombinant alpha-galactosidase shake flask microcarrier batch re-feed cell culture process runs described in this Example achieve several beneficial results, e.g., the achievement of a transition cell density of $2.5 \times 10^6$ viable cells/mL to $3.0 \times 10^6$ viable cells/mL in only 7-9 days, the maintenance of a viable cell concentration of between $2.0 \times 10^6$ cells/mL to $6.0 \times 10^6$ cells/mL through the harvest phase, the achievement of a low suspended cell concentration ($<0.5 \times 10^6$ cells/mL) throughout the culture process (with the exception of a short period of elevated suspended cell concentration shortly after the serum is removed from the culture), and achievement of culture productivity peaks late in the transition phase. It is noted that while the culture productivity does undergo a short trough during early harvest phase, the recovery from this trough is prompt, with a volumetric productivity above 600 units/L/day throughout the harvest period.

The degree of variability of shake flask microcarrier cell culture process runs can be attributed to small differences in liquid culture medium/raw materials and experimental variability. However, the culture performance trends should be similar. This exemplary shake flask microcarrier batch re-feed process has been used for several other applications, such as satellite cultures in support of bioreactor runs (40-L and 2000-L cell culture process runs), trace metal and transition temperature studies on the production of recombinant human alpha-galactosidase, and cell culture process understanding and development.

As will be appreciated by one skilled in the field of biotechnology, the exemplary shake flask microcarrier batch re-feed process used for the production of recombinant alpha-galactosidase described in this Example can be extended to other applications, such as testing and designing improvements to a cell culture process, and monitoring or trouble-shooting a manufacturing process. The small scale shake flask microcarrier processes described herein will also allow for the minimization of resources and materials required for the larger bioreactor processes.

Example 2. Experiments to Determine the Effect of Microcarrier Concentration and Frequency of Agitation on Viable Cell Concentration in Shake Flasks A set of experiments were performed in order to test the effect of different microcarrier concentrations with different frequencies of agitation on mammalian cell culture growth performance in shake flasks.

Methods

The cells were cultured under the growth phase conditions described in Example 1, except that different concentrations of microcarriers and different frequencies of rotary agitation were used.

The culture used to inoculate the shake flasks containing the microcarriers was prepared by placing a thawed cell bank into two 250-mL size shake flasks with 50 mL growth medium. The resulting seed cultures were incubated in shake flasks at 37° C., 125 RPM, 6% $CO_2$, and 80% relative humidity until they were used to inoculate shake flasks containing the microcarriers. Following inoculation, the shake flasks containing microcarriers were cultured using the parameters set forth below. In all the experiments, 925 medium with 10% Dulbecco's bovine serum, pH 7.0, 0.1% Pluronic F-68 was used.

TABLE 2

Cell Culture Conditions

| Culture | A | B |
|---|---|---|
| Scale | 250 mL, smooth shake flask, 60 mL working volume | |
| Ucarrier type | CytoPore 2 | CytoPore 2 |
| [carrier], g/L | 1.0, 1.5, 2.0 | 1.0, 1.5, 2.0 |
| Seeding density | $0.25 \times 10^6$ viable cells/mL | |
| G-phase Medium | 925 medium with 10% serum | 925 medium with 10% serum |
| Temp (C.) | 37 C. | 37 C. |
| Agitation (RPM) | 125 or 85 | |
| % RH | 80% | |
| # Replicates | 2 | |

The microcarriers were prepared in phosphate buffered saline and autoclaved. The resulting sterilized microcarriers were then added into each shake flask under sterile conditions to reach a final concentration in each cell flask of 1 g/L, 1.5 g/L, or 2 g/L. The shake flask microcarrier cultures were then cultured for 6 days, and the viable cell density was determined over time.

Results

Figure 7:
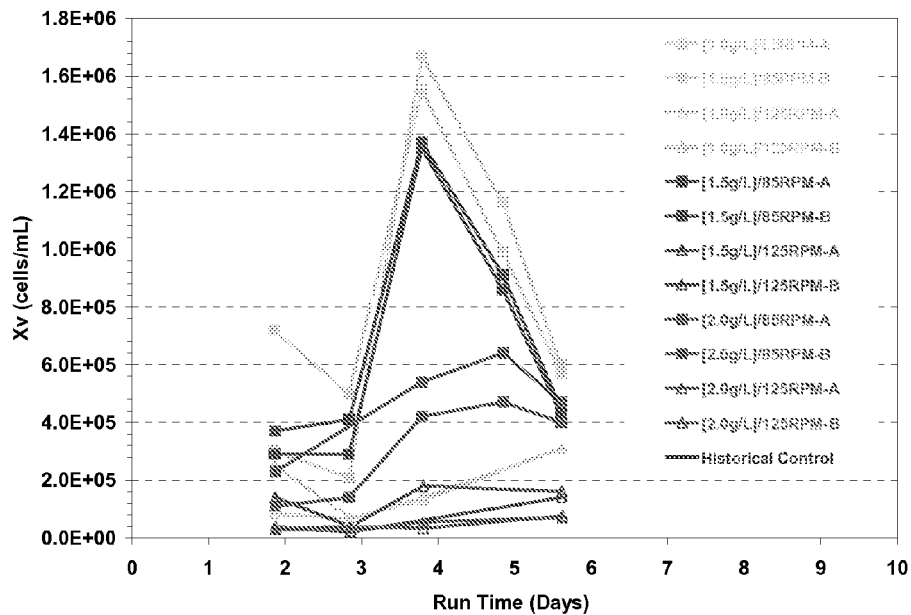
FIG. 7 is a graph of the viable cell concentration over time for shake flask microcarrier batch re-feed cell culture process runs containing different: types of liquid culture medium (liquid culture medium A or B), concentrations of microcarrier (a concentration of microcarriers of 1.0 g/L or 1.5 g/L), and/or different frequencies of rotation (85 RPM or 125 RPM).

The data in FIG. 7 show that mammalian cells can grow in shake flasks containing microcarriers when agitated at a frequency of 85 RPM or 125 RPM. The data also show that when a frequency of agitation of 85 or 125 RPM is used, shake flasks containing 1.0 g/L and 1.5 g/L microcarriers have a higher viable cell density.

Example 3. Shake Flask Culture as a Model of a 40-L Bioreactor Process

This study was designed to explore use of the shake flask culturing methods described herein for satellite culture of a 40-L recombinant human alpha-galactosidase bioreactor, and to compare the performance and production achieved in the satellite shake flask cultures to the performance and production achieved in a 40-L bioreactor culture.

Procedures

Scale-Down Model Description

The 40-L bioreactor used in these experiments is a stainless steel, stirred tank vessel developed to mimic a 2000-L manufacturing production bioreactor. This fully-automated vessel is steam-in-place sterilized, and has a control infrastructure and utility configuration similar to a 2000-L production bioreactor.

The 250-mL satellite shake flask culture utilizes a disposable gamma-sterilized Corning non-pyrogenic polycarbonate Erlenmeyer flask with a vented cap. The satellite shake flask culture is incubated in an Appropriate Technical Resources, Inc. (ATR) incubator with $CO_2$, humidity, and temperature controlled. The ATR incubator both controls and monitors the environmental conditions of the satellite shake flask cultures.

Methods

40-L Bioreactor Culture

The 40-L recombinant human alpha-galactosidase bioreactor cultures sampled for this study were inoculated with two working cell banks: 09TP040 and 09TP038. Recombinant cells that contain a nucleic acid encoding recombinant human alpha-galactosidase were initially grown in suspension culture until used to inoculate a 40-L bioreactor containing Cytopore II microcarriers at a final concentration of 1.5 g/L. The cells were cultured in a 10% serum-containing medium and stepped down to 6% serum-containing medium at the N−1 stage. The cells were cultured in 6% serum-containing medium until the completion of the growth phase in the 40-L bioreactors. Serum-containing growth medium was removed and replaced at a rate of 1.2 RV/day for 120 hrs at the completion of growth phase in order to transition the 40-L bioreactor cultures to serum-free production medium. The 40-L bioreactors were operated to model a 2000-L production bioreactor with controlled parameters (dissolved oxygen, pH, temperature, and $pCO_2$) maintained within manufacturing specifications/ranges and physical parameters (perfusion rate, agitation, sparger gas exit velocity, and cone flush rate) were scaled to match a 2000-L bioreactor with the exception of nitrogen sparge, overlay concentration, and surface area to volume.

Multiple experimental conditions were investigated in the 40-L bioreactors in the satellite shake flask culture studies. The 40-L bioreactor cultures sampled for the harvest phase satellite cultures used the cell line WCB 09TP040, and were operated with and without the addition of Trace A Elements (Invitrogen) to the serum-free production medium. The non-Trace A Elements 40-L bioreactor culture data was included in the comparisons with the satellite shake flask culture data due to its similar performance to both the Trace A Elements 40-L bioreactor culture data and the satellite shake flask culture data. The 40-L bioreactor cultures sampled for the growth phase satellite cultures used the cell line WCB 09TP038 and irradiated serum in the growth medium.

250 mL Shake Flask Satellite Cultures

Figure 8:
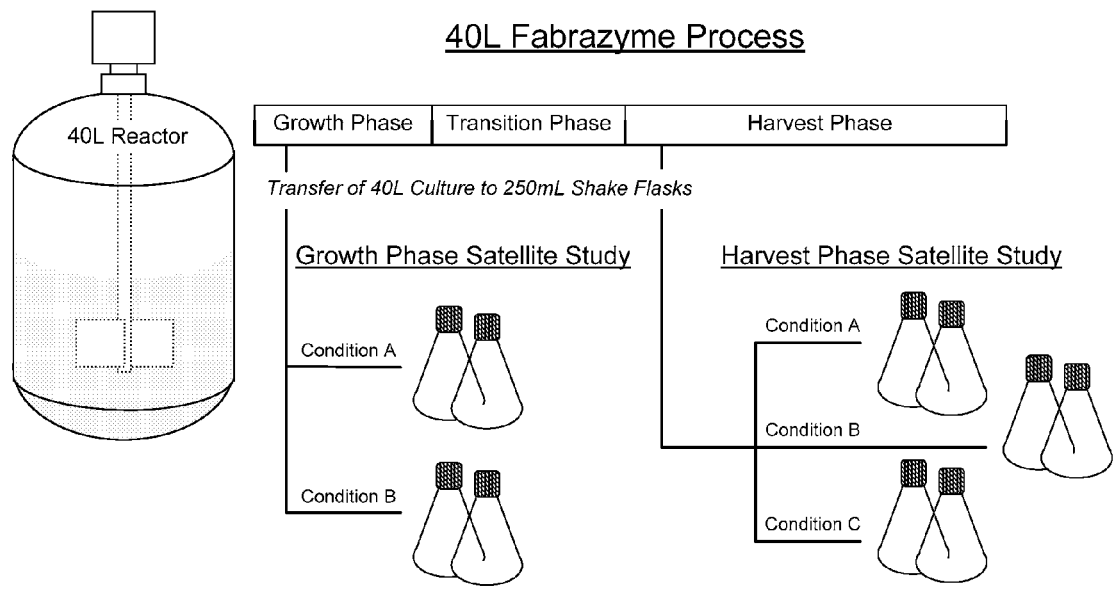
FIG. 8 is a schematic diagram of the growth phase and harvest phase satellite shake flask culture study.

The 250-mL satellite shake flask cultures were started at two time points during the recombinant human alpha-galactosidase 40-L bioreactor culture: growth phase and harvest phase (FIG. 8). A sterile 250-mL live cell culture microcarrier-containing sample was removed from the 40-L bioreactor cultures using a sample port. Well-mixed culture from this sample was then sterile transferred to either a 250-mL shake flask or a sterile flat-bottom container with a stir bar used to pool culture from multiple reactors. If the culture was pooled first, a well-mixed sample from this pool was then transferred to a 250-mL shake flask. Once the culture has been transferred to the 250-mL shake flask, a sample was taken for cell counts, metabolites, and titer. After sampling, if perfusion was ongoing in the 40-L bioreactor cultures, a re-feed was performed on the shake flasks and then they were transferred to an ATR shaker incubator.

Satellite shake flask culture working volume and incubator rotational RPM were varied. The working volume was reduced from an initial 68 mL to 60 mL, and then to 50 mL. The weight of the flask was checked on day 0 after the inoculation, and then checked daily to verify that flask volume remained constant after batch re-feed. The frequency of rotation was increased from 95 RPM to 110 RPM to determine if more efficient mixing would have a beneficial effect on culture performance. It was observed in previous experiments that at 95 RPM, microcarriers tended to concentrate to the center of the 250-mL shake flask, whereas at 110 RPM, there was a more even distribution of microcarriers throughout the shake flask. The harvest phase satellite shake flask cultures were agitated at a constant frequency throughout the experiment. The growth phase satellite shake flask cultures, independent of condition, were initially started at 85 RPM, and then ramped up to 95 RPM on growth day 3. This agitation strategy was chosen to minimize the shear stress on these cultures during the first few days of adaption to the shake flask growth conditions, and then increased to provide adequate mixing.

The ATR incubator was maintained at 5.0% $CO_2$, 37° C., and 80% relative humidity (RH) for all satellite shake flask cultures. The 5.0% $CO_2$ concentration was not comparable to the 40-L bioreactor culture $CO_2$ concentrations, but it was selected due to the lack of pH control and ease of operation. The temperature of the satellite shake flask cultures was left at a standard incubator temperature of 37° C. instead of matching the 40-L bioreactor culture temperature of 36° C. This was assumed to not have a large effect on satellite shake flask culture performance.

To reproduce the growth conditions of the 40-L perfusion bioreactor cultures in the satellite shake flask cultures, a 0.7× flask volume batch re-feed was performed daily to replace spent medium with fresh medium. Batch re-feeding was accomplished by tilting and holding the 250-mL shake flask at a 45° angle with a specialized rack. The cell-attached/containing microcarriers were allowed to settle for ~1 minute, and the spent media was removed and replaced with fresh medium. The fresh medium was stored at 4° C. before use and equilibrated to 5.0% $CO_2$ and 37° C. in a 250-mL shake flask in an ATR shaker incubator for ~1-3 hours before re-feed. All of the satellite shake flask cultures were sampled before the daily re-feed, every 2-3 days, for pH, $pO_2$, and $pCO_2$ (Bayer 248 Blood Gas Analyzer), viable cell density (Vicell XR), percentage of viable cells (viable cells/total cells; Vicell XR), metabolite concentration (glucose, lactate, glutamine, glutamate; YSI 2700), Apoptosis (Guava Nexin Assay), and titer of recombinant human alpha-galactosidase.

The harvest phase satellite shake flask cultures were sampled from two 40-L bioreactors: IDs P403-38 and P407-33. The 40-L bioreactor cultures were operated with Trace A Elements (Invitrogen) addition to the production media. Three harvest phase satellite cultures were started on harvest day 2 from culture removed from the P407-33 bioreactor culture, and directly transferred to three 250-mL shake flasks at a working volume of 68 mL. Two harvest phase satellite shake flask cultures were started on harvest day 4 from culture removed from the P403-38 bioreactor culture, and two satellite harvest phase shake flask cultures were started on harvest day 4 from culture removed from the P407-33 bioreactor culture. The samples removed from these 40-L bioreactor cultures were directly transferred to the four 250-mL harvest phase satellite shake flask cultures at a working volume of 60 mL without being pooled. All harvest phase satellite shake flask cultures were sampled post-transfer, and then a re-feed was performed at 0.7× shake flask volume before being placed into an ATR incubator. The medium used in the harvest phase satellite shake flask cultures was a different lot number than the medium used in the 40-L bioreactor cultures, but was the same composition and contained 1× Trace A Elements (Invitrogen). These harvest phase satellite shake flask cultures were maintained until the end-of-process (harvest day 53).

The culture for the growth phase satellite shake flask cultures was sampled from two 40-L bioreactor cultures: IDs P405-29 and P408-29 at post-inoculation by ~1 hour on G0 (day of inoculation). The two 40-L bioreactor culture samples were pooled, and then transferred to four 250-mL shake flasks at two working volumes (Table 3). Batch re-feed was started on G4, a day later than the start of the 40-L perfusion bioreactor culture (G3), due to a day of lag observed in satellite shake flask culture cell counts and metabolite consumption. These growth phase satellite shake flask cultures were maintained from G0-G8, but were terminated in early harvest phase due to a transition deviation resulting in a high transition cell density outside of the acceptable range and an extra day at 37° C. Only the growth data is used from this experiment.

TABLE 3

Conditions for 250-mL Shake Flask Satellite Study

| Phase | Duration | Experimental Conditions | Incubator Conditions |
|---|---|---|---|
| Growth Phase | G0-G8 | Condition 1:<br>60 mL w/v,<br>95 RPM<br>Condition 2:<br>50 mL w/v,<br>95 RPM | 5.0% $CO_2$, 37° C., and 80% RH |
| Harvest Phase | H2-H53 | Condition 1:<br>68 mL w/v,<br>95 RPM<br>Condition 2:<br>60 mL w/v,<br>95 RPM<br>Condition 3:<br>60 mL w/v,<br>110 RPM | 5.0% $CO_2$, 37° C., and 80% RH |

Results

Growth Phase Satellite Cultures

Figure 9:
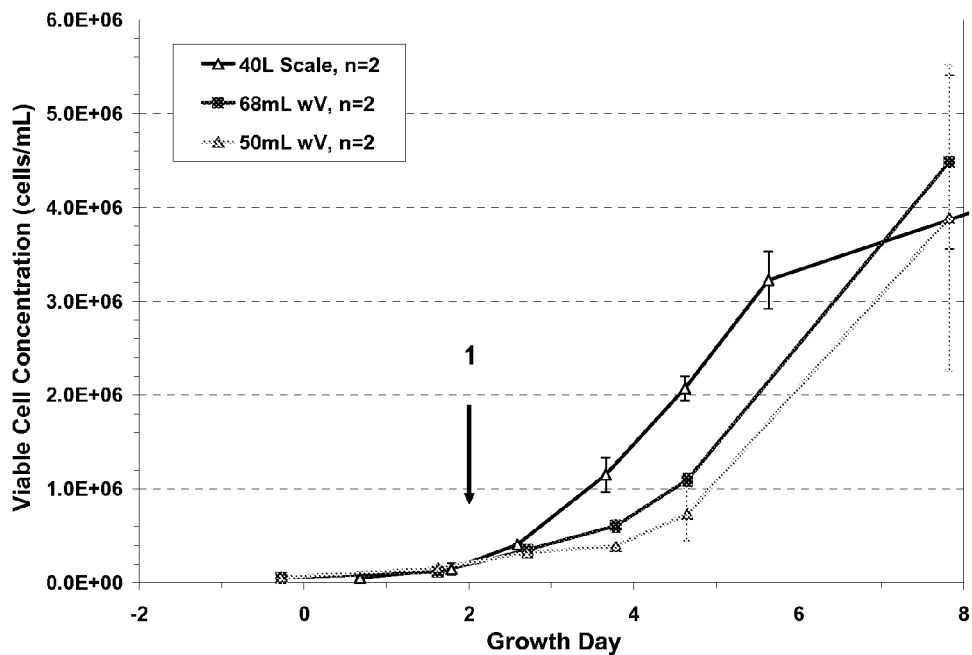
FIG. 9 is a graph of the viable cell concentration in the growth phase satellite shake flask cultures and the 40-L bioreactor cultures over time. The error bars represent +/−1 standard deviation of the data (n=2). "1" represents the time point when the frequency of agitation was increased from 85 RPM to 95 RPM. The growth phase satellite shake flask culture data was shifted by −1 day in order to more accurately compare the data to the 40-L bioreactor culture data.
Figure 10:
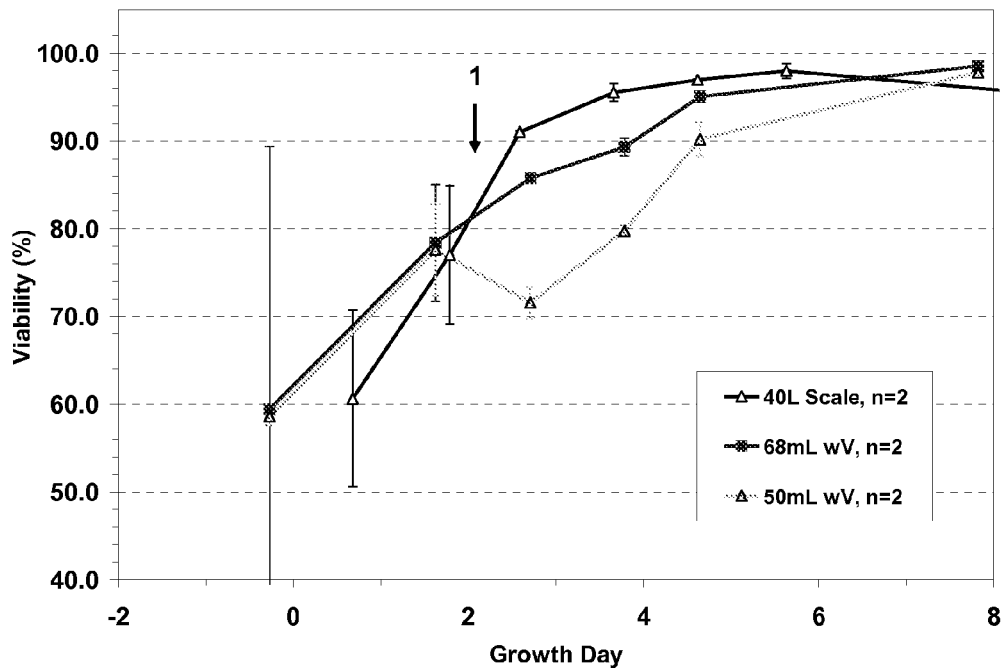
FIG. 10 is a graph of the percentage of viable cells in the growth phase satellite shake flask cultures and the 40-L bioreactor cultures over time. The error bars represent +/−1 standard deviation of the data (n=2). "1" represents the time point when the frequency of agitation was increased from 85 RPM to 95 RPM. The growth phase satellite shake flask culture data was shifted by −1 day in order to more accurately compare the data to the 40-L bioreactor culture data.
Figure 11:
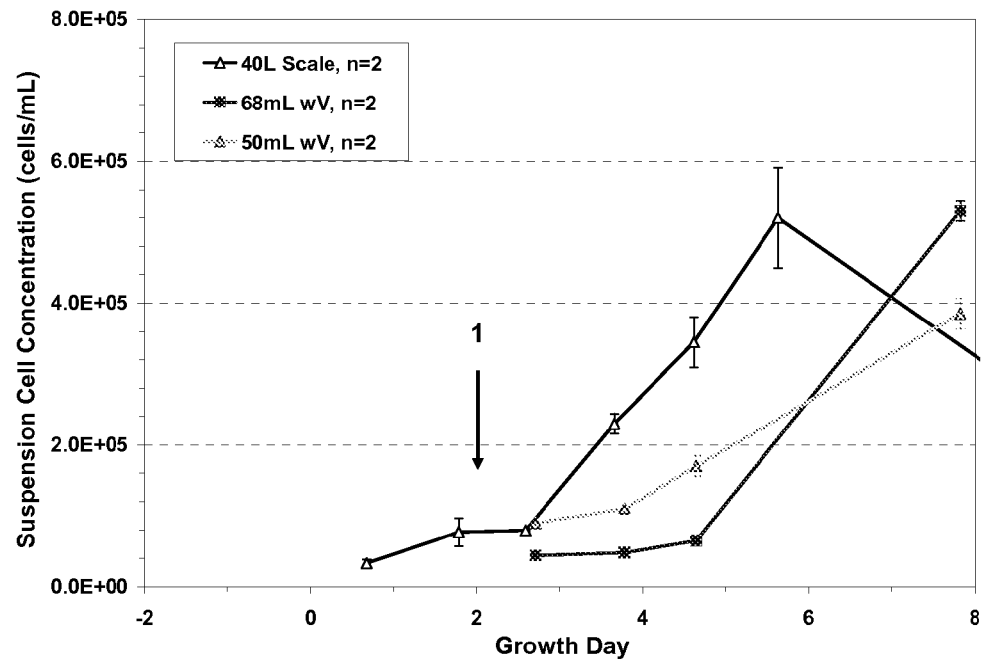
FIG. 11 is a graph of the suspended cell concentration in the growth phase satellite shake flask cultures and the 40-L bioreactor cultures over time. The error bars represent +/−1 standard deviation of the data (n=2). "1" represents the time point when the frequency of agitation was increased from 85 RPM to 95 RPM. The growth phase satellite shake flask culture data was shifted by −1 day in order to more accurately compare the data to the 40-L bioreactor culture data.

The viable cell growth for all conditions in the growth phase satellite shake flask cultures lagged due to transfer stress and agitation changes, but after recovery, viable cell growth was similar to the 40-L parent bioreactor cultures grown in parallel (FIG. 9). There was an initial day of cell growth lag in the growth phase satellite shake flask cultures. This growth lag is most likely caused by the stress on the culture during the transfer process from the 40-L bioreactor cultures. It has also been previously observed that the shake flask model requires additional days of growth to reach a transition density of $3.0 \times 10^6$ cells/mL. An additional day of lag was observed when the agitation was changed on growth day 2 from 85 RPM to 95 RPM. A larger effect was observed in the 50-mL growth phase satellite shake flask cultures. This lag was also observed in the culture viability data (FIG. 10), and is thought to be a result of additional shear stress due to the smaller working volume to flask volume ratio for the 50-mL growth phase satellite shake flask cultures. The increased shear stress most likely resulted in the increased suspension cell concentration in the 50-mL growth phase satellite shake flask cultures (FIG. 11).

Figure 12:
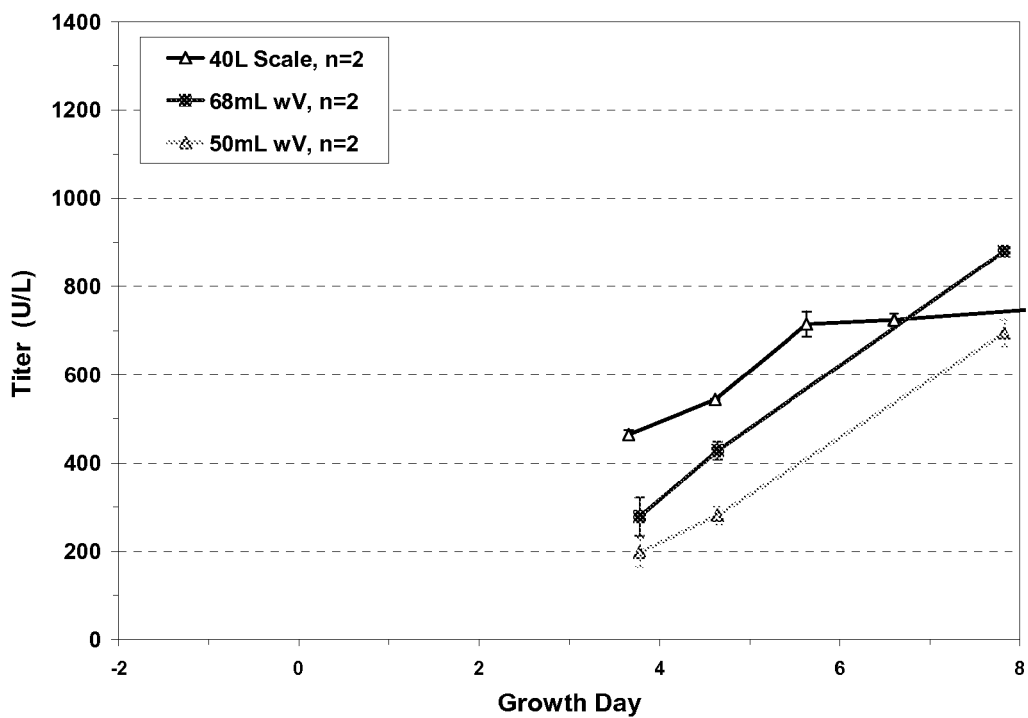
FIG. 12 is a graph of the titer (units/L) of recombinant human alpha-galactosidase in the growth phase satellite shake flask cultures and the 40-L bioreactor cultures over time. The error bars represent +/−1 standard deviation of the data (n=2). The growth phase satellite shake flask culture data was shifted by −1 day in order to more accurately compare the data to the 40-L bioreactor culture data.
Figure 13:
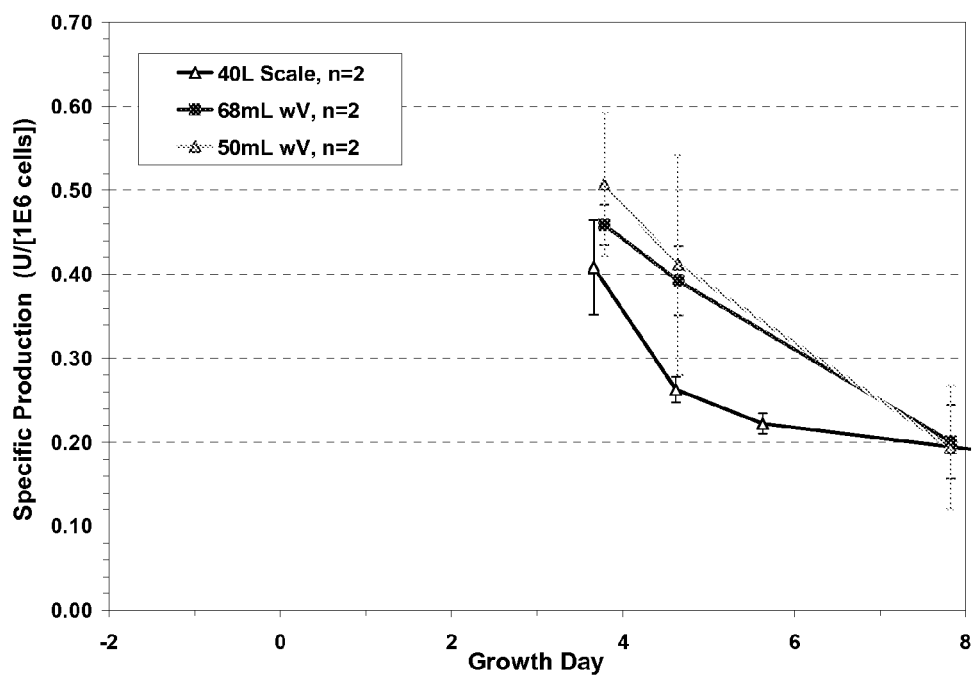
FIG. 13 is a graph of the specific productivity of recombinant human alpha-galactosidase (units per $1\times10^6$ cells) for the growth phase satellite shake flask cultures and the 40-L bioreactor cultures over time. The error bars represent +/−1 standard deviation of the data (n=2). The growth phase satellite shake flask culture data was shifted by −1 day in order to more accurately compare the data to the 40-L bioreactor culture data.

Production in all conditions in the growth phase satellite shake flask cultures trended similar to the 40-L parent bioreactor cultures grown in parallel (FIG. 12). The lower titer observed in the growth phase satellite shake flask cultures was due to lower cell concentration. Specific production was initially slightly higher in the growth phase satellite shake flask cultures, but converged with the 40-L bioreactor culture data as the growth phase satellite shake flask cultures recovered (FIG. 13). The 50-mL growth phase satellite shake flask cultures had a lower titer compared to the 68-mL growth phase satellite shake flask cultures due to lower cell concentration, which was supported by similar specific production of recombinant human alpha-galactosidase between the two types of growth phase satellite shake flask cultures (FIG. 13).

Figure 14:
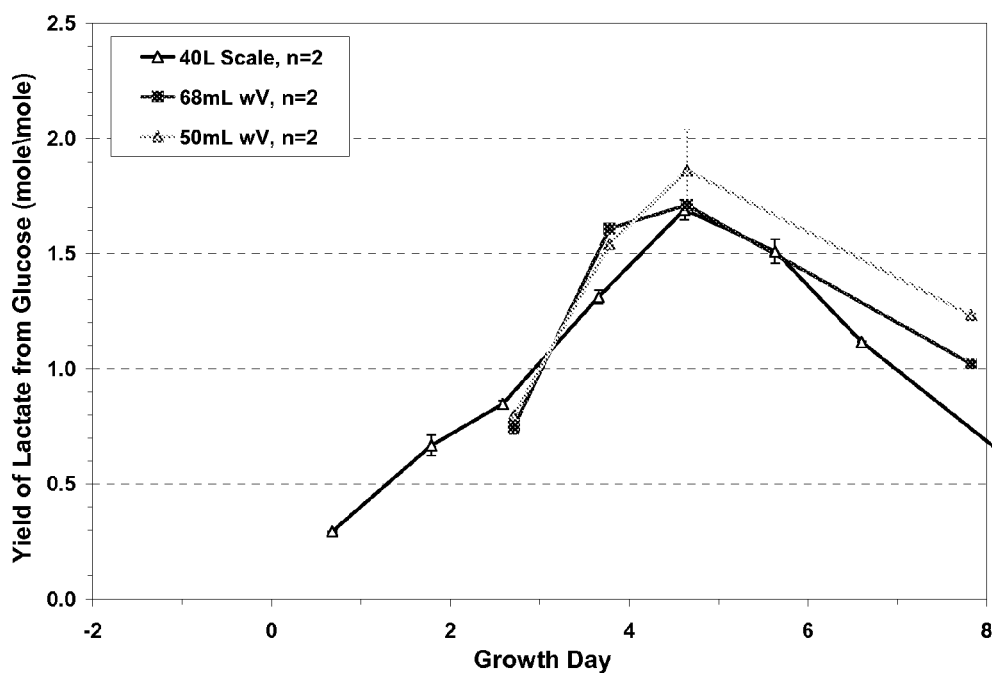
FIG. 14 is a graph of the yield of lactate from glucose (moles of lactate/moles of glucose) for the growth phase satellite shake flask cultures and the 40-L bioreactor cultures over time. The error bars represent +/−1 standard deviation of the data (n=2). The growth phase satellite shake flask culture data was shifted by −1 day in order to more accurately compare the data to the 40-L bioreactor culture data.

The glucose, lactate, glutamate, and glutamine metabolism of the growth phase satellite shake flask cultures initially trended similar to the data from the 40-L bioreactor cultures, but started to deviate on day 5. The glucose and glutamine concentration in the growth phase satellite shake flask cultures increased with the first batch re-feed on day 3, and then declined as cell growth continued, and lactate production increased outside of the 40-L bioreactor culture range. Lactate production was higher in the growth phase satellite shake flask cultures on day 5, and then remained higher than the 40-L bioreactor cultures. The yield of lactate to glucose for the growth phase satellite shake flask cultures remained similar to the 40-L bioreactor cultures, which suggested that glucose/lactate metabolism was similar in the growth phase satellite shake flask cultures and the 40-L bioreactor cultures (FIG. 14). Glutamate concentration deviated from the 40-L bioreactor cultures in the growth phase satellite shake flask cultures, and then appeared to converge on day 8. The 40-L bioreactor cultures had a temperature reduction on growth day 5, which suppressed cell metabolism and growth. There was not a similar temperature shift in the growth phase satellite shake flask cultures, which caused the deviation in metabolism on growth day 8. Higher lactate production in the growth phase satellite shake flask cultures resulted in the deviation of glucose and glutamine on day 5. Lactate production was suppressed in the 50-mL growth phase satellite shake flask cultures compared to the 60-mL growth phase satellite shake flask cultures, but this was most likely a result of the lower cell density in this culture.

The pH in the growth phase satellite shake flask cultures was initially similar to the 40-L bioreactor cultures, but deviated on day 3 due to lack of active pH control and remained lower than the 40-L bioreactor cultures due to higher lactate production. The 40-L bioreactor cultures used NaOH addition to maintain the pH above 6.80. The growth phase satellite shake flask culture pH increased back into range of the 40-L bioreactor cultures on day 4 due to a re-feed on day 3 which suppressed/diluted lactate. The $pO_2$ and $pCO_2$ in the growth phase satellite shake flask cultures were very different from the 40-L bioreactor cultures due to the lack of active control for these parameters. The $pCO_2$ was lower in the growth phase satellite shake flask cultures due to more efficient sweep and a 5.0% $CO_2$ incubator set point. The $pO_2$ is higher in the growth phase satellite shake flask cultures than the 40-L bioreactor cultures, but decreases as cell growth increases in the growth phase satellite shake flask cultures. The higher cell mass in the 60-mL growth phase satellite shake flask cultures was represented by a lower $pO_2$.

Harvest Phase Satellite Shake Flask Cultures

Figure 15:
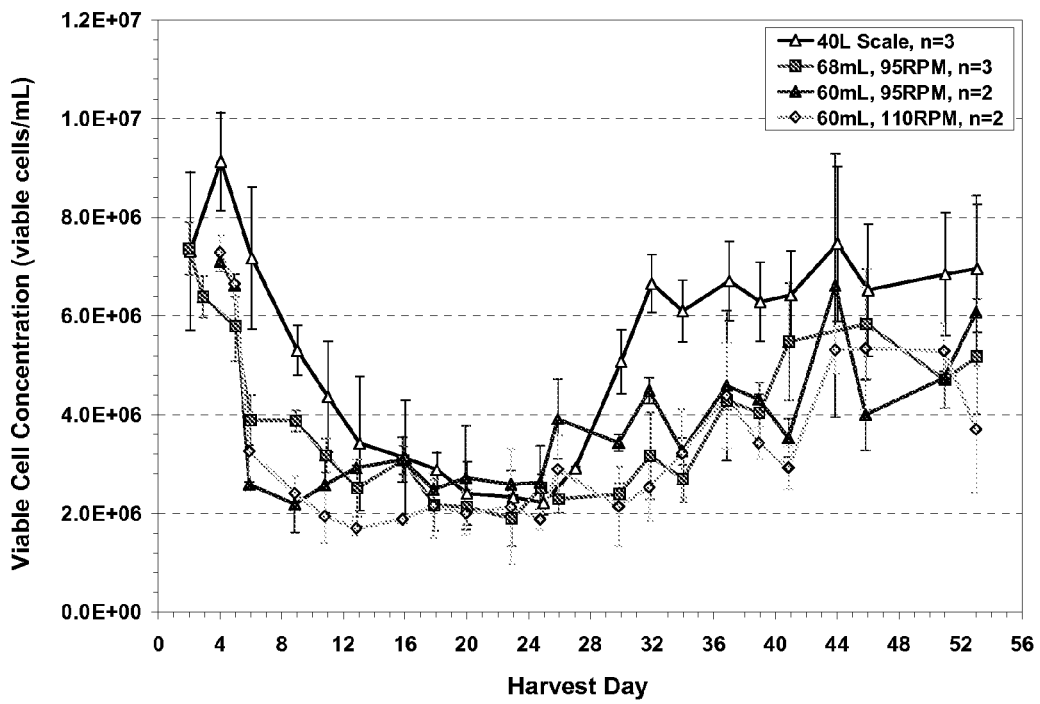
FIG. 15 is a graph of the viable cell concentration of the harvest phase satellite shake flask cultures and the 40-L bioreactor cultures over time. The average data are shown (40-L, n=3; 68 mL at 95 RPM, n=3; 60 mL at 95 RPM, n=2; and 60 mL at 110 RPM, n=2), with the error bars representing +/−1 standard deviation of the data.
Figure 16:
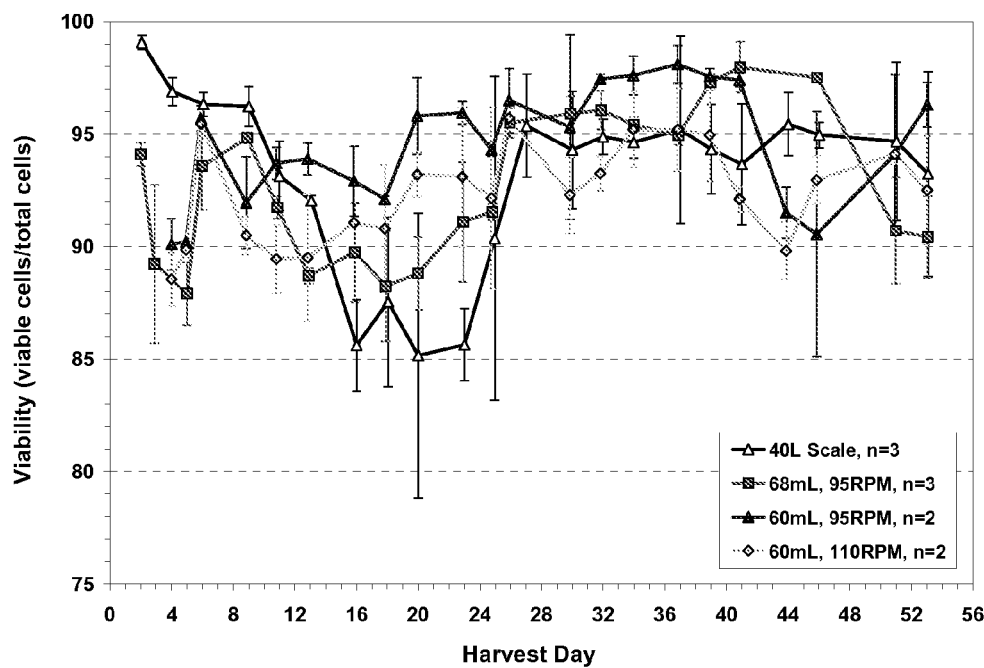
FIG. 16 is a graph of the percentage of viable cells in the harvest phase satellite shake flask cultures and the 40-L bioreactor cultures over time. The average data are shown (40-L, n=3; 68 mL at 95 RPM, n=3; 60 mL at 95 RPM, n=2; and 60 mL at 110 RPM, n=2), with the error bars representing +/−1 standard deviation of the data.
Figure 17:
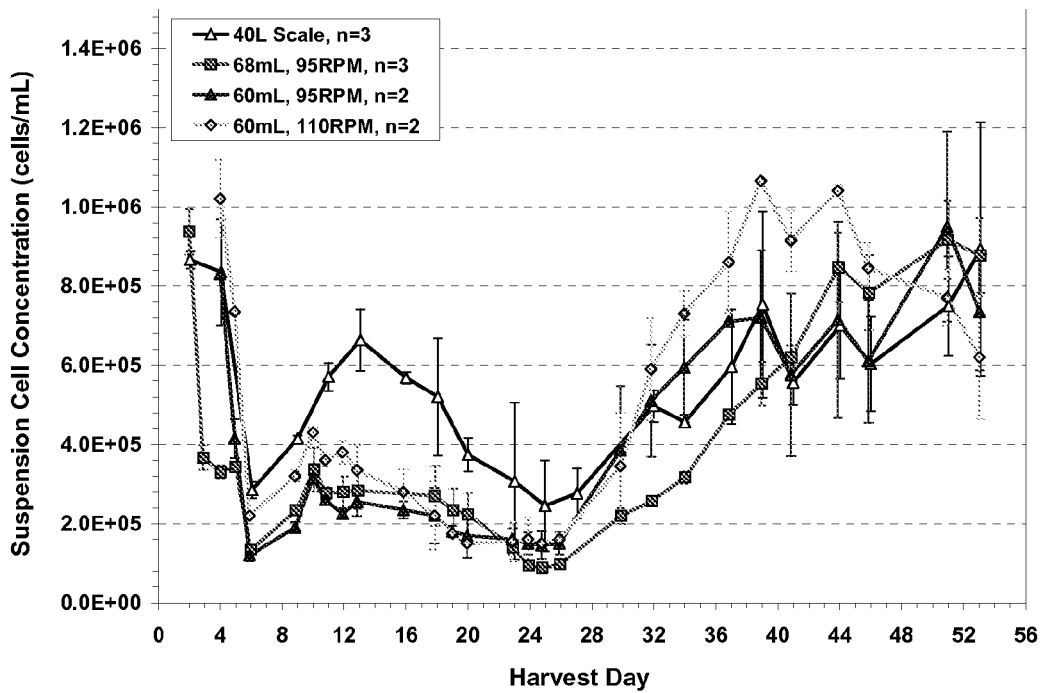
FIG. 17 is a graph of the suspended cell concentration in the harvest phase satellite shake flask cultures and the 40-L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.

Viable cell growth for all conditions in the harvest phase satellite shake flask cultures was similar to the 40-L parent bioreactor cultures grown in parallel (FIG. 15). There was an initial drop in viable cell concentration in 2-3 days after being transferred to the 250-mL harvest phase satellite shake flask culture. This drop was more pronounced in the 60-mL harvest phase satellite shake flask cultures. This drop was 6-8 days earlier than the corresponding viable cell concentration trough in the recombinant human alpha-galactosidase 40-L bioreactor cultures (FIG. 15). Viability in the harvest phase satellite shake flask cultures followed the same trend as the 40-L bioreactor cultures, and decreased in the harvest phase satellite shake flask cultures during the trough period (FIG. 16). This viable cell concentration trough is thought to result from the adaption to serum-free medium and the batch re-feed process may possibly enhance this detrimental effect. Suspension cell concentration in the harvest phase satellite shake flask cultures was also lower compared to the 40-L bioreactor cultures during the trough period (FIG. 17). This was an indication of the lower total cell concentration, but may also suggest that the batch re-feed process washed cells and smaller aggregates more efficiently from the harvest phase satellite shake flask cultures. More efficient cell removal may also contribute to a faster drop in viable cell concentration as the harvest phase satellite shake flask cultures entered the trough period.

The harvest phase satellite shake flask cultures, independent of the condition, begin to recover from the trough period at the same time as the 40-L bioreactor cultures at H27-28 (FIG. 15). The 40-L bioreactor cultures showed a stronger increase in viable cell concentration, but there may have been problems with the instrument used to count cells during this period, and therefore the differences between the harvest phase satellite shake flask culture data and the 40-L bioreactor culture data may be exaggerated. It was also more difficult to pull a representative well-mixed sample from the harvest phase satellite shake flask cultures with microcarriers, and this may also have led to a difference in the measured cell concentrations. This type of error would have been enhanced at higher cell densities, as the microcarriers became heavier.

Suspension cell counts also begin to increase during this time frame in the harvest phase satellite shake flask cultures, and these data are in line with the suspension cell counts observed in the 40-L bioreactor cultures (FIG. 17). The harvest phase satellite shake flask cultures containing 60 mL medium and agitated at 110 RPM had a higher suspension cell concentration compared to the other harvest phase satellite shake flask cultures. This indicates that there may have been more shear stress with this agitation, which resulted in an increased level of detached cells. The harvest phase satellite shake flask cultures containing 60 mL of medium and agitated at 95 RPM also had a slightly higher suspension cell concentration exiting the trough, which suggested that the increase in shear stress at the lower working volume may have detached more cells than a harvest phase satellite shake flask culture utilizing a larger working volume of medium. However, titer production (FIG. 18) indicated that there may have been more cell mass in the 60-mL harvest phase satellite shake flask cultures than what was represented by Vicell viable cell counts. This higher cell mass and growth may have also added to the higher suspension cell counts. Viability in mid-late harvest was variable in all harvest phase satellite shake flask cultures, but remained high and was comparable to the data from the 40-L bioreactor cultures (FIG. 16).

Figure 18:
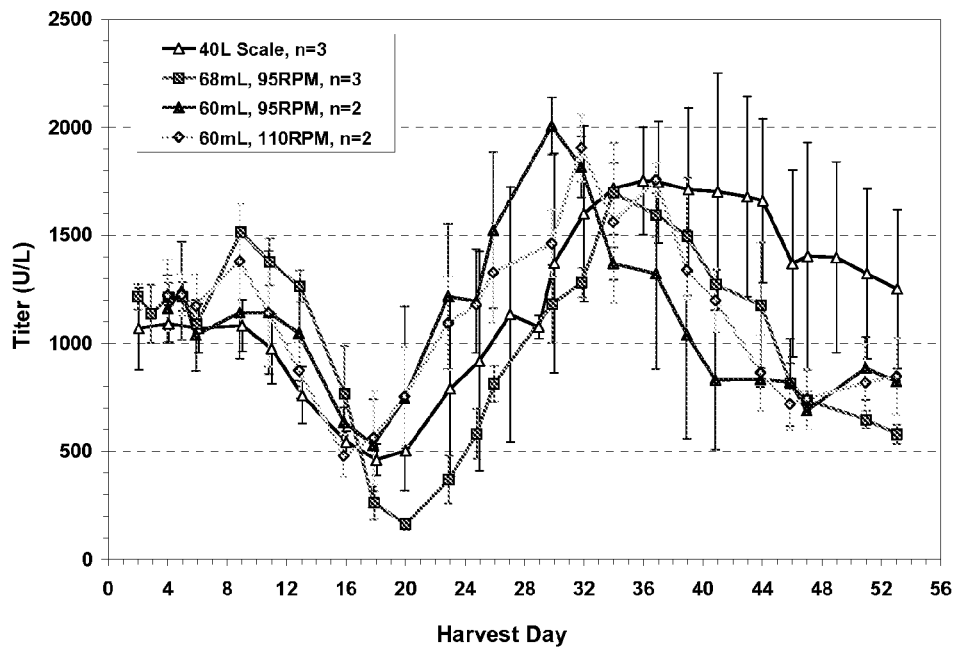
FIG. 18 is a graph of the titer of recombinant human alpha-galactosidase (units/L) in the harvest phase satellite shake flask cultures and the 40-L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.
Figure 19:
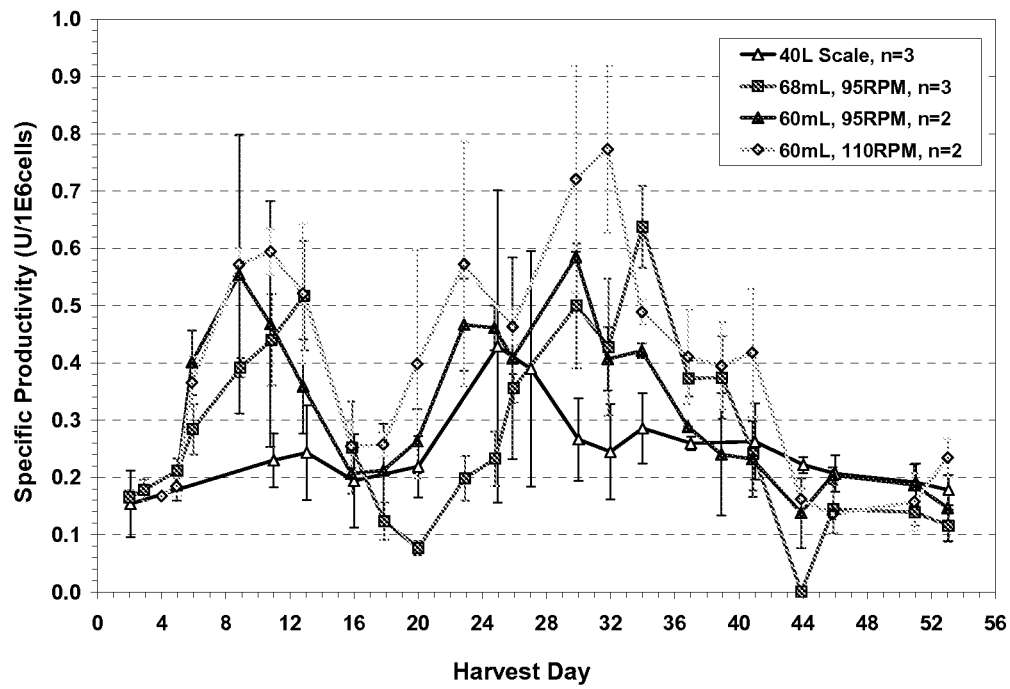
FIG. 19 is a graph of the specific productivity of recombinant human alpha-galactosidase (units per $1\times10^6$ cells) for the harvest phase satellite shake flask cultures and the 40-L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.
Figure 20:
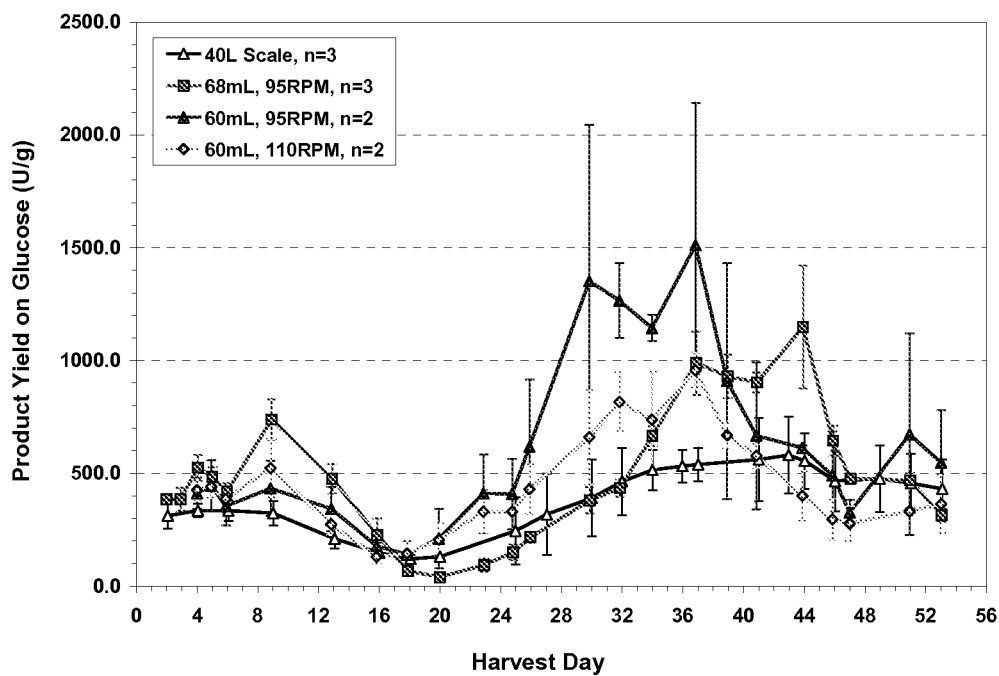
FIG. 20 is a graph of the yield of recombinant human alpha-galactosidase per gram of glucose (units/g) for the harvest phase satellite shake flask cultures and the 40-L bioreactor cultures over time. The average data are shown (40 L, n=3; 68 mL at 95 RPM, n=3; 60 ml, at 95 RPM, n=2; and 60 mL at 110 RPM, n=2), with the error bars representing +/−1 standard deviation of the data.

Titer production in the harvest phase satellite shake flask cultures was similar to the 40-L bioreactor cultures (FIG. 18). After the first 3-5 days in the harvest phase satellite shake flask culture, the productivity increased to a level that was higher than that observed in the 40-L bioreactor cultures. Specific productivity in the harvest phase satellite shake flask cultures was also increased outside of the range seen in the 40-L bioreactor cultures (FIG. 19) due to a growth response to the higher temperature, or a response to the higher percent oxygen in the harvest phase satellite shake flask cultures compared to the 40-L bioreactor cultures (FIG. 16). The product yield per gram of glucose in the harvest phase satellite shake flask cultures was initially similar to the 40-L bioreactor cultures, but diverged as lactate production increased in the harvest phase satellite shake flask cultures (FIG. 20). The product yield from aerobic glucose was lower in late harvest in the harvest phase satellite shake flask cultures, which indicated that glucose is not efficiency used in the harvest phase satellite shake flask cultures. The higher RPM harvest phase satellite shake flask cultures produced less lactate and had a more comparable product yield per gram of glucose compared to the 40-L bioreactor cultures, and a higher product yield on aerobic glucose consumption. This indicates that the higher rate of agitation (RPM) used in these harvest phase satellite shake flask cultures improved the utilization of glucose.

All harvest phase satellite shake flask cultures, independent of condition, entered the production trough at the same time period as the 40-L bioreactor cultures at H9-10. The harvest phase satellite shake flask cultures containing 68 mL of medium and agitated at 95 RPM troughed deeper after a higher, pre-trough increase in production compared to the other harvest phase satellite shake flask cultures (FIG. 18). This may have been a result of increased growth (previously seen to negatively affect trough depth in the 40-L bioreactor cultures from either lower shear stress), longer exposure to higher $O_2$ before trough period, or because they were sampled during an active growth phase in the 40 L bioreactor cultures.

The 60-mL harvest phase satellite shake flask cultures had a trough depth similar to the 40-L bioreactor cultures, and entered trough recovery earlier than the 68-mL harvest phase satellite shake flask cultures (FIG. 18). These cultures were sampled from the 40-L bioreactor cultures during a stationary/declining growth phase. This may have prevented extended cell growth in the harvest phase satellite shake flask cultures before the trough. A higher shear stress due to lower working volume may have also suppressed cell growth before the trough.

Figure 21:
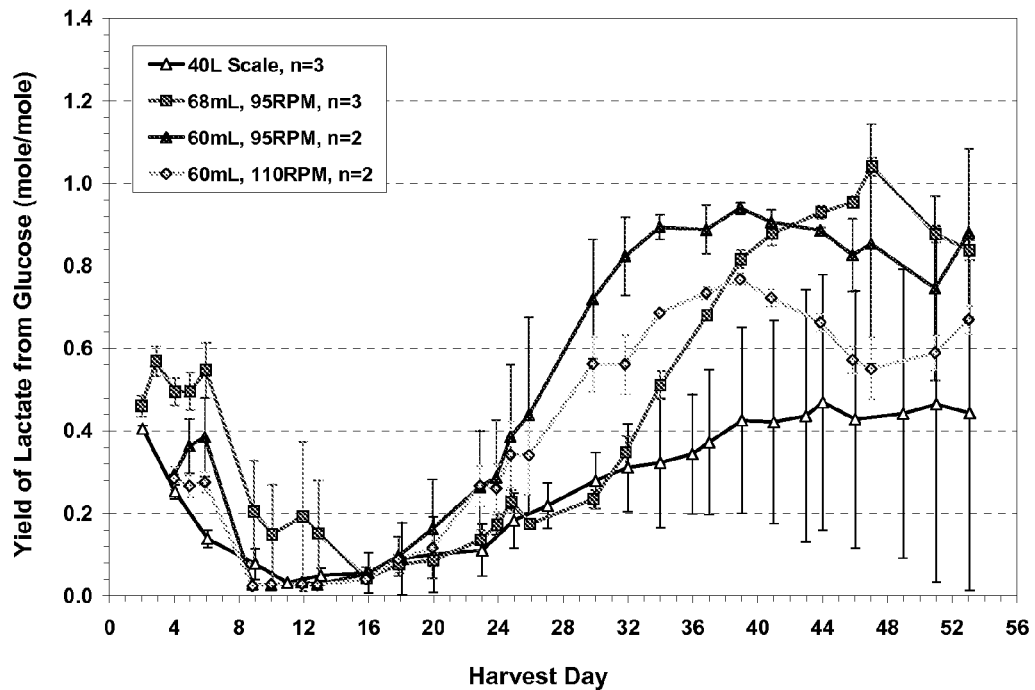
FIG. 21 is a graph of the yield of lactate from glucose (moles of lactate/moles of glucose) for the harvest phase satellite shake flask cultures and the 40-L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.

All harvest phase satellite shake flask cultures entered trough recovery similar to the 40-L bioreactor cultures (FIG. 18). An increase in specific productivity was also observed with a larger magnitude in the harvest phase satellite shake flask cultures, but trended similar to the 40-L bioreactor cultures (FIG. 19). All harvest phase satellite shake flask cultures, independent of conditions, had a similar trough to peak production recovery magnitude and length of recovery before a late harvest decline. The late harvest decline in the harvest phase satellite shake flask cultures trended similar to the 40-L bioreactor cultures, but was steeper. This is likely due to either the accumulation or depletion of a nutrient as harvest phase satellite shake flask culture metabolism started to greatly deviate from the 40-L bioreactor cultures around this same time frame (FIG. 21).

The glucose, lactate, glutamate, and glutamine metabolism of the harvest phase satellite shake flask cultures trended similar to the 40-L bioreactor cultures, but with different scale variations. The glucose consumption in the harvest phase satellite shake flask cultures was reduced as the cultures entered the trough period, and then increased as the cultures recovered, similar to the 40-L bioreactor cultures. However, lactate production was much higher in the harvest phase satellite shake flask cultures before and after the trough period. The increase in the lactate production resulted in an increase in the consumption of glucose and glutamate in the harvest phase satellite shake flask cultures well outside of the ranges seen in the 40-L bioreactor cultures. Glutamate became limited in late harvest for the harvest phase satellite shake flask cultures agitated at 95 RPM due to the high lactate production. Glutamine consumption in the harvest phase satellite shake flask cultures remained higher than the 40-L bioreactor cultures, but had a similar trend. The yield of lactate from glucose in the harvest phase satellite shake flask cultures was also higher than the range in the 40-L bioreactor cultures suggesting that there was a shift in metabolism in the harvest phase satellite shake flask cultures.

The 68-mL harvest phase satellite shake flask cultures had a delayed increase in lactate production that corresponded with the delayed increase in titer production (FIG. 18). The 60-mL harvest phase satellite shake flask cultures, independent of the frequency of agitation, peaked earlier in lactate production corresponding to the titer production peak in these cultures. This indicated that the lactate production is a result of the harvest phase satellite shake flask culture's energized metabolism post-trough during the culture recovery. However, agitation of the harvest phase satellite shake flask culture at 110 RPM was observed to suppress lactate production, glucose consumption, and glutamate consumption without having a suppressive effect on titer production. This may be the result of improved cell-to-cell interaction kinetics, aggregation, and/or improved oxygen availability due to better mixing. The higher lactate production in the harvest phase satellite shake flask cultures was observed when cell mass was increasing, suggesting that there may have been localized hypoxic events in the harvest phase satellite shake flask cultures that push the cultures toward anaerobic metabolism, or lower rotational speed promoted abnormal aggregate formation and microcarrier attachment during cell growth.

Lower $pO_2$ measurements in the harvest phase satellite shake flask cultures agitated at a frequency of 95 RPM as compared to the harvest phase satellite shake flask cultures agitated at a frequency of 110 RPM supported the role of oxygen in lactate suppression. The level of $pO_2$ in the harvest phase satellite shake flask cultures never dropped below the 40-L bioreactor culture level, but poor mixing that concentrates the cell mass at the bottom center of the shake flask may have produced an unmeasured lower $pO_2$ concentration in localized spots. The method of sampling for the Blood Gas Analyzer (BGA) measurement involved allowing the culture to settle, and then testing the top layer of supernatant. This technique may have provided a higher $pO_2$ value compared to localized spots of high cell concentration present in the culture.

Figure 22:
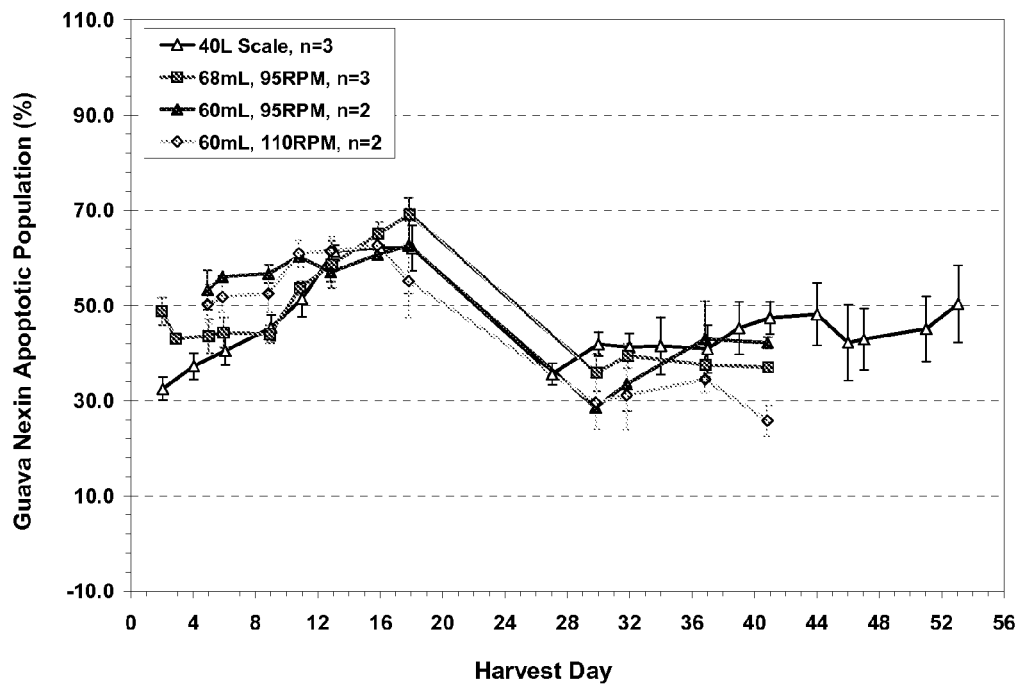
FIG. 22 is a graph of the percentage of the apoptotic cells present in the harvest phase satellite shake flask cultures and the 40-L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.
Figure 23:
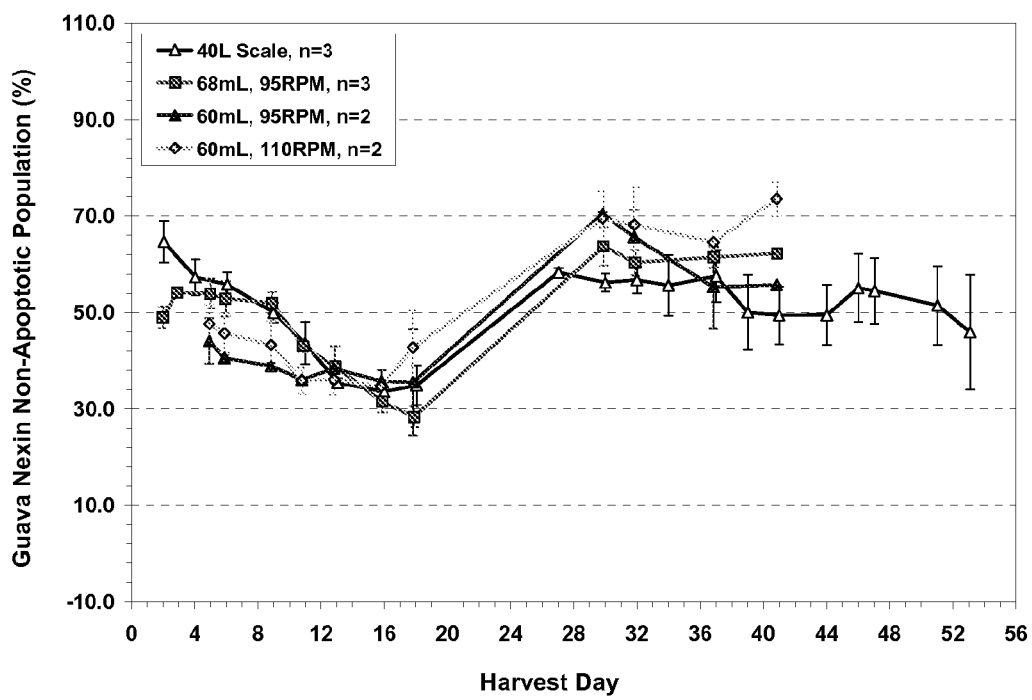
FIG. 23 is a graph of the percentage of non-apoptotic cells present in the harvest phase satellite shake flask cultures and the 40 L bioreactor cultures over time. The average data are shown (40 L, n=3; 68 mL at 95 RPM, n=3; 60 mL at 95 RPM, n=2; and 60 mL at 110 RPM, n=2), with the error bars representing +/−1 standard deviation of the data.

The apoptotic cell population in the harvest phase satellite shake flask cultures trended similar to the 40-L bioreactor cultures. There was an initial rise in cellular apoptosis in the harvest phase satellite shake flask cultures and 40-L bioreactor cultures as the cultures entered the trough period. This was then followed by a decrease and stabilization of cellular apoptosis as the culture recovered (FIGS. 22 and 23). The 60-mL harvest phase satellite shake flask cultures had an initial higher percentage of apoptotic cells, and then converged with the harvest phase satellite shake flask culture and the 40-L bioreactor cultures during the trough period. The 60-mL harvest phase satellite shake flask cultures were sampled from the 40-L bioreactor culture closer to the trough period than the 68-mL harvest phase satellite shake flask cultures, and this may have resulted in the higher apoptotic population. The harvest phase satellite shake flask cultures agitated at a frequency of 110 RPM appeared to have a lower apoptotic population in late harvest phase, but data was not generated past H41, and this may have been within the noise of the assay.

The pH, $pO_2$, and $pCO_2$ in the harvest phase satellite shake flask cultures were very different from the 40-L bioreactor cultures due to the lack of active control for these parameters. The harvest phase satellite shake flask culture pH started initially much higher than the 40-L bioreactor cultures due to a much lower $pCO_2$ profile, and then was driven primarily by the production of lactate. The $pO_2$ was higher in the harvest phase satellite shake flask culture than the 40-L bioreactor cultures, but trended with the cell concentration, increasing when the cultures entered the trough and decreasing towards 40-L bioreactor culture levels in late harvest as the harvest phase satellite shake flask cultures recovered. The $pCO_2$ concentration in the harvest phase satellite shake flask cultures was much lower than in the 40-L bioreactor cultures due to the very high sweep efficiency of the harvest phase satellite shake flask cultures and the low 5.0% $CO_2$ set point of the incubator. The differences in $pCO_2$ profiles between the harvest phase satellite shake flask cultures were due to incubator differences.

Summary

These data demonstrate the successful use of a 250-mL shake flask model for satellite culture of a recombinant human alpha-galactosidase 40-L bioreactor process. The transfer of live recombinant human alpha-galactosidase microcarrier cell culture from a 40-L bioreactor to a 250-mL satellite shake flask culture was successfully accomplished during the growth and harvest phase.

The harvest phase 250-mL satellite shake flask cultures were run in parallel to parent 40-L bioreactor cultures, and produced comparable cell growth and titer production. Cell concentration was lower in the harvest phase satellite shake flask cultures, suggesting that specific production of recombinant human alpha-galactosideash was higher than in the 40-L bioreactor cultures, but this may have also been due to difficulty attaining a representative sample of microcarriers from the harvest phase satellite shake flask cultures. The growth phase satellite shake flask cultures showed an initial day of lag in both cell growth and production compared to 40-L bioreactor cultures, and then a day of lag after an agitation change. The slower growth of the satellite shake flask cultures can be attributed to stress during transfer from the 40-L bioreactor cultures, and an increase in shear stress due to the agitation change. Specific productivity was higher in the 250-mL satellite shake flask cultures compared to the 40-L bioreactor cultures, but this may have been misrepresented by inaccuracies in the cell counting. On the other hand, the product yield on aerobic glucose in the satellite shake flask cultures was lower than that observed in the 40-L bioreactor cultures, when lactate production in the satellite shake flask cultures increased higher than the levels in the 40-L bioreactor cultures.

Clear differences were observed in culture pH, $pCO_2$, and $pO_2$ between the satellite shake flask cultures and the 40-L bioreactor cultures due to the lack of active control of these parameters in the satellite shake flask cultures. The $pCO_2$ concentration was much lower, $pO_2$ was higher, and the pH fluctuated outside the normal operation range compared to the 40-L bioreactor cultures. A higher temperature set point was also used in the 250-mL satellite shake flask cultures. These differences interestingly had little observable effect on culture growth, productivity, and apoptosis, suggesting that such parameters may also be more flexible in 40-L bioreactor cultures. However, these parameter differences may have been responsible for the difference in the satellite shake flask culture glucose, lactate, glutamate, and glutamine metabolism.

Two other parameters, mixing/agitation and perfusion rate were also different between the 40-L bioreactor cultures and the 250-mL satellite shake flask cultures, which may have contributed to the differences observed in culture metabolism. This was supported by improved glucose, lactate, and glutamate metabolism in satellite shake flask cultures agitated at a higher frequency. The late harvest product yield on aerobic glucose was higher and glutamate consumption was lower in the satellite shake flask cultures agitated at a higher frequency. This indicates that the mechanism that resulted in less efficient glucose consumption and utilization of alternative carbon/nitrogen sources can be suppressed by an improved mixing strategy.

In sum, these data indicate that a 250-mL shake flask cultures (as described herein) can be used to accurately model the growth and recombinant protein production achieved in a larger bioreactor culture.

Example 4. Satellite Shake Flask Cultures to Test Various Culture Media

To mitigate the risk of viral contamination and to promote consistent cell culture performance, mammalian cell culture processes are being transitioned away from the use of animal-derived media components. In this study chemically-defined, animal-component free CD hydrolysate supplements were evaluated in recombinant human alpha-galactosidase harvest stage satellite shake flask cultures (described herein). Hydrolysate supplements are synthetic alternatives to undefined hydrolysates and contain pure sources of soluble amino acids, peptides, vitamins, and essential elements, and are also formulated to have minimal pH and osmolarity impact upon addition to a base culture medium.

In this study, four different culture media were tested in 8 flasks, using CD hydrolysate supplement from 2 vendors: Sigma-Aldrich and Becton, Dickinson, and Co. (BD). The four conditions were 1× CD hydrolysate (from Sigma-Aldrich), 1× CD hydrolysate (BD), 10% yeast extract (BD, 1.5 g/L in flasks), and a control (925 media without supplement). Harvest phase recombinant human alpha-galactosidase culture was taken from P404 and P407 (40-L recombinant human alpha-galactosidase bioreactor cultures) on H27, and used to inoculate eight satellite shake flasks (on H28). The first batch re-feed using the formulated media (with or without CD hydrolysate or yeast extract) was performed on H29.

Procedures 250-mL Satellite Shake Flask Cultures

Figure 24:
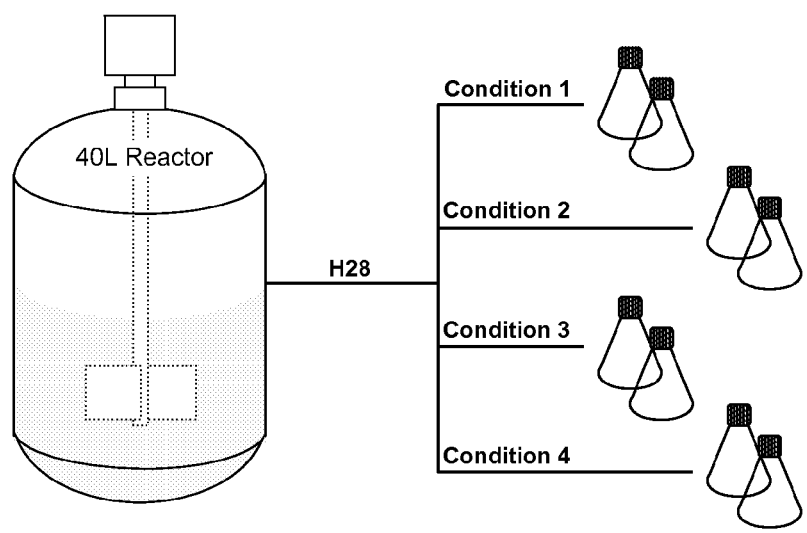
FIG. 24 is a schematic diagram showing the design of the harvest phase satellite shake flask CD-hydrolysate study.

The culture used for this study was maintained from seed thaw to harvest phase at the 40-L bioreactor scale. Well-mixed microcarrier cell culture samples (400 mL) were transferred from two 40-L bioreactor cultures to one shake flask on harvest day 27 (FIG. 24). This culture was then used to inoculate eight 250-mL shake flasks (two for each tested culture medium) on H28. The first re-feed using conditioned media (with or without CD hydrolysate supplement) was performed on H29. Shake flasks with a working volume of 50 mL were run in duplicate for each of four culture media in parallel with the 40-L bioreactor cultures (Table 4). The satellite shake flask cultures were maintained in an ATR incubator at 36° C., 95 RPM, 5% $CO_2$, and 80% humidity.

During the course of the experiment, 2 batches of media were made to use throughout the experiment. One batch was made on H28 prior to the start of the satellite shake flask cultures. The second batch was made on H37, but used for first re-feed on H42 after sampling. Therefore the first point on the graphs which reflects the second batch of media is H44. The following parameters were closely monitored to evaluate the health of each culture: cell growth and viability, metabolism, and productivity.

TABLE 4

Four Growth Media Tested in Satellite Shake Flask Study

| Condition # | Condition details | Media formulation | pH after formulation (at 36° C.) | Osmolality after formulation |
|---|---|---|---|---|
| 1 | 1× CD-Hydrolysate (Sigma) | Stock solution of 20× made (400 mL DIWater, 17.36 g supplement powder, NaOH dropwise to pH ~7, DIWater to 500 mL volume, final pH 7.016) In order to get 1× concentration (1.74 g/L), 50 mL supplement is added to 1 L of 925 medium, and sterile filtered. | 7.113 | 282 |
| 2 | 1× CD-Hydrolysate (BD) | Stock solution sent from BD was 50× In order to get 1× concentration, 20 mL supplement is added to 1 L of 925 medium, and sterile filtered. | 7.103 | 282 |
| 3 | 10% Yeast extract (1.5 g/L in flasks) | Yeast extract sent to us from BD is 10% solution (10 g/100 mL) To get final concentration of 1.5 g/L, 15 mL of 10% extract (as sent) is added to 1 L of 925 medium, and sterile filtered. | 7.125 | 284 |
| 4 | Control (925 media) | 925 media formulation, made by 45 NYA support services (PN 1974-03) | 7.122 | 281 |

Results

Figure 25:
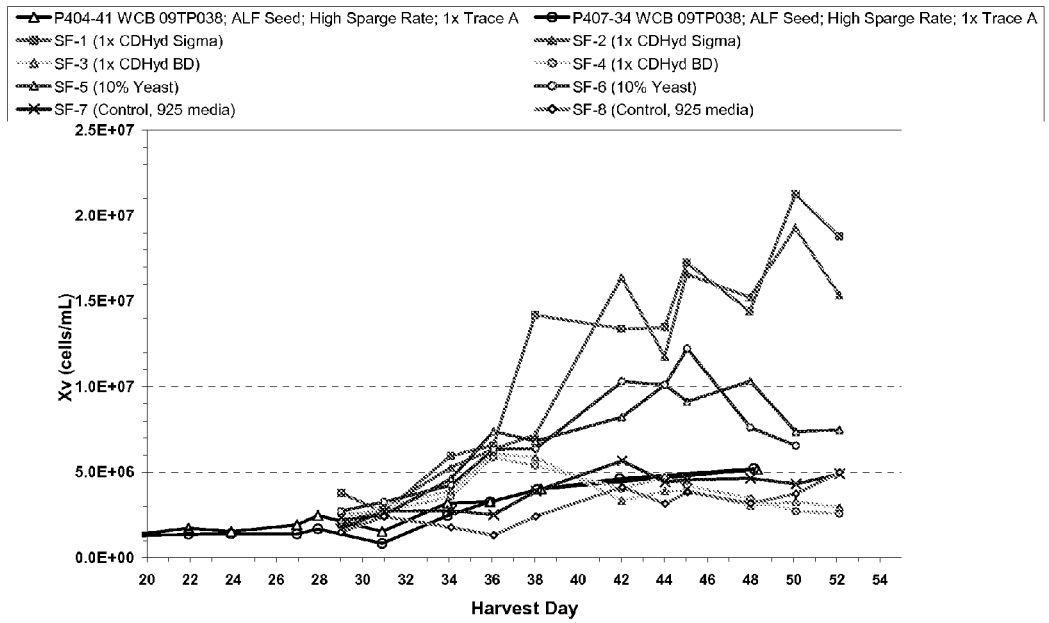
FIG. 25 is a graph of the viable cell concentration in each harvest phase satellite shake flask culture and each 40-L bioreactor culture over time.

The 1× CD hydrolysate supplement from Sigma-Aldrich showed the highest viable cell density, reaching densities of $20 \times 10^6$ cells/mL after trough recovery. The data for the 925 control satellite shake flask cultures and the 40-L bioreactor culture counterparts are consistently similar. The positive control (10% yeast extract supplement) also showed higher growth than the controls, reaching densities of $10 \times 10^6$ cells/mL, though not as high as the culture supplemented with CD hydrolysate from Sigma-Aldrich. Though the CD hydrolysate supplement from BD also showed cell growth after re-feeding on H29, growth stopped and the culture began to plateau or crash after H36 (FIG. 25).

Figure 26:
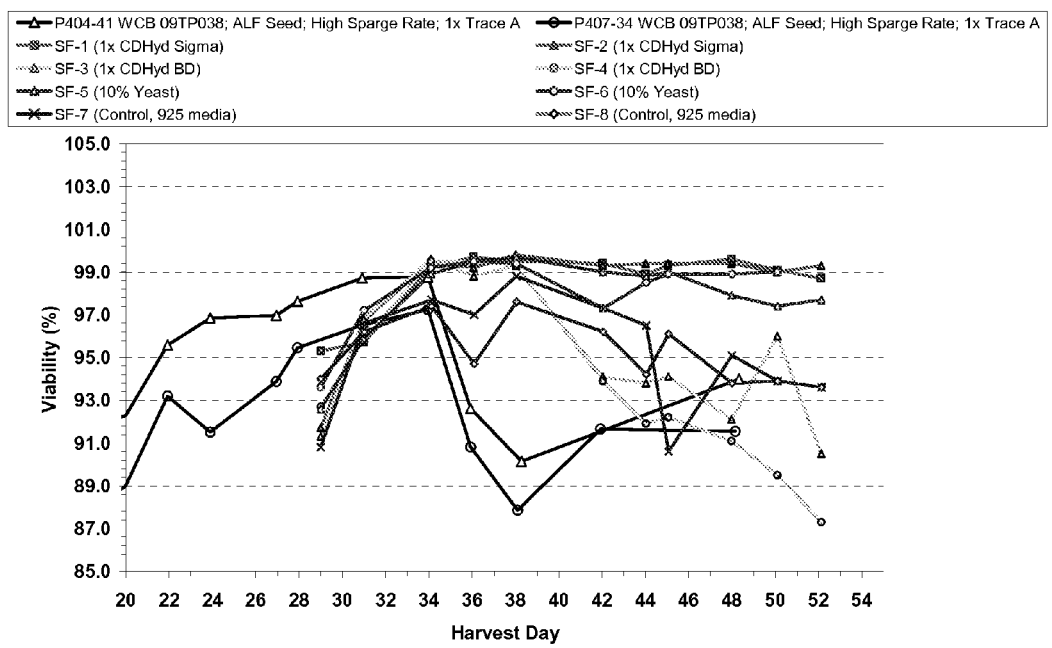
FIG. 26 is a graph of the percentage of viable cells in each harvest phase satellite shake flask culture and each 40-L bioreactor culture over time.
Figure 27:
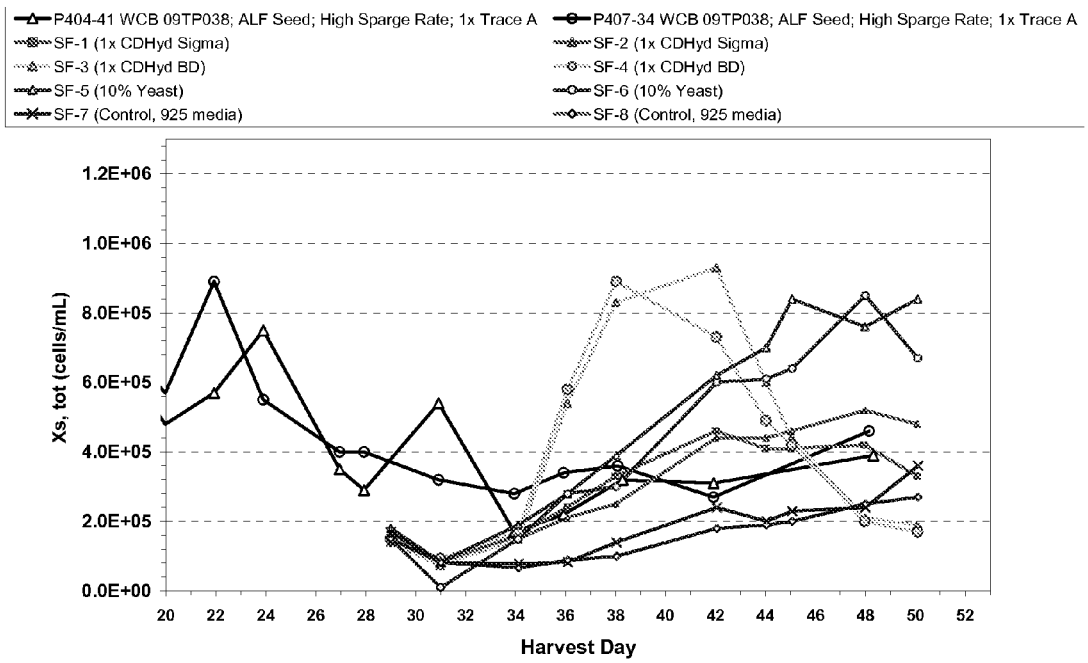
FIG. 27 is a graph of the suspended cell concentration over time in each harvest phase satellite shake flask culture and each 40-L bioreactor culture over time.

The viability remained highest with the CD hydrolysate supplement from Sigma-Aldrich and the 10% yeast extract (>95%). The negative control culture (with only 925 media) and the CD hydrolysate supplement from BD showed relatively high viability up to H36, after which they both began to decline (FIG. 26). While the total suspension cell concentration remained relatively low in the control flasks (with only 925 media) and lower viable cell concentration, the suspension cell concentration increased and then decreased in the BD CD hydrolysate-supplemented flasks, and it remained relatively low in the Sigma Aldrich CD hydrolysate-supplemented flasks, which correlates with a high viable cell concentration (which shows that the Sigma-Aldrich CD hydrolysate-supplemented culture was healthy). The 10% yeast extract-supplemented satellite shake flask culture had the highest concentration of suspension cells (FIG. 27).

The glucose concentration profile reflected the viable cell density growth profile, with glucose the most consumed in the Sigma-Aldrich CD hydrolysate-supplemented culture and the 10% yeast extract-supplemented culture. Glucose consumption turned from positive to negative on H36 when cell growth declined in the BD CD hydrolysate-supplemented culture.

The lactate concentration for all conditions was high at the beginning of the satellite shake flask cultures due to a drop in $CO_2$ (to 5%), which cannot be actively controlled in the ATR incubators. As glucose metabolism climbed in the Sigma-Aldrich CD hydrolysate- and yeast extract-supplemented satellite shake flask cultures, the lactate concentration also grew. The lactate concentration in the BD CD hydrolysate supplemented-satellite shake flask cultures dropped after H36 as the metabolism declined. The glutamine consumption trended similar to 40-L bioreactor cultures in all satellite shake flask cultures, though its consumption is higher in Sigma-Aldrich CD hydrolysate-supplemented satellite shake flask cultures and yeast extract-supplemented satellite shake flask cultures, where the viable cell density was higher.

Figure 28:
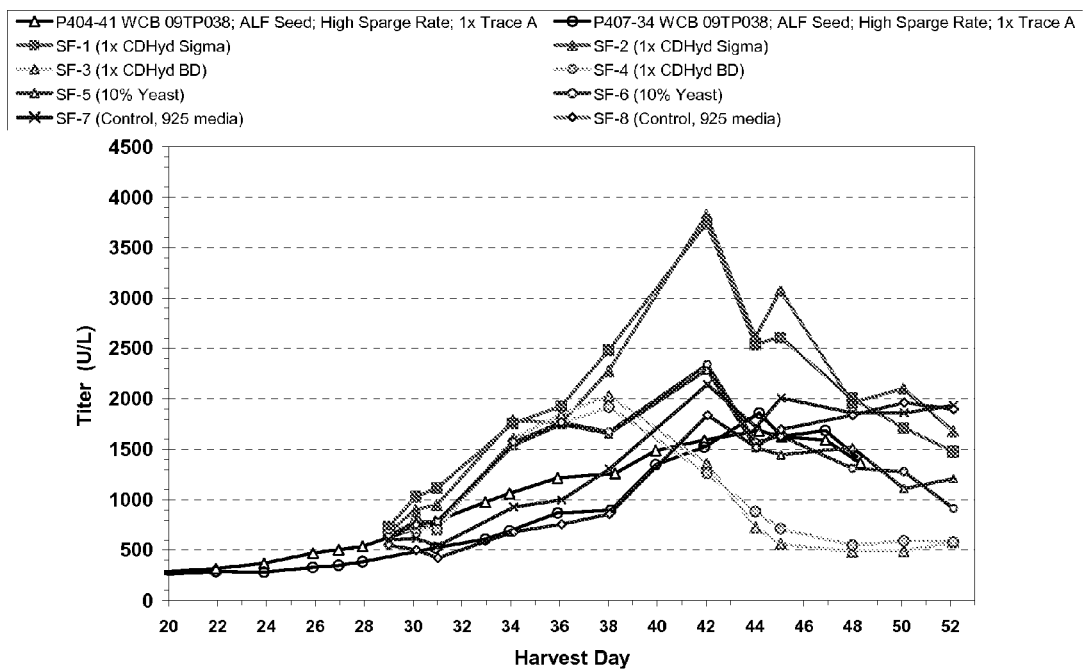
FIG. 28 is a graph of the titer (units/L) of recombinant human alph-galactosidase present in each harvest phase satellite shake flask culture and each 40-L bioreactor culture over time.

The titer profile of the four different culture media reveals that the Sigma-Aldrich CD hydrolysate supplement boosted the titer up to ~3700 U/L till H42 (the highest of the four tested culture media), and then showed a steady decline to ~1500 U/L by H52. The control satellite shake flask cultures with only 925 media showed a steady increase in titer up to ~1500 U/L by H52, similar to the 40-L parent bioreactor cultures. The 10% yeast extract supplement caused an initial climb in titer which dropped after H42. Consistent with other parameters, the BD CD hydrolysate-supplemented culture crashed after H36. Both the CD hydrolysate supplements from Sigma-Aldrich and BD offered immediate trough recovery (FIG. 28).

Figure 29:
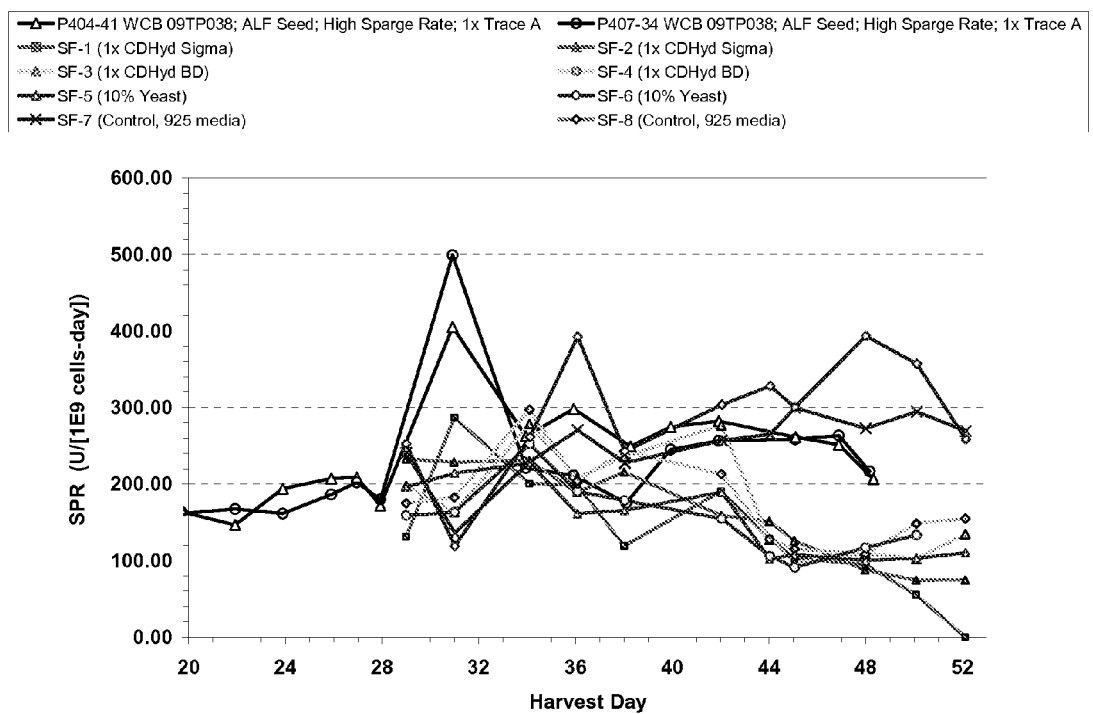
FIG. 29 is a graph of the specific productivity rate (SPR) of recombinant human alpha-galactosidase (units/[$1\times10^9$ cells·day]) for each harvest phase satellite shake flask culture and each 40-L bioreactor culture over time.

The specific productivity rate (SPR) was similar for all of the tested culture media, except for the control 925 culture medium, which shows a similar trend to the parent 40-L bioreactor cultures. The SPR of all the other tested culture media is similar to each other and the control flasks, though they drop off around H40 (FIG. 29).

Finally, the cumulative volumetric productivity rate (VPR) profile shows the cumulative productivity of recombinant human alpha-galactosidase based on the dilution factor of the shake flask cultures. These data show that satellite shake flask cultures containing the CD hydrolysate supplement from Sigma-Aldrich showed the highest productivity, the rate of which only slightly decreased after ~H45. A lower cumulative VPR was seen in the satellite shake flask cultures containing the (positive control) yeast extract, and an even further decreased cumulative VPR was seen in the satellite shake flask cultures containing the CD hydrolysate supplement from BD, where the cumulative VPR flattened (product titer declined) after H38. The control satellite shake flask cultures showed a steady increase in cumulative VPR as the titer increased, though it did not reach a similar level to the satellite shake flask cultures containing the CD hydrolysate supplement from Sigma-Aldrich.

The pH and $pO_2$ in the satellite shake flask cultures were very different from the parent 40-L bioreactor cultures due to the lack of active control for these parameters. The $CO_2$ for the satellite shake flask cultures was much lower (35-45 mmHg) compared to the parent 40-L bioreactor cultures (85-95 mmHg) during this phase. This is due to the very high sweep efficiency of the satellite shake flask cultures and the low 5.0% $CO_2$ set point of the ATR incubator. The Sigma CD hydrolysate-supplemented satellite shake flask culture and the yeast extract-supplemented satellite shake flask culture pH started with a high pH (around 7.1) and dropped to about 6.4-6.6 by H53, in direct response to the lactate concentration. The BD CD hydrolysate-supplemented satellite shake flask culture initially showed a drop in pH as metabolism picked up, but as the culture began to decline at H36, the pH also increased as the lactate concentration dropped.

The $pO_2$ trend confirmed the culture performance of the Sigma-Aldrich CD hydrolysate-supplemented satellite shake flask culture and the 10% yeast extract-supplemented satellite shake flask culture, which showed a consistent decline in $pO_2$ concentration as the viable cell concentration increased. In keeping with the decline of metabolism and cell growth after H36, the BD CD hydrolysate-supplemented satellite shake flask culture showed an increase in oxygen concentration after this point. The control satellite shake flask cultures showed a relatively flat trend; only a slight decrease in pH and $pO_2$ over the duration of the satellite shake flask culture as the viable cell density grew from $2.5\times10^6$ to $5.0\times10^6$ over 24 harvest days.

The Sigma-Aldrich CD hydrolysate supplement led to the highest increase in cell growth and titer performance during the length of this study. It was concluded that a 1× concentration of the BD CD hydrolysate supplement is not beneficial to the culture since it did not recover fully after coming out of the trough period, and a severe and irreversible culture decline was noted at around H36.

Overall, it can be concluded that the addition of CD hydrolysate supplement to 925 medium improves recombinant human alpha-galactosidase mid-harvest stage productivity. Of the different culture media tested, the CD hydrolysate supplement from Sigma-Aldrich led to the highest increase in cell growth and titer between H28 and H52. At the concentration tested, the CD hydrolysate supplement from BD did not aid in full recovery out of the trough. CD hydrolysates do appear to improve mid-harvest stage productivity, but this effect diminishes in the late harvest phase, at the concentration tested.

These data demonstrate that the methods described herein can be used to test the effect of different culture media, different supplements, and different raw materials that are used to generate a liquid culture medium on a method of manufacturing a recombinant protein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of culturing an adherent mammalian cell, the method comprising:
   providing a shake flask containing an adherent mammalian cell disposed in a first liquid culture medium, wherein the first liquid culture medium occupies about 20% to about 30% of the volume of the shake flask and contains a plurality of microcarriers at a concentration of about 1.0 g/L to about 15.0 g/L;
   incubating the shake flask for a period of time at about 32° C. to about 39° C. and with a rotary agitation of about 85 revolutions per minute (RPM) to about 125 RPM; and
   after about the first 48 to 96 hours of the period of time, continuously or periodically removing a first volume of the first liquid culture medium and adding to the first liquid culture medium a second volume of a second liquid culture medium, wherein the first and second volumes are about equal, and the method achieves a viable cell density of greater than $2\times10^6$ cells/mL in the first liquid culture medium or a combination of the first liquid culture medium and the second liquid culture medium at some point during the period of time.

2. The method of claim 1, wherein the adherent mammalian cell contains a nucleic acid encoding a recombinant protein.

3. The method of claim 1, wherein the removing of the first volume of the first liquid culture medium and the adding of the second volume of the second liquid culture medium is performed periodically.

4. The method of claim 1, wherein the first volume of the first liquid culture medium removed and the second volume of the second liquid culture medium added are increased over time.

5. The method of claim 1, wherein the shake flask is gas-permeable and has a volume of between about 20 mL to about 1 L.

6. The method of claim 1, wherein the adherent mammalian cell is suspended in about 40 mL to about 80 mL of the first liquid culture medium.

7. The method of claim 1, wherein after about the first 48 to 96 hours of the period of time, in each 24-hour period, the first volume of the first liquid culture medium removed and the second volume of the second liquid culture medium added is about 30% to about 95% of the volume of the first liquid culture medium.

8. The method of claim 1, wherein the shake flask is incubated at an angle of about 45 degrees relative to the benchtop or the horizon.

9. A method of culturing an adherent mammalian cell, the method comprising:
   (a) providing a shake flask containing an adherent mammalian cell disposed in a first liquid culture medium that occupies about 20% to about 30% of the volume of the shake flask and contains a plurality of microcarriers in a concentration of about 1.0 g/L to about 15.0 g/L;
   (b) incubating the shake flask for a first time period at about 35° C. to about 39° C. with a rotary agitation of about 85 revolutions per minute (RPM) to about 125 RPM, and after about the first 48 to 96 hours of the first period of time, in each subsequent 24-hour period,
      (i) continuously or periodically removing a first volume of the first liquid culture medium that is substantially free of microcarriers from the shake flask, wherein the first volume is about 10% to about 95% of the volume of the first liquid culture medium; and
      (ii) adding to the shake flask a second volume of a second liquid culture medium, wherein the first and second volumes are about equal;
   (c) incubating the shake flask after the cell concentration reaches about target cell density for a second time period of about 2 days to about 7 days, at about 32° C. to about 39° C. with the rotary agitation, and in each 24-hour period, performing steps (b)(i) and (b)(ii), wherein the first and second liquid culture media used in step (b) are of a substantially different type from those used in step (c); and
   (d) incubating the shake flask for a third time period greater than 2 days, at about 35° C. to about 39° C. with the rotary agitation, and in each 24-hour period, performing steps (b)(i) and (b)(ii), wherein the first and second liquid culture media used in step (c) are of the same type as those used in step (d).

10. The method of claim 9, wherein the adherent mammalian cell contains a nucleic acid encoding a recombinant protein.

11. The method of claim 9, wherein the shake flask is gas-permeable and has a volume of between about 20 mL to about 1 L.

12. The method of claim 9, wherein the volume of the first liquid culture medium is about 40 mL to about 80 mL.

13. The method of claim 9, wherein the first volume of the first liquid culture medium removed and the second volume of the second liquid culture medium added in one or more of the first time period, the second time period, and the third time period is about 70% of the volume of the first liquid culture medium.

14. The method of claim 9, wherein the shake flask is incubated in (b), (c), and (d) at an angle of about 45 degrees relative to the benchtop or the horizon.

15. The method of claim 2, further comprising:
   recovering the recombinant protein from the adherent mammalian cell or from the first and/or second liquid culture medium.

16. The method of claim 10, further comprising:
   (e) recovering the recombinant protein from the adherent mammalian cell or the first and/or second liquid culture medium used during the first, second, and/or third period of time.

17. The method of claim 2, further detecting the recombinant protein in the cell or in the first and/or second culture medium; and
   comparing the amount of recombinant protein present in the cell or in the first and/or second culture medium to a reference level of recombinant protein.

* * * * *